(12) United States Patent
Schlumpf et al.

(10) Patent No.: US 10,632,168 B2
(45) Date of Patent: Apr. 28, 2020

(54) COLLAGEN PEPTIDE-BASED MEDICAMENT COMPOSITIONS AND DEVICES AND METHODS OF PRODUCTION AND USE THEREOF

(71) Applicant: Sustain Holdings, LLC, Stuart, FL (US)

(72) Inventors: Richard Eric Schlumpf, Stuart, FL (US); Robert Baratta, Stuart, FL (US); Shawn A. Delorey, Charlotte, NC (US)

(73) Assignee: SUSTAIN HOLDINGS, LLC, Stuart, FL (US)

( * ) Notice: Subject to any disclaimer, the term of this patent is extended or adjusted under 35 U.S.C. 154(b) by 0 days.

(21) Appl. No.: 15/945,820

(22) Filed: Apr. 5, 2018

(65) Prior Publication Data
US 2018/0325977 A1   Nov. 15, 2018

Related U.S. Application Data

(60) Provisional application No. 62/581,927, filed on Nov. 6, 2017, provisional application No. 62/482,592, filed on Apr. 6, 2017.

(51) Int. Cl.
| | |
|---|---|
| A61L 27/22 | (2006.01) |
| A61L 27/24 | (2006.01) |
| A61L 27/54 | (2006.01) |
| A61L 17/08 | (2006.01) |
| A61K 38/39 | (2006.01) |
| C07K 14/47 | (2006.01) |
| A61K 38/01 | (2006.01) |
| A61K 9/00 | (2006.01) |
| A61K 45/06 | (2006.01) |
| A61L 29/08 | (2006.01) |
| A61L 31/16 | (2006.01) |
| A61L 31/04 | (2006.01) |
| A61L 31/10 | (2006.01) |
| C07K 14/78 | (2006.01) |
| A61L 29/16 | (2006.01) |
| A61L 27/10 | (2006.01) |
| A61L 29/04 | (2006.01) |
| A61P 17/00 | (2006.01) |
| A61K 31/497 | (2006.01) |
| A61K 31/351 | (2006.01) |
| A61P 35/00 | (2006.01) |

(52) U.S. Cl.
CPC .......... *A61K 38/014* (2013.01); *A61K 9/0014* (2013.01); *A61K 38/39* (2013.01); *A61K 45/06* (2013.01); *A61L 17/08* (2013.01); *A61L 27/10* (2013.01); *A61L 27/24* (2013.01); *A61L 27/54* (2013.01); *A61L 29/045* (2013.01); *A61L 29/085* (2013.01); *A61L 29/16* (2013.01); *A61L 31/044* (2013.01); *A61L 31/10* (2013.01); *A61L 31/16* (2013.01); *C07K 14/78* (2013.01); *A61K 31/351* (2013.01); *A61K 31/497* (2013.01); *A61K 2300/00* (2013.01); *A61L 2400/12* (2013.01); *A61P 17/00* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 5,120,764 A | 6/1992 | McCarthy et al. | |
| 5,201,456 A | 4/1993 | Reynal et al. | |
| 5,252,608 A | 10/1993 | Palfreyman et al. | |
| 5,973,112 A | 10/1999 | Raines et al. | |
| 6,197,934 B1 | 3/2001 | DeVore et al. | |
| 6,448,378 B2 | 9/2002 | DeVore et al. | |
| 6,946,440 B1 | 9/2005 | DeWoolfson et al. | |
| 7,122,521 B2 | 10/2006 | Raines et al. | |
| 7,402,562 B2 | 7/2008 | DeWoolfson et al. | |
| 7,858,741 B2 | 12/2010 | Raines et al. | |
| 8,283,414 B2 | 10/2012 | Yu et al. | |
| 8,461,303 B2 | 6/2013 | Smith et al. | |
| 8,658,167 B2 | 2/2014 | Smith et al. | |
| 8,680,246 B2 | 3/2014 | McCauley et al. | |
| 8,883,964 B2 | 11/2014 | Yu et al. | |
| 9,176,139 B2 | 11/2015 | Smith et al. | |

(Continued)

FOREIGN PATENT DOCUMENTS

WO   2016/165788 A1   10/2016

OTHER PUBLICATIONS

Karlen et al., "Deep sclerectomy with collagen implant: medium term results," Br. J. Ophthalmol. 83:6-11 (1999) (Year: 1999).*

(Continued)

*Primary Examiner* — Julie Ha
*Assistant Examiner* — Kristina M Hellman
(74) *Attorney, Agent, or Firm* — Medler Ferro Woodhouse & Mills PLLC

(57) ABSTRACT

The present invention is in the fields of medicinal chemistry, biotechnology and pharmaceuticals. The invention provides compositions comprising one or more collagen mimetic peptides, optionally attached to one or more therapeutic compounds or one or more imaging compounds, for use in methods of treating, preventing, ameliorating, curing and diagnosing certain diseases and physical disorders in humans and veterinary animals, as well as methods of manufacturing such composition. The invention also provides medical devices comprising one or more such compositions of the invention. The invention also provides methods of use of such compositions and devices in treating and diagnosing certain diseases and physical disorders in humans and veterinary animals, including ocular diseases or disorders, skin diseases or disorders, certain cancers, particularly intraluminal cancers, gastrointestinal diseases or disorders, genitourinary tract diseases or disorders, fibrotic diseases/disorders and rheumatic diseases/disorders.

23 Claims, 1 Drawing Sheet
Specification includes a Sequence Listing.

(56) References Cited

U.S. PATENT DOCUMENTS

| | | | |
|---|---|---|---|
| 9,255,086 B2 | 2/2016 | Arora et al. | |
| 9,289,396 B2 | 3/2016 | Devore et al. | |
| 9,289,447 B2 | 3/2016 | Smith et al. | |
| 9,399,102 B2 | 7/2016 | Dewoolfson et al. | |
| 9,623,129 B2 | 4/2017 | Gonzales et al. | |
| 9,758,569 B2 | 9/2017 | Raines et al. | |
| 9,988,434 B2 | 6/2018 | Raines et al. | |
| 2007/0275897 A1 | 11/2007 | Raines et al. | |
| 2008/0287342 A1* | 11/2008 | Yu | A61K 38/10 514/1.1 |
| 2012/0195828 A1 | 8/2012 | Nakamura et al. | |
| 2013/0129807 A1* | 5/2013 | Devore | A61K 47/42 424/443 |
| 2013/0164220 A1 | 6/2013 | Yu et al. | |
| 2015/0111308 A1 | 4/2015 | Yu et al. | |
| 2015/0209472 A1 | 7/2015 | McCoy | |
| 2016/0075764 A1 | 3/2016 | Raines et al. | |
| 2016/0215018 A1* | 7/2016 | Yang | C07K 14/78 |
| 2018/0111979 A1 | 4/2018 | Phopase | |

OTHER PUBLICATIONS

Dada et al., "Trabeculectomy With Combined Use of Subconjunctival Collagen Implant and Low-dose Mitomycin C," J. Glaucoma 22:659-662 (2013) (Year: 2013).*

Wipperman et al., "Evaluation and Management of Corneal Abrasions," American Family Physician 87: 114-120 (2013) (Year: 2013).*

Abelson et al., "Glaucoma and Dry Eye: A Tough Combo," Rev. Ophthalmology (Oct. 2011), accessed Nov. 1, 2019 at URL: reviewofophthalmology.com/article/glaucoma-and-dry-eye-a-tough-combo, pp. 1-7 (Year: 2011).*

Albu et al., "Collagen-Based Drug Delivery Systems for Tissue Engineering", in: Biomaterials Applications for Nanomedicine, Prof. Pignatello, R. (Ed.), 2011, ISBN: 978-953-307-661-4, DOI: 10.5772/22981, Rijeka, Croatia: InTech, available from: https://www.intechopen.com/books/biomaterials-applications-for-nanomedicine/collagen-based-drug-delivery-systems-for-tissue-engineering.

An et al., "Collagen interactions: Drug design and delivery," Advanced Drug Delivery Reviews (2016) 97:69-84.

Bala et al., "PLGA nanoparticles in drug delivery: the state of the art.," Critical Reviews in Therapeutic Drug Carrier Systems (2004) 21(5):387-422.

Bautista et al., "Insulin-like growth factors I and II are present in the skeletal tissues of ten vertebrates," Metabolism (1990) 39(1):96-100.

Besseau et al., "Stabilization of Fluid Cholesteric Phases of Collagen to Ordered Gelated Matrices", J. Mol. Biol. (1995) 251:197-202.

Bondareva et al., "The Lysyl Oxidase Inhibitor, β-Aminopropionitrile, Diminishes the Metastatic Colonization Potential of Circulating Breast Cancer Cells," PLoS ONE (2009) 4(6):e5620.

Bradley, "Some mechanical property considerations of reconstituted collagen for drug release supports", Biomaterials, Medical Devices, and Artificial Organs (1997) 5(2):159-175.

Buechter et al., "Co-translational Incorporation of Trans-4-Hydroxyproline into Recombinant Proteins in Bacteria," Journal of Biological Chemistry (2003) 278(1):645-650.

Carlson et al., "Impact of Hyaluronic Acid-Containing Artificial Tear Products on Reepithelialization in an In Vivo Corneal Wound Model," Journal of Ocular Pharmacology and Theapeutics, published online Feb. 2, 2018, accessed at https://doi.org/10.1089/jop.2017.0080.

Cavallaro et al., "Collagen Fabrics as Biomaterials", Biotechnology and Bioengineering (1994) 43:781-791.

Chak et al., "A Review of Collagen Based Drug Delivery Systems," International Journal of Pharmacy & Teaching and Practices (2013) 4(4):811-820.

Chan et al., "Photochemical crosslinking improves the physicochemical properties of collagen scaffolds", J. Biomed. Mater. Res. (2005) 75A:689-701.

Chattopadhyay et al., "Anchoring a Cytoactive Factor in a Wound Bed Promotes Healing," Journal of Tissue Engineering Regenerative Medicine (2014) 10(12):1012-1020.

Chattopadhyay et al., "Peptides that anneal to natural collagen in vitro and ex vivo.," Organic & Biomolecular Chemistry (2012) 10(30):5892-5897.

Chattopadhyay et al., "Collagen-based biomaterials for wound healing," Biopolymers (2014)101(8):821-833.

Chung et al., "Collagenase unwinds triple-helical collagen prior to peptide bond hydrolysis," The EMBO Journal (2004) 23(15):3020-3030.

Cooperman et al., "The immunogenicity of injectable collagen. I. A 1-year prospective study," Journal of the American Academy of Dermatology (1984) 10(4):638-646.

Coudrillier et al., "Glaucoma-related Changes in the Mechanical Properties and Collagen Micro-architecture of the Human Sclera," PLoS ONE (2015) (10):e0131396.

Davis et al., "Regulation of Tissue Injury Responses by the Exposure of Matricryptic Sites within Extracellular Matrix Molecules," American Journal of Patholofy (2000) 156(5):1489-1498.

Del Bouno et al., "Procol™, a New Technology for Drug Delivery," Sustain Biotechnology.

Dua et al., "The collagen matrix of the human trabecular meshwork is an extension of the novel pre-Descemet's layer (Dua's layer)," British Journal of Ophthalmology (2014) 98(5):691-697.

Ellison et al., "Convenient Synthesis of Collagen-Related Tripeptides for Segment Condensation," Peptide Science (2015) 104(6):676-681.

Epstein, Howard, "Cosmeceutical Vehicles," Clininical Dermatology (2009) 27(5):453-460.

Erler et al., "Hypoxia-induced lysyl oxidase is a critical mediator of bone marrow cell recruitment to form the pre-metastatic niche," Cancer Cell (2009) 15(1):35-44.

Erler, J.T., et al., "Lysyl oxidase is essential for hypoxia-induced metastasis," Nature (2006) 440(27):1222-1226.

Fallas, et al., "Synthetic collagen mimics: self-assembly of homotrimers, heterotrimers and higher order structures," Chem Soc Rev (2010) 39:3510-3527.

Fang et al., "Collagen as a double-edged sword in tumor progression," Tumour Biology: The Journal of the International Society for Oncodevelopmental Biology and Medicine (2014) 35(4):2871-2882.

FDA Drug Safety Communication: FDA updates warnings for oral and injectable fluoroquinolone antibiotics due to disabling side effects, accessed Nov. 6, 2017, at https://www.fda.gov/Drugs/DrugSafety/ucm511530.htm.

Fleischmajer et al., "Dermal collagen fibrils are hybrids of type 1 and type 3 collagen molecules," Journal of Strutural Biology (1990) 105:162-169.

Frenkel et al., "Chondrocyte transplantation using a collagen bilayer matrix for cartilage repair," The Journal of Bone and Joint Surgery (1997) 79-B:831-836.

Gaudana et al., "Ocular Drug Delivery," The AAPS Journal (2010) 12(3):348-360.

Garg et al., "To Study the Efficacy of Difluprednate Opthalmic Emulsion and Prednisolone Acetate Opthalmic Suspension on Postoperative Inflammation in Cataract Surgery," Journal of Clinical and Diagnostic Research (2016) 10(12):NC05-NC08.

Gelse et al., "Collagens—structure, function, and biosynthesis," Advanced Drug Delivery Reviews (2003) 55(12):1531-1546.

Giusti et al., "Collagen-based new bioartificial polymeric materials," Biomaterials (1994) 15(15):1229-1233.

Gottlieb et al., "Self-Assembled collagen-like peptide fibers as templates for metallic nanowires," Journal of Materials Chemistry (2008) 18:3865-3870.

Grabarek et al., "Zero-length crosslinking procedure with the use of active esters," Analytical Biochemistry (1990) 185:131-135.

Granchi et al., "Bioreductively Activated Lysyl Oxidase Inhibitors against Hypoxic Tumours," ChemMedChem (2009) 4(10):1590-1594.

(56) References Cited

OTHER PUBLICATIONS

Hay, Elizabeth D., "Extracellular matrix," Journal of Cell Biology (1981) 91(3):205-223.
Hodges et al., "Stereoelectronic and Steric Effects in the Collagen Triple Helix: Toward a Code for Strand Association," J. A,. Chem. Soc. (2005) 127:15923-15932.
Hong et al., "Collagenase-Mediated Tissue Modeling of Corneal Ectasia and Collagen Cross-Linking Treatments," Investigative Ophthalmology & Visual Science (2012) 53(4):2321-2327.
Huang et al., "Collagen: A potential factor involved in the pathogenesis of glaucoma," Medical Science Monitor Basic Research (2013) 19:237-240.
Hulmes, D.J.S., "Collagen Diversity, Synthesis and Assembly," in: Collagen: Structure and Mechanics (2008) pp. 15-47.
Jangamreddy et al., "Short peptide analogs as alternatives to collagen in pro-regenerative corneal implants," Acta Biomaterialia (2018) 69:120-130.
Jones et al., "Analysis of structural design-features in collagen," Journal of Molecular Biology (1991) 218:209-219.
Joseph et al., "Drug delivery to the eye: what benefits to nanocarriers offer?," Nanomedicine (Lond.) (2017) 12(6):683-702.
Karthikeyan et al., "The concept of ocular inserts as drug delivery systems: An overview," Asian Journal of Pharmaceutics (2008) 2(4):192-200.
Kelkar et al., "Theranostics: combining imaging and therapy," Bioconjugate Chem (2011) 22:1879-1903.
Kolenik et al., "Use of a Lyophilized Bovine Collagen Matrix in Postoperative Wound Healing," Dermatol Surg (1999) 25:303-307.
Kumar et al., "A Nanostructured Synthetic Collagen Mimic for Hemostasis," Biomacromolecules (2014) 15:1484-1490.
Kumar et al., "Polymer Gels: Perspectives and Applications," Springer (2018).
Lauer et al., "Collagen in Cancer," In: The Tumor Microenvironment, Springer-Verlag New York (2010) p. 477-507.
Lee et al., "Enhanced chondrogenesis of mesenchymal stem cells in collagen mimetic peptide mediated microenvironment," Tissue Engineering (2008) Part A 14(11):1843-1851.
Li et al., "Targeting and mimicking collagens via triple helical peptide assembly," Curr. Opin. Chem. Biol. (2013) 17:968-975.
Lodish,et al., "Collagen: The Fibrous Proteins of the Matrix", In: Molecular Cell Biology, 4th edition New York: W. H. Freeman, 2000, Section 22.3.
Luo et al., "Collagen-like peptides and peptide-polymer conjugates in the design of assembled materials," Eur Polym J (2013) 49(10):2998-3009.
Lutolf et al., "Synthetic biomaterials as instructive extracellular microenvironments for morphogenesis in tissue engineering," Nat Biotechnol (2005) 23(1):47-55.
Lynn et al., "Antigenicity and Immunogenicity of Collagen," Journal of Applied Biomedical Materials Research (2004) 71B:343-354.
Ma et al., "Crosslinking strategies for preparation of extracellular matrix-derived cardiovascular scaffolds," Regenerative Biomaterials (2014) 1(1):81-89.
Mattson et al., "A pratical approach to crosslinking," Molecular Biology Reports (1993) 17(3):167-183.
Niyibizi et al., "Bone Type V Collagen: Chain Composition and Location of a Trypsin Cleavage Site," Connective Tissue Research (1989) 20(1-4):247-250.
O'Reilly et al., "Endostatin: An Endogenous Inhibitor of Angiogenesis and Tumor Growth," Cell (1997) 88(2):277-285.
Ortega et al., "New functional roles for non-collagenous domains of basement membrane collagens," Journal Cell Science (2002)115:4201-4214.
Przbyla et al., "Higher-Order Assembly of Collagen Peptides into Nano- and Microscale Materials," J. Biochemistry (2010) 49:4411-4419.
Chopra et al., "Conformational implications of enzymatic proline hydroxylation in collagen," Proceedings of the National Academy of Science of the United States of America (1982) 79(23):7180-7184.
Rush et al., "Administration of Menadione, Vitamin K3, Ameliorates Off-Target Effects on Corneal Epithelial Wound Healing Due to Receptor Tyrosine Kinase Inhibition," Investigative Ophthalmology & Visual Science (2016) 57(14):5864-5871.
Rush et al., "Antagonizing c-Cbl Enhances EGFR-Dependent Corneal Epithelial Homeostasis," Investigative Ophthalmology & Visual Science (2014) 55(8):4691-4699.
Sakakibara, et al., "Synthesis of (Pro-Hyp-Gly)n of defined molecular weights Evidence for the stabilization of collagen triple helix by hydroxypyroline," Biochimica et Biophysica Acta (1973) 303(1):198-202.
Schlegel et al., "De novo bone formation using bovine collagen and platelet-rich plasma," Biomaterials (2004) 25(23):5387-5393.
Schuppan et al., "Collagens in the Liver Extracellular Matrix Bind Hepatocyte Growth Factor," Gastroenterology (1998) 114(1):139-152.
Shoulders et al., "Collagen structure and stability," Annual Review Biochememistry (2009) 78:929-958.
Siebler et al., "From Azidoproline to Functionalizable Collagen," Chimia (2013) 67:891-895.
Staros et al., "Enchancement by N-hydroxysulfosuccinimide of water-soluble carbodiimide-mediated coupling reactions," Analytical Biochemistry (1986) 156:220-222.
Strauss et al., "Advances in the design and higher-order assembly of collagen mimetic peptides for regenerative medicine," Current Opinion in Biotechnology (2017) 46:34-41.
Tanrikulu et al., "Peptide tessellation yields micron-scale collagen triple helices," Nat. Chem. (2016) 8(12):1008-1014.
Miyata et al., "Collagen Engineering for Biomaterial Use," Clinical Materials (1992) 9:139-148.
Timkovich, Russell, "Detection of the stable addition of carbodiimide to proteins," Analytical Biochemistry (1977) 79:135-43.
Wakitani, et al., "Repair of rabbit articular surfaces with allograft chondrocytes embedded in collagen gel," The Journal of Bone Joint Surgery (1989) 71-B:74-80.
Wang et al., "Facile Modification of Collagen Directed by Collagen Mimetic Peptides," J. Am. Chem. Soc. (2004):1.9.
Wollensak et al. "Riboflavin/ultraviolet-A-induced collagen crosslinking for the treatment of keratoconus"; American Journal of Ophthalmology, Ophthalmic (2003) 135(5):620-627.
Yamaguchi et al., "Negative regulation of transforming growth factor-β by the proteoglycan decorin," Nature (1990) 346:281-284.
Yu et al., "Collagen mimetic peptides: progress towards functional applications," Soft Matter (2011) 7:7927-7938.
Zhu et al., "Type IIA Procollagen Containing the Cyteine-rich Amino Propeptide Is Deposited in the Extracellular Matrix of Prechondrogenic Tissue and Binds to TGF-β1 and BMP-2," Journal of Cell Biology (1999) 144(5):1069-1080.

* cited by examiner

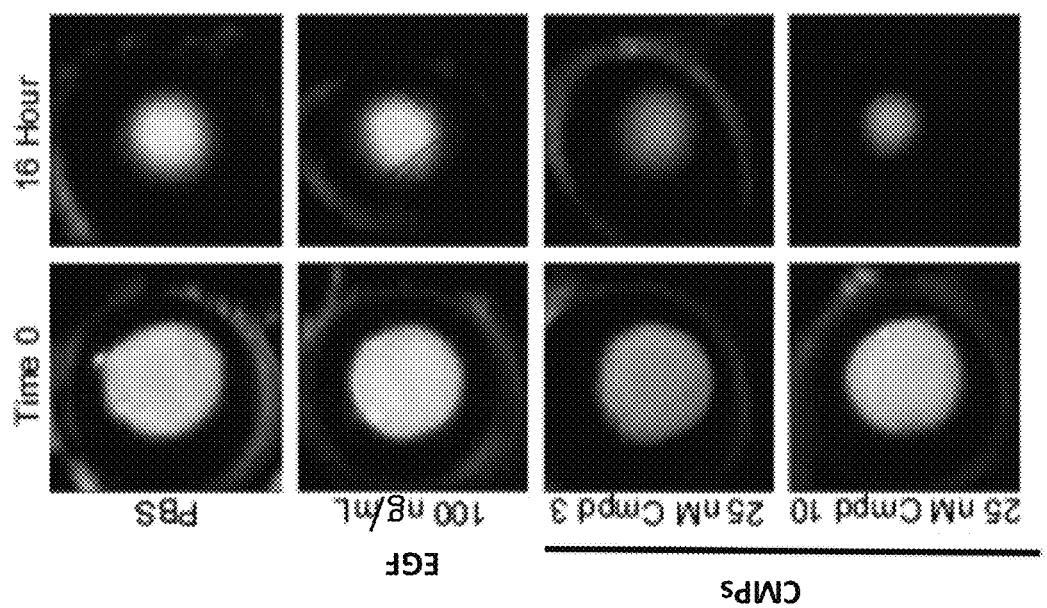

SEQUENCE LISTING

<160> NUMBER OF SEQ ID NOS: 398

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Pro Pro Gly Pro Pro Gly Pro Pro Gly Pro Pro Gly Pro Pro Gly
1               5                   10                  15

Pro Gly Pro Pro Gly
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4S-hydroxyproline
<220> FEATURE:
<221> NAME/KEY: MOD_RES
<222> LOCATION: (4)..(4)
<223> OTHER INFORMATION: 4S-hydroxyproline
<220> FEATURE:
<221> NAME/KEY: MOD_RES
<222> LOCATION: (7)..(7)
<223> OTHER INFORMATION: 4S-hydroxyproline
<220> FEATURE:
<221> NAME/KEY: MOD_RES
<222> LOCATION: (10)..(10)
<223> OTHER INFORMATION: 4S-hydroxyproline
<220> FEATURE:
<221> NAME/KEY: MOD_RES
<222> LOCATION: (13)..(13)
<223> OTHER INFORMATION: 4S-hydroxyproline
<220> FEATURE:
<221> NAME/KEY: MOD_RES
<222> LOCATION: (16)..(16)
<223> OTHER INFORMATION: 4S-hydroxyproline
<220> FEATURE:
<221> NAME/KEY: MOD_RES
<222> LOCATION: (19)..(19)
<223> OTHER INFORMATION: 4S-hydroxyproline

<400> SEQUENCE: 2

Pro Pro Gly Pro Pro Gly Pro Pro Gly Pro Pro Gly Pro Pro Gly
1               5                   10                  15

Pro Gly Pro Pro Gly
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4S-hydroxyproline
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (11)..(11)
<223> OTHER INFORMATION: 4S-hydroxyproline

```
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
<222> LOCATION: (20)..(20)
<223> OTHER INFORMATION: 4S-hydroxyproline

<400> SEQUENCE: 3

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (19)..(19)
<223> OTHER INFORMATION: Fluoroproline

<400> SEQUENCE: 4

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
```

```
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 5

Pro Pro Gly Pro Pro Gly Pro Pro Gly Pro Pro Gly Pro Pro Gly Pro
1               5                  10                  15

Pro Gly Pro Pro Gly
            20

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
```

```
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 6

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (19)..(19)
<223> OTHER INFORMATION: Chloroproline

<400> SEQUENCE: 7

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 8

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
```

```
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 9

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
```

<223> OTHER INFORMATION: Hydroxyproline

<400> SEQUENCE: 11

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 12

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

```
<220> FEATURE:
<221> NAME/KEY: MOD_RES
<222> LOCATION: (20)..(20)
<223> OTHER INFORMATION: Fluoroproline

<400> SEQUENCE: 13

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 14

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 16

Pro Cys Gly Pro Pro Gly Pro Pro Gly Pro Pro Gly Pro Pro Gly
1               5                   10                  15

Pro Gly Pro Pro Gly
            20

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Pro Gly Cys Pro Gly Pro Pro Gly Pro Pro Gly Pro Pro Gly
1               5                   10                  15

Pro Gly Pro Pro Gly
            20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Pro Gly Pro Cys Gly Pro Pro Gly Pro Pro Gly Pro Pro Gly
1               5                   10                  15

Pro Gly Pro Pro Gly
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Pro Gly Pro Pro Gly Pro Cys Gly Pro Pro Gly Pro Pro Gly
1               5                   10                  15

Pro Gly Pro Pro Gly
            20

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Pro Gly Pro Pro Gly Pro Pro Gly Cys Pro Gly Pro Pro Gly
1               5                   10                  15

Pro Gly Pro Pro Gly
            20

<210> SEQ ID NO 21

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Pro Gly Pro Pro Gly Pro Pro Gly Pro Pro Gly Cys Pro Gly Pro
1               5                   10                  15

Pro Gly Pro Pro Gly
            20

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Pro Gly Pro Pro Gly Pro Pro Gly Pro Pro Gly Pro Pro Gly Pro
1               5                   10                  15
```

```
Cys Gly Cys Pro Gly
            20

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 28

Cys Pro Gly Pro Pro Gly Pro Pro Gly Pro Pro Gly Pro Pro Gly Pro
1               5                   10                  15

Pro Gly Pro Pro Gly
            20
```

```
<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 29

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 30
```

-continued

```
Pro Pro Gly Cys Pro Gly Pro Pro Gly Pro Pro Gly Pro Pro Gly Pro
1               5                   10                  15

Pro Gly Pro Pro Gly
            20

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 31

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
```

```
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 32

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 33

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
```

```
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 34

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 35

Pro Pro Gly Pro Pro Gly Pro Pro Gly Pro Pro Gly Cys Pro Gly Pro
1               5                   10                  15

Pro Gly Pro Pro Gly
            20

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
```

```
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 36

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 37

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 38
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 38

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline

<400> SEQUENCE: 39

Pro Pro Gly Pro Pro Gly Pro Pro Gly Pro Pro Gly Pro Pro Gly Pro
1               5                   10                  15

Pro Gly Cys Pro Gly
            20
```

```
<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 40

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
```

```
<221> NAME/KEY: MOD_RES
<222> LOCATION: (20)..(20)
<223> OTHER INFORMATION: Hydroxyproline

<400> SEQUENCE: 41

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 42

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
```

```
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 43

Pro Pro Gly Cys Pro Gly Pro Pro Gly Pro Pro Gly Pro Pro Gly Pro
1               5                   10                  15

Pro Gly Pro Pro Gly
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 44

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
```

<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 45

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 46

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 47

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 48

Pro Pro Gly Pro Pro Gly Pro Pro Gly Pro Pro Gly Cys Pro Gly Pro
1               5                   10                  15

Pro Gly Pro Pro Gly
            20
```

```
<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 49

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 50
```

Pro Pro Gly Pro Pro Gly Pro Pro Gly Pro Pro Gly Pro Pro Gly Cys
1               5                   10                  15

Pro Gly Pro Pro Gly
        20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 51

Pro Pro Gly Pro Pro Gly Pro Pro Gly Pro Pro Gly Pro Pro Gly Pro
1               5                   10                  15

Cys Gly Pro Pro Gly
        20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline

```
<220> FEATURE:
<221> NAME/KEY: MOD_RES
<222> LOCATION: (20)..(20)
<223> OTHER INFORMATION: Hydroxyproline

<400> SEQUENCE: 52

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline

<400> SEQUENCE: 53

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
```

```
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 54

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 55
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 55

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
```

```
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 56

Pro Pro Gly Cys Pro Gly Pro Pro Gly Pro Pro Gly Pro Pro Gly Pro
1               5                   10                  15

Pro Gly Pro Pro Gly
            20

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 57

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

```
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 58

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 59

Pro Pro Gly Pro Pro Gly Pro Pro Gly Cys Pro Gly Pro Pro Gly Pro
1               5                   10                  15

Pro Gly Pro Pro Gly
            20
```

```
<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 60

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 61
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 61
```

Pro Pro Gly Pro Pro Gly Pro Pro Gly Pro Pro Gly Cys Pro Gly Pro
1               5                   10                  15

Pro Gly Pro Pro Gly
            20

<210> SEQ ID NO 62
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 62

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)

```
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 63

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 64

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
```

```
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 65

Pro Pro Gly Pro Pro Gly Pro Pro Gly Pro Pro Gly Pro Pro Gly
1               5                   10                  15

Pro Gly Cys Pro Gly
            20

<210> SEQ ID NO 66
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

<400> SEQUENCE: 66

Pro Pro Gly Pro Pro Gly Pro Pro Gly Pro Pro Gly Pro Pro Gly
1               5                   10                  15

Pro Gly Pro Cys Gly
            20

<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
```

```
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 67

Cys Pro Gly Pro Pro Gly Pro Pro Gly Pro Pro Gly Pro Pro Gly Pro
1               5                   10                  15
Pro Gly Pro Pro Gly
            20

<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 68

Pro Cys Gly Pro Pro Gly Pro Pro Gly Pro Pro Gly Pro Pro Gly Pro
1               5                   10                  15
Pro Gly Pro Pro Gly
            20

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 69

Pro Pro Gly Cys Pro Gly Pro Pro Gly Pro Pro Gly Pro Pro Gly Pro
1               5                   10                  15

Pro Gly Pro Pro Gly
            20

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 70

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 71
<211> LENGTH: 21

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 71

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 72
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 72

Pro Pro Gly Pro Pro Gly Pro Cys Gly Pro Pro Gly Pro Pro Gly Pro
1               5                   10                  15
```

```
Pro Gly Pro Pro Gly
            20

<210> SEQ ID NO 73
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 73

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 74
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
```

```
<222> LOCATION: (20)..(20)
<223> OTHER INFORMATION: Fluoroproline

<400> SEQUENCE: 74

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 75
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 75

Pro Pro Gly Pro Pro Gly Pro Pro Gly Pro Gly Cys Pro Gly Pro
1               5                   10                  15

Pro Gly Pro Pro Gly
            20

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
```

```
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 76

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 77
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 77

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
```

```
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 78

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 79

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 80
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

<400> SEQUENCE: 80

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
```

```
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 81

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
```

```
<221> NAME/KEY: MOD_RES
<222> LOCATION: (20)..(20)
<223> OTHER INFORMATION: Hydroxyproline

<400> SEQUENCE: 82

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 83

Pro Pro Gly Cys Pro Gly Pro Pro Gly Pro Pro Gly Pro Pro Gly Pro
1               5                   10                  15

Pro Gly Pro Pro Gly
```

```
<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 84

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 85

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
```

```
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 86

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 87
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
```

```
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 87

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 88
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
```

```
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 88

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 89
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
```

```
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 89

Pro Pro Gly Pro Pro Gly Pro Pro Gly Pro Pro Gly Cys Pro Gly Pro
1               5                   10                  15

Pro Gly Pro Pro Gly
            20

<210> SEQ ID NO 90
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
```

<222> LOCATION: (20)..(20)
<223> OTHER INFORMATION: Hydroxyproline

<400> SEQUENCE: 90

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 91

Pro Pro Gly Pro Pro Gly Pro Pro Gly Pro Pro Gly Pro Pro Gly Cys
1               5                   10                  15

Pro Gly Pro Pro Gly
            20

```
<210> SEQ ID NO 92
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 92

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 93

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 94
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
```

```
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline

<400> SEQUENCE: 94

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
```

```
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 95

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 96

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
```

<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 97

Pro Pro Gly Cys Pro Gly Pro Pro Gly Pro Pro Gly Pro Pro Gly Pro
1               5                   10                  15

Pro Gly Pro Pro Gly
            20

<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 98

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)

```
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 99

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 100

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 101
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 101

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 102
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 102

Pro Pro Gly Pro Pro Gly Pro Pro Gly Pro Pro Gly Cys Pro Gly Pro
1               5                   10                  15
```

Pro Gly Pro Pro Gly
        20

<210> SEQ ID NO 103
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 103

Pro Pro Gly Pro Pro Gly Pro Pro Gly Pro Pro Gly Pro Cys Gly Pro
1               5                   10                  15

Pro Gly Pro Pro Gly
        20

<210> SEQ ID NO 104
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)

```
<223> OTHER INFORMATION: Chloroproline

<400> SEQUENCE: 104

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 105
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 105

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 106
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
```

-continued

```
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 106

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 107
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline

<400> SEQUENCE: 107

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 108
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
```

```
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 108

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 109
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 109

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 110
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
```

<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 110

Pro Pro Gly Cys Pro Gly Pro Pro Gly Pro Pro Gly Pro Pro Gly Pro
1               5                   10                  15

Pro Gly Pro Pro Gly
            20

<210> SEQ ID NO 111
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 111

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 112
<211> LENGTH: 21
<212> TYPE: PRT
<213> ORGANISM: Artificial Sequence
<220> FEATURE:
<223> OTHER INFORMATION: Description of Artificial Sequence: Synthetic

```
          peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 112

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 113
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 113

Pro Pro Gly Pro Pro Gly Pro Cys Gly Pro Pro Gly Pro Pro Gly Pro
1               5                   10                  15

Pro Gly Pro Pro Gly
            20
```

```
<210> SEQ ID NO 114
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 114

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 115
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 115
```

```
Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 116
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 116

Pro Pro Gly Pro Pro Gly Pro Pro Gly Pro Gly Cys Pro Gly Pro
1               5                   10                  15

Pro Gly Pro Pro Gly
            20

<210> SEQ ID NO 117
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
```

```
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 117

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 118
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 118

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 119
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
```

-continued

```
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 119

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 120
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 120

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 121
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
```

```
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline

<400> SEQUENCE: 121

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 122
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
```

```
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 122

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 123
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline
```

```
<400> SEQUENCE: 123

Pro Cys Gly Pro Pro Gly Pro Gly Pro Pro Gly Pro Pro Gly Pro
1               5                   10                  15

Pro Gly Pro Pro Gly
            20

<210> SEQ ID NO 124
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 124

Pro Pro Gly Cys Pro Gly Pro Pro Gly Pro Pro Gly Pro Pro Gly
1               5                   10                  15

Pro Gly Pro Pro Gly
            20

<210> SEQ ID NO 125
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 125

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 126
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
```

-continued

```
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 126

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 127
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
```

```
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 127

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 128
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
```

```
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 128

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 129
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
```

```
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 129

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 130
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
```

```
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 130

Pro Pro Gly Pro Pro Gly Pro Pro Gly Pro Pro Gly Cys Pro Gly Pro
1               5                   10                  15

Pro Gly Pro Pro Gly
            20

<210> SEQ ID NO 131
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 131
```

Pro Pro Gly Pro Pro Gly Pro Pro Gly Pro Pro Gly Pro Cys Gly Pro
1               5                  10                  15

Pro Gly Pro Pro Gly
            20

<210> SEQ ID NO 132
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 132

Pro Pro Gly Pro Pro Gly Pro Pro Gly Pro Pro Gly Pro Pro Gly Cys
1               5                  10                  15

Pro Gly Pro Pro Gly
            20

<210> SEQ ID NO 133
<211> LENGTH: 21

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 133

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 134
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
```

```
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 134

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 135
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
```

<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline

<400> SEQUENCE: 135

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 136
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 137
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline

```
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 137

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 138
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 138

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 139
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
```

```
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 139

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 140
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 140

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 141
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141
```

```
Met Pro Gly Pro Pro Gly Pro Pro Gly Pro Pro Gly Pro Pro Gly Pro
1               5                   10                  15

Pro Gly Pro Pro Gly
            20

<210> SEQ ID NO 142
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 143
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 145
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 146
<211> LENGTH: 21
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 146

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 147
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 148
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 149
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 150
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Pro Pro Gly Pro Pro Gly Pro Pro Gly Pro Pro Gly Pro Pro Gly Met
1               5                   10                  15

Pro Gly Pro Pro Gly

```
<210> SEQ ID NO 151
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 152
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 153
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 154
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
```

<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 154

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 155
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 155

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 156
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)

<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 156

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 157
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 157

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 158
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline

```
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 158

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 159
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 159

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 160
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 160

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 161
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 161

Pro Pro Gly Pro Pro Gly Pro Pro Gly Pro Pro Gly Met Pro Gly Pro
1               5                   10                  15

Pro Gly Pro Pro Gly
```

<210> SEQ ID NO 162
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 162

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 163
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 163

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 164
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 164

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 165
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:

```
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline

<400> SEQUENCE: 165

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 166
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 166

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 167
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
```

<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 167

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 168
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 168

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 169
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)

```
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 169

Pro Pro Gly Met Pro Gly Pro Pro Gly Pro Pro Gly Pro Pro Gly Pro
1               5                   10                  15
Pro Gly Pro Pro Gly
            20

<210> SEQ ID NO 170
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 170

Pro Pro Gly Pro Met Gly Pro Pro Gly Pro Pro Gly Pro Pro Gly Pro
1               5                   10                  15
Pro Gly Pro Pro Gly
            20

<210> SEQ ID NO 171
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 171

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 172
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 172
```

Pro Pro Gly Pro Pro Gly Pro Pro Gly Met Pro Gly Pro Pro Gly Pro
1               5                   10                  15

Pro Gly Pro Pro Gly
        20

<210> SEQ ID NO 173
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 173

Pro Pro Gly Pro Pro Gly Pro Pro Gly Pro Met Gly Pro Pro Gly Pro
1               5                   10                  15

Pro Gly Pro Pro Gly
        20

<210> SEQ ID NO 174
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)

<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 174

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 175
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 175

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 176
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline

```
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 176

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 177
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 177

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 178
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
```

```
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 178

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 179
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline

<400> SEQUENCE: 179

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 180
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 180

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 181
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 181

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 182
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 182

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 183
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 183

Pro Pro Gly Pro Met Gly Pro Pro Gly Pro Pro Gly Pro Pro Gly Pro
1               5                   10                  15
```

```
Pro Gly Pro Pro Gly
        20

<210> SEQ ID NO 184
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 184

Pro Pro Gly Pro Pro Gly Met Pro Gly Pro Pro Gly Pro Pro Gly Pro
1               5                   10                  15

Pro Gly Pro Pro Gly
        20

<210> SEQ ID NO 185
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
```

```
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 185

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 186
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 186

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 187
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
```

```
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 187

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 188
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 188

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 189
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
```

<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 189

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 190
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 190

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 191
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 191

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 192
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

<400> SEQUENCE: 192

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 193
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 193

Met Pro Gly Pro Pro Gly Pro Pro Gly Pro Pro Gly Pro Pro Gly Pro
 1               5                  10                  15

Pro Gly Pro Pro Gly
            20

<210> SEQ ID NO 194
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 194

Pro Met Gly Pro Pro Gly Pro Pro Gly Pro Pro Gly Pro Pro Gly Pro
```

Pro Gly Pro Pro Gly
        20

<210> SEQ ID NO 195
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 195

Pro Pro Gly Met Pro Gly Pro Pro Gly Pro Pro Gly Pro Pro Gly Pro
1               5                   10                  15

Pro Gly Pro Pro Gly
        20

<210> SEQ ID NO 196
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:

```
<221> NAME/KEY: MOD_RES
<222> LOCATION: (20)..(20)
<223> OTHER INFORMATION: Fluoroproline

<400> SEQUENCE: 196

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 197
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 197

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 198
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
```

```
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 198

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 199
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 199

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 200
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
```

```
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 200

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 201
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 201

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 202
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 202

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 203
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 203

Pro Pro Gly Pro Pro Gly Pro Pro Gly Pro Pro Gly Pro Pro Gly Met
1               5                   10                  15

Pro Gly Pro Pro Gly
            20
```

```
<210> SEQ ID NO 204
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 204

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 205
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 205
```

```
Pro Pro Gly Pro Pro Gly Pro Pro Gly Pro Pro Gly Pro Pro Gly Pro
1               5                   10                  15

Pro Gly Met Pro Gly
            20

<210> SEQ ID NO 206
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

<400> SEQUENCE: 206

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 207
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
```

```
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 207

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 208
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
```

-continued

```
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 208

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 209
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
```

```
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 209

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 210
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 210
```

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 211
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 211

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 212
<211> LENGTH: 21

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 212

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 213
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:

```
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 213

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 214
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
```

```
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 214

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 215
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
```

```
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 215

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 216
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
```

<223> OTHER INFORMATION: Fluoroproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 216

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 217
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:

```
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 217

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 218
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 218
```

```
Pro Pro Gly Pro Pro Gly Pro Pro Gly Pro Pro Gly Pro Pro Gly Pro
1               5                   10                  15

Met Gly Pro Pro Gly
            20

<210> SEQ ID NO 219
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 219

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 220
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline

<400> SEQUENCE: 220

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 221
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
```

```
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 221

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 222
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 222

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 223
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 223

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 224
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 224

Pro Pro Gly Pro Met Gly Pro Pro Gly Pro Pro Gly Pro Pro Gly Pro
1               5                   10                  15

Pro Gly Pro Pro Gly
            20
```

```
<210> SEQ ID NO 225
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 225

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 226
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
```

<222> LOCATION: (20)..(20)
<223> OTHER INFORMATION: Chloroproline

<400> SEQUENCE: 226

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 227
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 227

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 228
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)

<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 228

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 229
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 229

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 230
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline

```
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 230

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 231
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 231

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 232
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
```

<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 232

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 233
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline

<400> SEQUENCE: 233

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 234
<211> LENGTH: 21
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 234

Met Pro Gly Pro Pro Gly Pro Pro Gly Pro Pro Gly Pro Pro Gly Pro
 1               5                  10                  15

Pro Gly Pro Pro Gly
            20

<210> SEQ ID NO 235
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 235

Pro Met Gly Pro Pro Gly Pro Pro Gly Pro Pro Gly Pro Pro Gly Pro
 1               5                  10                  15

Pro Gly Pro Pro Gly
            20
```

```
<210> SEQ ID NO 236
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 236

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 237
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline
```

-continued

```
<400> SEQUENCE: 237

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 238
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 238

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 239
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
```

```
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 239

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 240
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 240

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 241
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
```

<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 241

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 242
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 242

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 243
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline

```
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 243

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 244
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 244

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 245
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 245

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 246
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 246

Pro Pro Gly Pro Pro Gly Pro Pro Gly Pro Pro Gly Pro Pro Gly Pro
1               5                   10                  15

Pro Gly Met Pro Gly
```

20

<210> SEQ ID NO 247
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline

<400> SEQUENCE: 247

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 248
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline

```
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 248

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 249
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
```

```
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 249

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 250
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
```

<220> FEATURE:
<221> NAME/KEY: MOD_RES
<222> LOCATION: (20)..(20)
<223> OTHER INFORMATION: Hydroxyproline

<400> SEQUENCE: 250

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 251
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 251

Pro Pro Gly Pro Met Gly Pro Pro Gly Pro Pro Gly Pro Pro Gly Pro
1               5                   10                  15

Pro Gly Pro Pro Gly
        20

<210> SEQ ID NO 252
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 252

Pro Pro Gly Pro Pro Gly Met Pro Gly Pro Gly Pro Pro Gly Pro
1               5                   10                  15

Pro Gly Pro Pro Gly
        20

<210> SEQ ID NO 253
<211> LENGTH: 21
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 253

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 254
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
```

```
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 254

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 255
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
```

```
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 255

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 256
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
```

```
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 256

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 257
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (16)..(16)
```

```
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 257

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 258
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
```

<221> NAME/KEY: MOD_RES
<222> LOCATION: (20)..(20)
<223> OTHER INFORMATION: Hydroxyproline

<400> SEQUENCE: 258

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 259
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 259

Pro Pro Gly Pro Pro Gly Pro Pro Gly Pro Pro Gly Pro Pro Gly Pro
1               5                   10                  15

Met Gly Pro Pro Gly

```
<210> SEQ ID NO 260
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 260

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 261
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline

<400> SEQUENCE: 261

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 262
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Pro Pro Gly Pro Pro Gly Lys Pro Gly Pro Pro Gly Pro Pro Gly Pro
1               5                   10                  15

Pro Gly Pro Pro Gly
            20
```

```
<210> SEQ ID NO 263
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 263

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 264
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 264

Pro Pro Gly Pro Pro Gly Pro Lys Gly Pro Pro Gly Pro Pro Gly Pro
1               5                   10                  15

Pro Gly Pro Pro Gly
```

<210> SEQ ID NO 265
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 265

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 266
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 266

Pro Pro Gly Pro Pro Gly Pro Lys Gly Pro Pro Gly Pro Pro Gly Pro

```
                1               5                   10                  15
Pro Gly Pro Pro Gly
            20

<210> SEQ ID NO 267
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 268
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 269
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 270
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 271
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 271

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 272
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 273
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 274
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 275
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Pro Pro Gly Pro Pro Gly Pro Pro Gly Pro Pro Gly Pro Lys Gly Pro
1               5                   10                  15

Pro Gly Pro Pro Gly
            20
```

<210> SEQ ID NO 276
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 277
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 278
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 279
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 280
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)

```
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 280

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 281
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 281

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 282
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 282

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 283
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 283

Pro Pro Gly Pro Lys Gly Pro Pro Gly Pro Pro Gly Pro Pro Gly Pro
1               5                   10                  15
```

Pro Gly Pro Pro Gly
        20

<210> SEQ ID NO 284
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 284

Pro Pro Gly Pro Pro Gly Pro Lys Gly Pro Pro Gly Pro Pro Gly Pro
1               5                   10                  15

Pro Gly Pro Pro Gly
        20

<210> SEQ ID NO 285
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)

<223> OTHER INFORMATION: Hydroxyproline

<400> SEQUENCE: 285

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 286
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 286

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 287
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline

```
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 287

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 288
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 288

Pro Pro Gly Pro Pro Gly Pro Pro Gly Pro Pro Gly Pro Lys Gly Pro
1               5                   10                  15

Pro Gly Pro Pro Gly
            20

<210> SEQ ID NO 289
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
```

```
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 289

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 290
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 290

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 291
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline

<400> SEQUENCE: 291

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 292
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 292

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 293
<211> LENGTH: 21

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 293

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 294
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 294

Pro Lys Gly Pro Pro Gly Pro Pro Gly Pro Pro Gly Pro Pro Gly Pro
1               5                   10                  15
```

Pro Gly Pro Pro Gly
            20

<210> SEQ ID NO 295
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 295

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 296
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 296

Pro Pro Gly Pro Lys Gly Pro Pro Gly Pro Gly Pro Pro Gly Pro
1               5                   10                  15

Pro Gly Pro Pro Gly
            20

<210> SEQ ID NO 297
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 297

Pro Pro Gly Pro Pro Gly Lys Pro Gly Pro Gly Pro Pro Gly Pro
1               5                   10                  15

Pro Gly Pro Pro Gly
            20

<210> SEQ ID NO 298
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)

```
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 298

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 299
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 299

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 300
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
```

```
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 300

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 301
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 301

Pro Pro Gly Pro Pro Gly Pro Pro Gly Pro Pro Gly Pro Lys Gly Pro
1               5                   10                  15

Pro Gly Pro Pro Gly
            20

<210> SEQ ID NO 302
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 302

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 303
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 303

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 304
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 304

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 305
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline

<400> SEQUENCE: 305

Pro Pro Gly Pro Pro Gly Pro Pro Gly Pro Pro Gly Pro Pro Gly Pro
```

Pro Gly Pro Lys Gly
            20

<210> SEQ ID NO 306
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 306

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 307
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:

```
<221> NAME/KEY: MOD_RES
<222> LOCATION: (20)..(20)
<223> OTHER INFORMATION: Fluoroproline

<400> SEQUENCE: 307

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 308
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 308

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 309
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
```

```
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 309

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 310
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 310

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 311
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
```

<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 311

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 312
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 312

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 313
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 313

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 314
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 314

Pro Pro Gly Pro Pro Gly Pro Pro Gly Pro Pro Gly Pro Lys Gly Pro
1               5                   10                  15

Pro Gly Pro Pro Gly
            20
```

```
<210> SEQ ID NO 315
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 315

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 316
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 316
```

```
Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 317
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 317

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 318
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
```

```
<220> FEATURE:
<221> NAME/KEY: MOD_RES
<222> LOCATION: (17)..(17)
<223> OTHER INFORMATION: Fluoroproline

<400> SEQUENCE: 318

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 319
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 319

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 320
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
```

<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 320

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 321
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 321

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 322
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 322

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 323
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 323

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 324
<211> LENGTH: 21
<212> TYPE: PRT
<213> ORGANISM: Artificial Sequence
<220> FEATURE:
<223> OTHER INFORMATION: Description of Artificial Sequence: Synthetic -continued

```
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 324

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 325
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 325

Pro Pro Gly Pro Pro Gly Pro Pro Gly Lys Pro Gly Pro Pro Gly Pro
1               5                   10                  15

Pro Gly Pro Pro Gly
            20
```

```
<210> SEQ ID NO 326
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 326

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 327
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 327
```

Pro Pro Gly Pro Pro Gly Pro Pro Gly Pro Pro Gly Lys Pro Gly Pro
1               5                  10                 15

Pro Gly Pro Pro Gly
         20

<210> SEQ ID NO 328
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 328

Pro Pro Gly Pro Pro Gly Pro Pro Gly Pro Pro Gly Pro Lys Gly Pro
1               5                  10                 15

Pro Gly Pro Pro Gly
         20

<210> SEQ ID NO 329
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)

<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 329

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 330
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 330

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 331
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline

```
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 331

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 332
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

<400> SEQUENCE: 332

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 333
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
```

<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 333

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 334
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)

```
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 334

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 335
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
```

-continued

```
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 335

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 336
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
```

```
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 336

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 337
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
```

```
<221> NAME/KEY: MOD_RES
<222> LOCATION: (20)..(20)
<223> OTHER INFORMATION: Hydroxyproline

<400> SEQUENCE: 337

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 338
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 338

Pro Pro Gly Pro Pro Gly Pro Lys Gly Pro Pro Gly Pro Pro Gly Pro
1               5                   10                  15

Pro Gly Pro Pro Gly
```

<210> SEQ ID NO 339
<211> LENGTH: 21
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 339

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 340
<211> LENGTH: 21
<212> TYPE: PRT
<213> ORGANISM: Artificial Sequence
<220> FEATURE:
<223> OTHER INFORMATION: Description of Artificial Sequence: Synthetic
    peptide

```
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 340

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 341
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
```

```
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 341

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 342
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
```

```
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 342

Pro Pro Gly Pro Pro Gly Pro Pro Gly Pro Pro Gly Pro Lys Gly Pro
1               5                   10                  15

Pro Gly Pro Pro Gly
            20

<210> SEQ ID NO 343
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
```

```
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 343

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 344
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
```

```
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 344

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 345
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
```

```
<222> LOCATION: (20)..(20)
<223> OTHER INFORMATION: Hydroxyproline

<400> SEQUENCE: 345

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 346
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline

<400> SEQUENCE: 346

Pro Pro Gly Pro Pro Gly Pro Pro Gly Pro Pro Gly Pro Pro Gly Pro
1               5                   10                  15

Pro Gly Pro Lys Gly
            20
```

```
<210> SEQ ID NO 347
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 347

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 348
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline
```

-continued

```
<400> SEQUENCE: 348

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 349
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 349

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 350
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
```

```
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 350

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 351
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 351

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 352
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
```

```
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 352

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 353
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 353

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 354
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
```

```
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 354

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 355
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 355

Pro Pro Gly Pro Pro Gly Pro Pro Gly Pro Pro Gly Pro Lys Gly Pro
1               5                   10                  15

Pro Gly Pro Pro Gly
            20

<210> SEQ ID NO 356
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 356

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 357
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 357

Pro Pro Gly Pro Pro Gly Pro Pro Gly Pro Pro Gly Pro Pro Gly Pro
1               5                   10                  15

Lys Gly Pro Pro Gly
```

```
                20

<210> SEQ ID NO 358
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 358

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 359
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
```

```
<400> SEQUENCE: 359

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 360
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 360

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 361
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
```

```
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 361

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 362
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 362

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 363
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
```

<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 363

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 364
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 364

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 365
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)

```
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 365

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 366
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 366

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 367
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 367

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 368
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 368

Pro Pro Gly Pro Pro Gly Pro Pro Gly Pro Pro Gly Lys Pro Gly Pro
1               5                   10                  15
```

Pro Gly Pro Pro Gly
        20

<210> SEQ ID NO 369
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 369

Pro Pro Gly Pro Pro Gly Pro Pro Gly Pro Pro Gly Pro Lys Gly Pro
1               5                   10                  15

Pro Gly Pro Pro Gly
        20

<210> SEQ ID NO 370
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)

<223> OTHER INFORMATION: Chloroproline

<400> SEQUENCE: 370

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 371
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 371

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 372
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline

```
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 372

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 373
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline

<400> SEQUENCE: 373

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 374
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
```

```
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 374

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 375
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
```

```
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 375

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 376
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
```

```
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 376

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 377
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
```

```
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 377

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 378
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline
```

-continued

<400> SEQUENCE: 378

Pro Pro Gly Pro Pro Gly Lys Pro Gly Pro Pro Gly Pro Gly Pro
1               5                   10                  15

Pro Gly Pro Pro Gly
            20

<210> SEQ ID NO 379
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 379

Pro Pro Gly Pro Pro Gly Pro Lys Gly Pro Pro Gly Pro Gly Pro
1               5                   10                  15

Pro Gly Pro Pro Gly
            20

<210> SEQ ID NO 380

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 380

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 381
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
```

```
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 381

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 382
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
```

```
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 382

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 383
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
```

```
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 383

Pro Pro Gly Pro Pro Gly Pro Pro Gly Pro Pro Gly Pro Lys Gly Pro
1               5                   10                  15

Pro Gly Pro Pro Gly
            20

<210> SEQ ID NO 384
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
```

```
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 384

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 385
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
```

```
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 385

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 386
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 386
```

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 387
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline

<400> SEQUENCE: 387

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 388
<211> LENGTH: 11

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Arg Pro Lys Pro Gln Gln Phe Phe Gly Leu Met
1               5                   10

<210> SEQ ID NO 389
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
            20                  25                  30

<210> SEQ ID NO 390
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 390

Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
            20                  25                  30

<210> SEQ ID NO 391
<211> LENGTH: 32
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 391

Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
            20                  25                  30

<210> SEQ ID NO 392
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline

```
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 392

Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
            20                  25                  30

<210> SEQ ID NO 393
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
```

```
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 393

Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
            20                  25                  30

<210> SEQ ID NO 394
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 394

Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
            20                  25                  30

<210> SEQ ID NO 395
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 395

Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
            20                  25                  30

<210> SEQ ID NO 396
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline
```

<220> FEATURE:
<221> NAME/KEY: MOD_RES
<222> LOCATION: (23)..(23)
<223> OTHER INFORMATION: Hydroxyproline
<220> FEATURE:
<221> NAME/KEY: MOD_RES
<222> LOCATION: (26)..(26)
<223> OTHER INFORMATION: Hydroxyproline
<220> FEATURE:
<221> NAME/KEY: MOD_RES
<222> LOCATION: (29)..(29)
<223> OTHER INFORMATION: Hydroxyproline

<400> SEQUENCE: 396

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly
            20                  25                  30

<210> SEQ ID NO 397
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly
            20                  25                  30

<210> SEQ ID NO 398
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (2)..(2)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (4)..(4)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (5)..(5)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (7)..(7)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (8)..(8)
<223> OTHER INFORMATION: Pro, 4R-hydroxyproline, fluoroproline,
      chloroproline, Lys, Cys or Met -continued

```
<220> FEATURE:
<221> NAME/KEY: MOD_RES
<222> LOCATION: (10)..(10)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (11)..(11)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (13)..(13)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (14)..(14)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (16)..(16)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (17)..(17)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (19)..(19)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (20)..(20)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (22)..(22)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (23)..(23)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (25)..(25)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (26)..(26)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (28)..(28)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (29)..(29)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (31)..(31)
<223> OTHER INFORMATION: Pro, 4S-hydroxyproline, fluoroproline,
      chloroproline, Lys, Cys or Met
```

```
<220> FEATURE:
<221> NAME/KEY: MOD_RES
<222> LOCATION: (32)..(32)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (34)..(34)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (35)..(35)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (37)..(37)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (38)..(38)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (40)..(40)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (41)..(41)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (43)..(43)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (44)..(44)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (46)..(46)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (47)..(47)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (49)..(49)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (50)..(50)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (52)..(52)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (53)..(53)
<223> OTHER INFORMATION: Pro, 4R-hydroxyproline, fluoroproline,
      chloroproline, Lys, Cys or Met
```

```
<220> FEATURE:
<221> NAME/KEY: MOD_RES
<222> LOCATION: (55)..(55)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (56)..(56)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (58)..(58)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (59)..(59)
<223> OTHER INFORMATION: Pro, 4R-hydroxyproline, fluoroproline,
      chloroproline, Lys, Cys or Met
<220> FEATURE:
<221> NAME/KEY: MISC_FEATURE
<222> LOCATION: (1)..(60)
<223> OTHER INFORMATION: This sequence may encompass 1-20 "Xaa Xaa Gly"
      repeating units wherein Xaa is Pro, 4S-hydroxyproline,
      4R-hydroxyproline, fluoroproline, chloroproline, Lys, Cys or Met
<220> FEATURE:
<223> OTHER INFORMATION: See specification as filed for detailed
      description of substitutions and preferred embodiments

<400> SEQUENCE: 398

Xaa Xaa Gly Xaa Xaa Gly Xaa Xaa Gly Xaa Xaa Gly Xaa Xaa Gly Xaa
1               5                   10                  15

Xaa Gly Xaa Xaa Gly Xaa Xaa Gly Xaa Xaa Gly Xaa Xaa Gly Xaa Xaa
            20                  25                  30

Gly Xaa Xaa Gly Xaa Xaa Gly Xaa Xaa Gly Xaa Xaa Gly Xaa Xaa Gly
        35                  40                  45

Xaa Xaa Gly Xaa Xaa Gly Xaa Xaa Gly Xaa Xaa Gly
50                  55                  60
```

COLLAGEN PEPTIDE-BASED MEDICAMENT COMPOSITIONS AND DEVICES AND METHODS OF PRODUCTION AND USE THEREOF

CROSS-REFERENCE TO RELATED APPLICATIONS AND INCORPORATION BY REFERENCE

The present application claims the benefit of U.S. Provisional Patent Application Nos. 62/482,592, filed on Apr. 6, 2017, and 62/581,927, filed Nov. 6, 2017, both entitled "Collagen-Based Medicament Compositions and Devices and Methods of Production and Use Thereof" and naming as inventors Eric Schlumpf, Robert Baratta and Shawn A. DeLorey. The contents of these applications are incorporated herein by reference in their entireties.

STATEMENT REGARDING FEDERALLY-SPONSORED RESEARCH AND DEVELOPMENT

Not applicable.

NAMES OF THE PARTIES TO A JOINT RESEARCH AGREEMENT

Not applicable.

REFERENCE TO SEQUENCE LISTING SUBMITTED ELECTRONICALLY

The contents of the electronic sequence listing (0123-0001US1_SL.txt; Size: 314 KB; and Date of Creation Jul. 5, 2018) submitted herewith, is herein incorporated by reference in its entirety.

STATEMENT REGARDING PRIOR DISCLOSURES BY THE INVENTOR OR A JOINT INVENTOR

Some of the material disclosed herein was disclosed and claimed in U.S. Provisional Patent Application Nos. 62/482,592, filed Apr. 6, 2017, and 62/581,927, filed Nov. 6, 2017, both entitled "Collagen-Based Medicament Compositions and Devices and Methods of Production and Use Thereof", and naming as inventors Eric Schlumpf, Robert Baratta and Shawn A. DeLorey.

BACKGROUND OF THE INVENTION

Field of the Invention

The present invention is in the fields of medicinal chemistry, biotechnology, pharmaceuticals and medical devices, as well as the use of medicinal compounds and medical devices for the treatment, prevention and amelioration of diseases, disorders and physical ailments in humans and veterinary animals.

Background Art

Collagen is the most abundant protein in vertebrates, and is the fundamental structural protein for vertebrate tissues, occurring in virtually every tissue including skin and other epithelial tissues (including the lining of most luminal organs such as those of the gastrointestinal tract), tendons, bone, blood vessels, cartilage, ligaments and teeth. In humans, collagen makes up about a third of the total protein and about three-quarters of the dry weight of skin (see Shoulders, M. D., and Raines, R. T., Ann. Rev. Biochem. 78:929-958 (2009); Gelse, K., et al., Adv. Drug Deliv. Rev. 55:1531-1546 (2003)).

Collagen is a fibrous protein that is composed of a triple helix, which generally consists of two identical chains and a third chain that differs slightly in its chemical composition. Mammals produce at least 46 distinct collagen polypeptide chains that combine to form variants or "types" of collagen. To date, 28 types of collagen have been described. Collagen types are generally grouped according to their structural forms: fibrillar (types I, II, III, V and XI) which represent about 90% of all collagen protein found in mammals, and non-fibrillar (basement membrane or type IV, and other non-fibrillar collagen types with interrupted helix structures) see Id.). The five most common types of collagen, and their tissue distributions, are:

Type I: skin, tendon, organs, bone, vascular connective tissue;
Type II: cartilage;
Type III: reticular connective tissue, often associated with Type I collagen;
Type IV: basement membranes of epithelial tissues and certain solid tumors; and
Type V: hair, placenta, external cellular membranes.

In each of these variants, the polypeptide chains of collagen are composed of approximately 300 repeats of the amino acids proline (Pro), 4(R)-hydroxyproline (Hyp) and glycine (Gly), usually in the sequence X-Y-Gly, where X is often a Pro residue and Y is often a (Hyp) residue; in vertebrates, the typical repeat motif in collagen is ProProGly (see Hulmes, D. J. S., "Collagen Diversity, Synthesis and Assembly," in: Collagen: Structure and Mechanics, P. Fratzl, Ed., New York: Springer, pp. 15-47 (2008)). Subsequently, in vivo, the hydroxylation of Pro residues is performed enzymatically after collagen biosynthesis but before the chains begin to form a triple helix. Thus, hydroxylation of at least one Pro residue in the ProProGly motif, typically forming ProHypGly, appears to be important for both the proper folding and stability of the collagen triple helix, both of which are key to the normal structure and function of collagen in vivo (see Shoulders, M. D., and Raines, R. T., Ann. Rev. Biochem. 78:929-958 (2009)). For example, the melting temperature of a triple helix of $(ProHypGly)_{10}$ (SEQ ID NO: 396) chains is 58° C., while that of a triple helix of $(ProProGly)10$ (SEQ ID NO: 397) chains is only 24° C. (Sakakibara et al., Biochim. Biophys. Acta, 303:198-202 (1973)), and the rate at which $(ProHypGly)_{10}$ (SEQ ID NO: 396) chains fold into a triple helix is substantially greater than the corresponding rate for $(ProProGly)_{10}$ (SEQ ID NO: 397) chains (Chopra and Ananthanarayanan, Proc. Natl. Acad. Sci. USA, 79:7180-7184 (1982)).

Type I collagen is the most abundant and best-studied collagen. In humans and most other animals it forms more than 90% of the organic mass of bone and is the major collagen of tendons, skin, ligaments, cornea, and many interstitial connective tissues with the exception of a very few such as hyaline cartilage, brain and the vitreous body. The collagen type I triple helix is usually formed as a heterotrimer by two identical α1 chains and one α2 chain. The triple helical fibers are, in vivo, primarily incorporated into composite fibrils containing other types of collagens, which as noted above vary depending upon tissue type and location (Fleischmajer, E. D. et al., J. Struct. Biol. 105: 162-169 (1990); Niyibizi, C. and Eyre, D. R., Connect.

Tissue Res. 20: 247-250 (1989)). In most organs and notably in tendons and fascia, type I collagen provides tensile rigidity and in bone, it defines the biomechanical properties relating to load bearing, tensile strength and torsional stiffness.

In connective tissues (such as bone, tendon, cartilage, ligament, skin, blood vessels and teeth), individual collagen molecules are wound together in tight triple helices. These helices are organized into fibrils of great tensile strength (Jones & Miller, J. Mol. Biol., 218:209-219 (1991)) via cross-linking of individual triple helix fibers (Lodish, H. et al., "Collagen: The Fibrous Proteins of the Matrix", in: Molecular Cell Biology, 4th ed., Section 22.3, New York: W. H. Freeman (2000)). Varying the arrangements and cross linking of the collagen fibrils enables vertebrates to support stress in one dimension (tendons), two dimensions (skin) or three dimensions (cartilage).

Collagens serve within the body to a considerable extent for the maintenance of the structural integrity of tissues and organs. In all parenchymal organs, collagens represent the major component of the interstitial matrix as well as the basement membranes, while in all connective tissues, particularly bone and cartilage, collagens provide the major functional backbone of the structures. Besides the biomechanical aspects, however, collagens are also involved in a variety of additional functions. For example, specific cell surface and intracellular receptors interact with collagens, and signaling by these receptors is involved in cellular adhesion, differentiation, growth and other cellular activities, as well as the survival of cells both in vivo and in vitro (Vogel, W. F., Eur. J. Dermatol. 11: 506-514 (2001); Gelse, K., et al., Adv. Drug Deliv. Rev. 55:1531-1546 (2003)). Collagens also are involved in the entrapment, local storage and delivery of growth factors and cytokines in a variety of tissues in which the collagens are found. Through these receptor interactions and storage and delivery functions, collagen plays a key role in organ development, wound healing and tissue repair (Chattopadhyay, S. and R. Raines, Biopolymers 101: 821-833 (2014); Yamaguchi, Y. et al., Nature 346: 281-284 (1990); Hay, E. D., J. Cell Biol. 91:205s-223s (1981); Bautista, C. M. et al., Metabolism 39: 96-100 (1990); Zhu, Y. et al., J. Cell Biol. 144: 1069-1080 (1998); Schlegel, K. A. et al., Biomaterials 25:5387-5393 (2004); Kumar, V. A., et al., Biomacromol. 15: 1484-1490 (2014)). These functions also qualify collagens as candidate transport vehicles for the delivery of therapeutic compounds (see, e.g., Chattopadhyay, S. et al., J. Tissue Eng. Regen. Med. 10:1012-1020 (2012); Schuppan, D. et al., Gastroenterol. 114: 139-152 (1998); Frenkel, S. R. et al., J. Bone Jt. Surg. 79-B: 831-836 (1997); Albu, M. G. et al., "Collagen-Based Drug Delivery Systems for Tissue Engineering", in: Biomaterials Applications for Nanomedicine, Pignatello, R. (Ed.), ISBN: 978-953-307-661-4, DOI: 10.5772/22981, Rijeka, Croatia: InTech, available from: intechopen.com/books/biomaterials-applications-for-nanomedicine/collagen-based-drug-delivery-systems-for-tissue-engineering (2011)), and for use in wound healing by directly promoting tissue repair or regeneration (Wakitani, S. et al., J. Bone Jt. Surg. 71-B: 74-80 (1989); Kumar, V. A., et al., Biomacromol. 15: 1484-1490 (2014)). Collagen (more particularly, disrupted collagen) has also been implicated in tumor progression and metastasis in humans and other vertebrates (for a review of this issue, see Fang, M., et al., Tumor Biol. 35:2871-2882 (2014)).

Beyond intact collagen molecules, however, fragments of collagen may also have potential therapeutic uses, and indeed, may perform in a superior fashion relative to native collagen. For example, non-collagenous fragments of collagens IV, XV and XVIII have been shown to promote the growth of blood vessels and tumor cells, and to influence a variety of other cellular activities (Ortega, N. and Werb, Z., J. Cell Sci. 115: 4201-4214 (2002); Davis, G. E. et al., Am. J. Pathol. 156: 1489-1498 (2000); O'Reilly, M. S. et al., Cell 88: 277-285 (1997)). Analogously, as described in greater detail below, fragments or synthetic collagen mimetic peptides (CMPs) of collagen type I have recently been studied for their utility in treatment of diseases and medical disorders, both as active pharmaceutical ingredients (APIs) in their own right and in the delivery of a skin wound-healing agent (see U.S. Pat. Nos. 5,973,112, 7,122,521, 7,858,741, and U.S. Patent Publ. No. US 2007/0275897 A1, the disclosures of all of which are incorporated herein by reference in their entireties; see also e.g., Chattopadhyay, S. et al., J. Tissue Eng. Regen. Med. 10:1012-1020 (2012); Kumar, V. A. et al., Biomacromolecules 15:1484-1490 (2014)).

Collagen abnormalities are associated with a wide variety of human diseases, including diseases and disorders of the eye such as cataracts and glaucoma (Coudrillier, B., et al., PLoS ONE 10: e0131396 (2015); Huang, W. et al., Med. Sci. Monit. Basic Res. 19: 237-240 (2013); Dua, H. S., et al., Br. J. Ophthalmol. 98: 691-697 (2014)), arthritis, rheumatism, brittle bones, atherosclerosis and cirrhosis. Disruptions in collagen are also associated with certain human and veterinary diseases such as certain cancers (particularly carcinomas of the luminal organs, and certain sarcomas); see, e.g., Lauer, J. L., and Fields, G. B., "Collagen in Cancer", in *The Tumor Microenvironment*, New York: Springer, pp. 477-507 (2010). Collagen is also critically important in wound healing and is known to be upregulated in areas of epithelial wounds where healing is taking place (see, e.g., U.S. Pat. Nos. 5,973,112 and 7,122,521, which are incorporated herein by reference in their entireties; see also Chattopadhyay, S., et al., J. Tissue Eng. Regen. Med. 10:1012-1020 (2012); Chattopadhyay, S., et al., Org. Biomol. Chem. 10:5892-5897 (2012); Kumar, V. A., et al., Biomacromol. 15: 1484-1490 (2014)), including in the skin and the cornea of the eye. Indeed, collagen, collagen fragments or certain mimetic peptides of natural collagen have been reported to show promise in treating certain wounds and diseases in humans and animals, particularly skin wounds (see, e.g., U.S. Pat. Nos. 5,973,112, 7,122,521, 7,858,741, and U.S. Patent Publ. No. US 2007/0275897 A1, all of which are incorporated herein by reference in their entireties; see also Kumar, V. A. et al., Biomacromolecules 15:1484-1490 (2014)). It is thought that these collagen fragments or collagen mimetic peptides may specifically target areas of collagen disruption associated with skin wounds by intercalating into the disrupted collagen and reforming the native collagen I triple helix (see, e.g., Chattopadhyay, S., et al., J. Tissue Eng. Regen. Med. 10:1012-1020 (2012); Chattopadhyay, S., et al., Org. Biomol. Chem. 10:5892-5897 (2012)). As a result, there have been attempts made to use collagen as a vehicle for delivering certain drugs, with varying degrees of success (see, e.g., B. An, et al., Adv. Drug Deliv. Rev. 97:69-84 (2016); V. Chak, et al., Intl. J. Pharm. Teaching and Practices 4:811 (2013)). Collagen mimetic peptides have also been used in a topical application to deliver a conjugated therapeutic compound, the neuropeptide known as Substance P, to areas of skin wounds; such CMP-Substance P conjugates have been shown to accelerate wound healing in a mouse skin model (Chattopadhyay, S., et al., J. Tissue Eng. Regen. Med. 10:1012-1020 (2012)).

Treatments for diseases/disorders are expensive, difficult to deliver with specificity, and may have deleterious effects at sites distal to the intended site of action. For example, many medicinal compositions, including antibiotics, small molecule therapeutics (e.g., anti-cancer compounds) and biologics (e.g., monoclonal antibody therapeutics) are administered parenterally in a non-targeted fashion and must diffuse or otherwise find their way to the site of the affliction before they are able to provide their therapeutic benefits. This "shotgun approach" to therapy necessarily requires higher dosing and can result in longer periods of therapy and reduced patient compliance than a therapeutic approach which would deliver therapeutic compounds and compositions in a more targeted fashion which would allow for controlled or programmable release at or near the site of the affliction in a human or veterinary animal.

Thus, there is a need in the art for drug delivery systems—i.e., compositions and methods of use—that will overcome many of these shortcomings in traditional treatments for certain diseases and disorders in humans and veterinary animals. Such advanced drug delivery systems would allow the use of lower doses of medication and more targeted delivery of the medications to the intended sites of action, as well as reducing the therapeutic problems or delays resulting from patient non-compliance. There also is a need for medical devices coated with such compositions which will facilitate more rapid healing and recovery in humans and animals suffering from such diseases and disorders. Finally, there is a need in the art for methods of producing such compositions and medical devices that will meet the needs of the medical and patient communities in maximizing treatment efficacies while reducing costs.

BRIEF SUMMARY OF THE INVENTION

The present inventors reasoned that since collagen disruption is associated with a variety of diseases and disorders in humans and other animals, the conjugation of a variety of therapeutic compounds and/or diagnostic compounds to collagen or collagen mimetic peptides would provide an elegant, rapid and reproducible way of overcoming many of the above-referenced limitations in drug delivery. Thus, the present invention provides such drug delivery systems, medical devices and methods of manufacturing the same. Accordingly, the present invention meets the needs in the art as expressed hereinabove.

In one aspect, the invention provides compositions comprising one or more collagen mimetic peptides (CMPs), which in certain embodiments have been conjugated one or more therapeutic compounds and/or one or more diagnostic compounds thereby forming CMP conjugates and compositions. Such CMPs and CMP conjugates, and compositions comprising such CMPs and/or CMP conjugates, are useful in treating, preventing, ameliorating and diagnosing a variety of diseases, disorders and physical conditions in humans and veterinary animals. In certain embodiments of this aspect, the invention provides compositions comprising such CMPs and/or CMP conjugates and one or more pharmaceutically acceptable carriers, excipients or compounding agents, and optionally one or more additional therapeutic or diagnostic agents, to provide therapeutic and diagnostic compositions useful in treating, preventing, ameliorating or diagnosing certain diseases and disorders in humans and veterinary animals.

In another aspect, the invention provides methods of treating, preventing, ameliorating or diagnosing certain diseases and disorders in humans and veterinary animals, by administering the conjugates and/or compositions of the invention to a human or veterinary animal suffering from or predisposed to such diseases or disorders. Diseases and disorders suitably treated, prevented, cured, ameliorated or diagnoses according to this aspect of the invention include ocular diseases or disorders, skin diseases or disorders, cancers, gastrointestinal diseases or disorders, genitourinary tract diseases or disorders, fibrotic diseases or disorders, cardiovascular diseases or disorders, bone diseases or disorders, and rheumatic diseases or disorders.

In yet another aspect, the invention provides medical devices coated with or comprising one or more of the conjugates or compositions of the invention. In related aspects, the invention provides methods of treating, curing, preventing or ameliorating diseases or disorders in humans or veterinary animals comprising implanting one or more of the medical devices of this aspect of the invention into the human or veterinary animal, under conditions such that the disease or disorder is treated, cured, prevented or ameliorated.

In still other aspects, the invention provides methods of manufacturing the compositions, conjugates and medical devices of the invention.

Other objects, advantages, and features of the present invention will be readily apparent to those of ordinary skill in the art upon review of the description, drawings, examples and claims presented herein.

BRIEF DESCRIPTION OF THE DRAWING

The FIGURE is a series of photomicrographs depicting the healing of a wound in the cornea of mouse eye, at time 0 and 16 hours post-wounding, upon treatment with certain compositions of the present invention. Wounds were introduced into the corneas of mice, and the mice treated immediately after wounding with vehicle (PBS), with 100 ng/mL of epidermal growth factor (EGF), or with 25 nM (about 3 mg/kg) of a (Pro-Pro-Gly)7 CMP of the invention (SEQ ID NO:1) ("Cmpd 3"), or of a (Hyp-Pro-Gly)7-SubP CMP-TC of the invention (SEQ ID NO:390) ("Cmpd 10"). The extent of the remaining corneal abrasion and damage to the underlying corneal stroma was then revealed with fluorescein staining and fluorescence photomicrography of the eyes at time 0 and 16 hours post-wounding.

DETAILED DESCRIPTION OF THE INVENTION

Unless defined otherwise, all technical and scientific terms used herein have the same meanings as commonly understood by one of ordinary skill in the arts to which this invention belongs. Although any methods and materials similar or equivalent to those described herein can be used in the practice or testing of the present invention, the preferred methods and materials are described hereinafter.

According to a first aspect, the invention provides compositions suitable for use in a medicament for treating or preventing a disease or disorder in a human or veterinary animal in need of treatment or prevention of such a disease or disorder. In certain embodiments, the compositions provided by the invention comprise (a) at least one collagen mimetic peptide (CMP) attached to at least one therapeutic compound (TC) to form a CMP-TC conjugate, and (b) one or more pharmaceutically suitable carriers.

In certain embodiments of the invention, the collagen mimetic peptide comprises, consists essentially of or consists of an amino acid sequence that is a multimeric repeat of a specific tripeptide having a sequence (Xaa-Yaa-Gly)$_n$ (SEQ ID NO: 398), wherein Xaa is independently selected from the group consisting of proline, 4S-hydroxyproline, fluoroproline, chloroproline, lysine, cysteine and methionine; wherein Yaa is independently selected from the group consisting of proline, 4R-hydroxyproline, fluoroproline, chloroproline, lysine, cysteine and methionine; wherein Gly is a glycine residue; and wherein n is an integer ranging from 1 to 20, such as from 3 to 15, from 5 to 15, or from 5 to 10, and is preferably 5, 6, 7, 8, 9 or 10.

In certain embodiments of the invention, the collagen mimetic peptide comprises, consists essentially of or consists of an amino acid sequence that is or corresponds to a 21-mer comprising seven repeats of a three amino acid sequence of proline-proline-glycine ((Pro-Pro-Gly)$_7$), i.e., an amino acid sequence of: Pro-Pro-Gly-Pro-Pro-Gly-Pro-Pro-Gly-Pro-Pro-Gly-Pro-Pro-Gly-Pro-Pro-Gly-Pro-Pro-Gly (SEQ ID NO: 1).

In certain other embodiments of the invention, the collagen mimetic peptide comprises, consists essentially of or consists of an amino acid sequence that is or corresponds to a 21-mer comprising seven repeats of a three amino acid sequence in which hydroxyproline (Hyp), and preferably a 4S-hydroxyproline residue, has been substituted for proline$_1$ in SEQ ID NO:1, yielding a sequence of seven repeats of 4S-hydroxyproline-proline-glycine ((Hyp-Pro-Gly)$_7$), i.e., an amino acid sequence of: Hyp-Pro-Gly-Hyp-Pro-Gly-Hyp-Pro-Gly-Hyp-Pro-Gly-Hyp-Pro-Gly-Hyp-Pro-Gly-Hyp-Pro-Gly (SEQ ID NO:2).

In certain other embodiments of the invention, the collagen mimetic peptide comprises, consists essentially of or consists of an amino acid sequence that is or corresponds to a 21-mer comprising seven repeats of a three amino acid sequence in which Hyp, and preferably a 4S-hydroxyproline residue, has been substituted for proline$_2$ in SEQ ID NO: 1, yielding a sequence of seven repeats of 4S-hydroxyproline-proline-glycine ((Pro-Hyp-Gly)$_7$), i.e., an amino acid sequence of: Pro-Hyp-Gly-Pro-Hyp-Gly-Pro-Hyp-Gly-Pro-Hyp-Gly-Pro-Hyp-Gly-Pro-Hyp-Gly-Pro-Hyp-Gly (SEQ ID NO:3).

In certain other embodiments of the invention, the collagen mimetic peptide comprises, consists essentially of or consists of an amino acid sequence that is or corresponds to a 21-mer comprising seven repeats of a three amino acid sequence in which fluoroproline (Flp) has been substituted for proline$_1$ in SEQ ID NO:1, yielding a sequence of seven repeats of fluoroproline-proline-glycine ((Flp-Pro-Gly)$_7$), i.e., an amino acid sequence of: Flp-Pro-Gly-Flp-Pro-Gly-Flp-Pro-Gly-Flp-Pro-Gly-Flp-Pro-Gly-Flp-Pro-Gly-Flp-Pro-Gly (SEQ ID NO:4).

In certain other embodiments of the invention, the collagen mimetic peptide comprises, consists essentially of or consists of an amino acid sequence that is or corresponds to a 21-mer comprising seven repeats of a three amino acid sequence in which Flp has been substituted for proline$_2$ in SEQ ID NO:1, yielding a sequence of seven repeats of proline-fluoroproline-glycine ((Pro-Flp-Gly)$_7$), i.e., an amino acid sequence of: Pro-Flp-Gly-Pro-Flp-Gly-Pro-Flp-Gly-Pro-Flp-Gly-Pro-Flp-Gly-Pro-Flp-Gly-Pro-Flp-Gly (SEQ ID NO:5).

In certain other embodiments of the invention, the collagen mimetic peptide comprises, consists essentially of or consists of an amino acid sequence that is or corresponds to a 21-mer comprising seven repeats of a three amino acid sequence in which fluoroproline (Flp) has been substituted for proline$_1$ in SEQ ID NO:1 and Hyp has been substituted for proline$_2$ in SEQ ID NO:1, yielding a sequence of seven repeats of fluoroproline-hydroxyproline-glycine ((Flp-Hyp-Gly)$_7$), i.e., an amino acid sequence of: Flp-Hyp-Gly-Flp-Hyp-Gly-Flp-Hyp-Gly-Flp-Hyp-Gly-Flp-Hyp-Gly-Flp-Hyp-Gly-Flp-Hyp-Gly (SEQ ID NO:6).

In CMPs containing Flp, the Flp moiety may be in the 4-cis or 4-trans configuration, and preferably is in the 4-cis configuration.

In certain other embodiments of the invention, the collagen mimetic peptide may comprise, consist of or have an amino acid sequence that is or corresponds to a 21-mer comprising seven repeats of a three amino acid sequence in which chloroproline (Clp) has been substituted for proline$_1$ in SEQ ID NO:1, yielding a sequence of seven repeats of chloroproline-proline-glycine ((Clp-Pro-Gly)$_7$), i.e., an amino acid sequence of: Clp-Pro-Gly-Clp-Pro-Gly-Clp-Pro-Gly-Clp-Pro-Gly-Clp-Pro-Gly-Clp-Pro-Gly-Clp-Pro-Gly (SEQ ID NO:7).

In certain other embodiments of the invention, the collagen mimetic peptide may comprise, consist of or have an amino acid sequence that is or corresponds to a 21-mer comprising seven repeats of a three amino acid sequence in which chloroproline (Clp) has been substituted for proline$_2$ in SEQ ID NO:1, yielding a sequence of seven repeats of proline-chloroproline-glycine ((Pro-Clp-Gly)$_7$), i.e., an amino acid sequence of: Pro-Clp-Gly-Pro-Clp-Gly-Pro-Clp-Gly-Pro-Clp-Gly-Pro-Clp-Gly-Pro-Clp-Gly-Pro-Clp-Gly (SEQ ID NO:8).

In certain other embodiments of the invention, the collagen mimetic peptide comprises, consists essentially of or consists of an amino acid sequence that is or corresponds to a 21-mer comprising seven repeats of a three amino acid sequence in which Clp has been substituted for proline$_1$ in SEQ ID NO:1 and Hyp has been substituted for proline$_2$ in SEQ ID NO:1, yielding a sequence of seven repeats of chloroproline-hydroxyproline-glycine ((Clp-Hyp-Gly)$_7$), i.e., an amino acid sequence of: Clp-Hyp-Gly-Clp-Hyp-Gly-Clp-Hyp-Gly-Clp-Hyp-Gly-Clp-Hyp-Gly-Clp-Hyp-Gly-Clp-Hyp-Gly (SEQ ID NO:9).

In CMPs containing Clp, the Clp moiety may be in the 4-cis or 4-trans configuration, and preferably is in the 4-cis configuration.

In certain other embodiments of the invention, the collagen mimetic peptide may comprise, consist of or have an amino acid sequence that is or corresponds to a 21-mer of any one of SEQ ID NOs: 1-9, in which at least one cysteine (Cys) residue has been substituted for at least one of the proline residues in SEQ ID NO: 1, at least one of the hydroxyproline residues in SEQ ID NOs:2-3 and 6, at least one of the fluoroproline residues in SEQ ID NOs:4-6, or at least one of the chloroproline residues in SEQ ID NOs:7-9, yielding, for example, the following sequences:

```
                                      (SEQ ID NO: 10)
Pro-Pro-Gly-Pro-Pro-Gly-Cys-Pro-Gly-Pro-Pro-Gly-
Pro-Pro-Gly-Pro-Pro-Gly-Pro-Pro-Gly;

(SEQ ID NO: 11)
Hyp-Pro-Gly-Hyp-Pro-Gly-Cys-Pro-Gly-Hyp-Pro-Gly-
Hyp-Pro-Gly-Hyp-Pro-Gly-Hyp-Pro-Gly;

(SEQ ID NO: 12)
Pro-Hyp-Gly-Pro-Hyp-Gly-Pro-Cys-Gly-Pro-Hyp-Gly-
Pro-Hyp-Gly-Pro-Hyp-Gly-Pro-Hyp-Gly;

(SEQ ID NO: 13)
Pro-Flp-Gly-Pro-Flp-Gly-Pro-Cys-Gly-Pro-Flp-Gly-
Pro-Flp-Gly-Pro-Flp-Gly-Pro-Flp-Gly;
```

-continued (SEQ ID NO: 14)
Pro-Clp-Gly-Pro-Clp-Gly-Pro-Cys-Gly-Pro-Clp-Gly-
Pro-Clp-Gly-Pro-Clp-Gly-Pro-Clp-Gly;

(SEQ ID NO: 15)
Cys-Pro-Gly-Pro-Pro-Gly-Pro-Pro-Gly-Pro-Pro-Gly-
Pro-Pro-Gly-Pro-Pro-Gly-Pro-Pro-Gly;

(SEQ ID NO: 16)
Pro-Cys-Gly-Pro-Pro-Gly-Pro-Pro-Gly-Pro-Pro-Gly-
Pro-Pro-Gly-Pro-Pro-Gly-Pro-Pro-Gly;

(SEQ ID NO: 17)
Pro-Pro-Gly-Cys-Pro-Gly-Pro-Pro-Gly-Pro-Pro-Gly-
Pro-Pro-Gly-Pro-Pro-Gly-Pro-Pro-Gly;

(SEQ ID NO: 18)
Pro-Pro-Gly-Pro-Cys-Gly-Pro-Pro-Gly-Pro-Pro-Gly-
Pro-Pro-Gly-Pro-Pro-Gly-Pro-Pro-Gly;

(SEQ ID NO: 19)
Pro-Pro-Gly-Pro-Pro-Gly-Pro-Cys-Gly-Pro-Pro-Gly-
Pro-Pro-Gly-Pro-Pro-Gly-Pro-Pro-Gly;

(SEQ ID NO: 20)
Pro-Pro-Gly-Pro-Pro-Gly-Pro-Pro-Gly-Cys-Pro-Gly-
Pro-Pro-Gly-Pro-Pro-Gly-Pro-Pro-Gly;

(SEQ ID NO: 21)
Pro-Pro-Gly-Pro-Pro-Gly-Pro-Pro-Gly-Pro-Cys-Gly-
Pro-Pro-Gly-Pro-Pro-Gly-Pro-Pro-Gly;

(SEQ ID NO: 22)
Pro-Pro-Gly-Pro-Pro-Gly-Pro-Pro-Gly-Pro-Pro-Gly-
Cys-Pro-Gly-Pro-Pro-Gly-Pro-Pro-Gly;

(SEQ ID NO: 23)
Pro-Pro-Gly-Pro-Pro-Gly-Pro-Pro-Gly-Pro-Pro-Gly-
Pro-Cys-Gly-Pro-Pro-Gly-Pro-Pro-Gly;

(SEQ ID NO: 24)
Pro-Pro-Gly-Pro-Pro-Gly-Pro-Pro-Gly-Pro-Pro-Gly-
Pro-Pro-Gly-Cys-Pro-Gly-Pro-Pro-Gly;

(SEQ ID NO: 25)
Pro-Pro-Gly-Pro-Pro-Gly-Pro-Pro-Gly-Pro-Pro-Gly-
Pro-Pro-Gly-Pro-Cys-Gly-Cys-Pro-Gly;

(SEQ ID NO: 26)
Pro-Pro-Gly-Pro-Pro-Gly-Pro-Pro-Gly-Pro-Pro-Gly-
Pro-Pro-Gly-Pro-Pro-Gly-Cys-Pro-Gly;

(SEQ ID NO: 27)
Pro-Pro-Gly-Pro-Pro-Gly-Pro-Pro-Gly-Pro-Pro-Gly-
Pro-Pro-Gly-Pro-Pro-Gly-Pro-Cys-Gly;

(SEQ ID NO: 28)
Cys-Pro-Gly-Hyp-Pro-Gly-Hyp-Pro-Gly-Hyp-Pro-Gly-
Hyp-Pro-Gly-Hyp-Pro-Gly-Hyp-Pro-Gly;

(SEQ ID NO: 29)
Hyp-Cys-Gly-Hyp-Pro-Gly-Hyp-Pro-Gly-Hyp-Pro-Gly-
Hyp-Pro-Gly-Hyp-Pro-Gly-Hyp-Pro-Gly;

(SEQ ID NO: 30)
Hyp-Pro-Gly-Cys-Pro-Gly-Hyp-Pro-Gly-Hyp-Pro-Gly-
Hyp-Pro-Gly-Hyp-Pro-Gly-Hyp-Pro-Gly;

(SEQ ID NO: 31)
Hyp-Pro-Gly-Hyp-Cys-Gly-Hyp-Pro-Gly-Hyp-Pro-Gly-
Hyp-Pro-Gly-Hyp-Pro-Gly-Hyp-Pro-Gly;

(SEQ ID NO: 32)
Hyp-Pro-Gly-Hyp-Pro-Gly-Hyp-Cys-Gly-Hyp-Pro-Gly-
Hyp-Pro-Gly-Hyp-Pro-Gly-Hyp-Pro-Gly;

(SEQ ID NO: 33)
Hyp-Pro-Gly-Hyp-Pro-Gly-Hyp-Pro-Gly-Cys-Pro-Gly-
Hyp-Pro-Gly-Hyp-Pro-Gly-Hyp-Pro-Gly;

(SEQ ID NO: 34)
Hyp-Pro-Gly-Hyp-Pro-Gly-Hyp-Pro-Gly-Hyp-Cys-Gly-
Hyp-Pro-Gly-Hyp-Pro-Gly-Hyp-Pro-Gly;

(SEQ ID NO: 35)
Hyp-Pro-Gly-Hyp-Pro-Gly-Hyp-Pro-Gly-Hyp-Pro-Gly-
Cys-Pro-Gly-Hyp-Pro-Gly-Hyp-Pro-Gly;

(SEQ ID NO: 36)
Hyp-Pro-Gly-Hyp-Pro-Gly-Hyp-Pro-Gly-Hyp-Pro-Gly-
Hyp-Cys-Gly-Hyp-Pro-Gly-Hyp-Pro-Gly;

(SEQ ID NO: 37)
Hyp-Pro-Gly-Hyp-Pro-Gly-Hyp-Pro-Gly-Hyp-Pro-Gly-
Hyp-Pro-Gly-Cys-Pro-Gly-Hyp-Pro-Gly;

(SEQ ID NO: 38)
Hyp-Pro-Gly-Hyp-Pro-Gly-Hyp-Pro-Gly-Hyp-Pro-Gly-
Hyp-Pro-Gly-Hyp-Cys-Gly-Hyp-Pro-Gly;

(SEQ ID NO: 39)
Hyp-Pro-Gly-Hyp-Pro-Gly-Hyp-Pro-Gly-Hyp-Pro-Gly-
Hyp-Pro-Gly-Hyp-Pro-Gly-Cys-Pro-Gly;

(SEQ ID NO: 40)
Hyp-Pro-Gly-Hyp-Pro-Gly-Hyp-Pro-Gly-Hyp-Pro-Gly-
Hyp-Pro-Gly-Hyp-Pro-Gly-Hyp-Cys-Gly;

(SEQ ID NO: 41)
Cys-Hyp-Gly-Pro-Hyp-Gly-Pro-Hyp-Gly-Pro-Hyp-Gly-
Pro-Hyp-Gly-Pro-Hyp-Gly-Pro-Hyp-Gly;

(SEQ ID NO: 42)
Pro-Cys-Gly-Pro-Hyp-Gly-Pro-Hyp-Gly-Pro-Hyp-Gly-
Pro-Hyp-Gly-Pro-Hyp-Gly-Pro-Hyp-Gly;

(SEQ ID NO: 43)
Pro-Hyp-Gly-Cys-Hyp-Gly-Pro-Hyp-Gly-Pro-Hyp-Gly-
Pro-Hyp-Gly-Pro-Hyp-Gly-Pro-Hyp-Gly;

(SEQ ID NO: 44)
Pro-Hyp-Gly-Pro-Cys-Gly-Pro-Hyp-Gly-Pro-Hyp-Gly-
Pro-Hyp-Gly-Pro-Hyp-Gly-Pro-Hyp-Gly;

(SEQ ID NO: 45)
Pro-Hyp-Gly-Pro-Hyp-Gly-Cys-Hyp-Gly-Pro-Hyp-Gly-
Pro-Hyp-Gly-Pro-Hyp-Gly-Pro-Hyp-Gly;

(SEQ ID NO: 46)
Pro-Hyp-Gly-Pro-Hyp-Gly-Pro-Hyp-Gly-Cys-Hyp-Gly-
Pro-Hyp-Gly-Pro-Hyp-Gly-Pro-Hyp-Gly;

(SEQ ID NO: 47)
Pro-Hyp-Gly-Pro-Hyp-Gly-Pro-Hyp-Gly-Pro-Cys-Gly-
Pro-Hyp-Gly-Pro-Hyp-Gly-Pro-Hyp-Gly;

(SEQ ID NO: 48)
Pro-Hyp-Gly-Pro-Hyp-Gly-Pro-Hyp-Gly-Pro-Hyp-Gly-
Cys-Hyp-Gly-Pro-Hyp-Gly-Pro-Hyp-Gly;

(SEQ ID NO: 49)
Pro-Hyp-Gly-Pro-Hyp-Gly-Pro-Hyp-Gly-Pro-Hyp-Gly-
Pro-Cys-Gly-Pro-Hyp-Gly-Pro-Hyp-Gly;

(SEQ ID NO: 50)
Pro-Hyp-Gly-Pro-Hyp-Gly-Pro-Hyp-Gly-Pro-Hyp-Gly-
Pro-Hyp-Gly-Cys-Hyp-Gly-Pro-Hyp-Gly;

(SEQ ID NO: 51)
Pro-Hyp-Gly-Pro-Hyp-Gly-Pro-Hyp-Gly-Pro-Hyp-Gly-
Pro-Hyp-Gly-Pro-Cys-Gly-Pro-Hyp-Gly;

(SEQ ID NO: 52)
Pro-Hyp-Gly-Pro-Hyp-Gly-Pro-Hyp-Gly-Pro-Hyp-Gly-
Pro-Hyp-Gly-Pro-Hyp-Gly-Cys-Hyp-Gly;

(SEQ ID NO: 53)
Pro-Hyp-Gly-Pro-Hyp-Gly-Pro-Hyp-Gly-Pro-Hyp-Gly-
Pro-Hyp-Gly-Pro-Hyp-Gly-Pro-Cys-Gly;

-continued (SEQ ID NO: 54)
Cys-Flp-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 55)
Pro-Cys-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 56)
Pro-Flp-Gly-Cys-Flp-Gly-Pro-Flp-Gly-Pro-Flp-Gly-
Pro-Flp-Gly-Pro-Flp-Gly-Pro-Flp-Gly;

(SEQ ID NO: 57)
Pro-Flp-Gly-Pro-Cys-Gly-Pro-Flp-Gly-Pro-Flp-Gly-
Pro-Flp-Gly-Pro-Flp-Gly-Pro-Flp-Gly;

(SEQ ID NO: 58)
Pro-Flp-Gly-Pro-Flp-Gly-Cys-Flp-Gly-Pro-Flp-Gly-
Pro-Flp-Gly-Pro-Flp-Gly-Pro-Flp-Gly;

(SEQ ID NO: 59)
Pro-Flp-Gly-Pro-Flp-Gly-Pro-Flp-Gly-Cys-Flp-Gly-
Pro-Flp-Gly-Pro-Flp-Gly-Pro-Flp-Gly;

(SEQ ID NO: 60)
Pro-Flp-Gly-Pro-Flp-Gly-Pro-Flp-Gly-Pro-Cys-Gly-
Pro-Flp-Gly-Pro-Flp-Gly-Pro-Flp-Gly;

(SEQ ID NO: 61)
Pro-Flp-Gly-Pro-Flp-Gly-Pro-Flp-Gly-Pro-Flp-Gly-
Cys-Flp-Gly-Pro-Flp-Gly-Pro-Flp-Gly;

(SEQ ID NO: 62)
Pro-Flp-Gly-Pro-Flp-Gly-Pro-Flp-Gly-Pro-Flp-Gly-
Pro-Cys-Gly-Pro-Flp-Gly-Pro-Flp-Gly;

(SEQ ID NO: 63)
Pro-Flp-Gly-Pro-Flp-Gly-Pro-Flp-Gly-Pro-Flp-Gly-
Pro-Flp-Gly-Cys-Flp-Gly-Pro-Flp-Gly;

(SEQ ID NO: 64)
Pro-Flp-Gly-Pro-Flp-Gly-Pro-Flp-Gly-Pro-Flp-Gly-
Pro-Flp-Gly-Pro-Cys-Gly-Pro-Flp-Gly;

(SEQ ID NO: 65)
Pro-Flp-Gly-Pro-Flp-Gly-Pro-Flp-Gly-Pro-Flp-Gly-
Pro-Flp-Gly-Pro-Flp-Gly-Cys-Flp-Gly;

(SEQ ID NO: 66)
Pro-Flp-Gly-Pro-Flp-Gly-Pro-Flp-Gly-Pro-Flp-Gly-
Pro-Flp-Gly-Pro-Flp-Gly-Pro-Cys-Gly;

(SEQ ID NO: 67)
Cys-Flp-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 68)
Pro-Cys-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 69)
Pro-Flp-Gly-Cys-Flp-Gly-Pro-Flp-Gly-Pro-Flp-Gly-
Pro-Flp-Gly-Pro-Flp-Gly-Pro-Flp-Gly;

(SEQ ID NO: 70)
Pro-Flp-Gly-Pro-Cys-Gly-Pro-Flp-Gly-Pro-Flp-Gly-
Pro-Flp-Gly-Pro-Flp-Gly-Pro-Flp-Gly;

(SEQ ID NO: 71)
Pro-Flp-Gly-Pro-Flp-Gly-Cys-Flp-Gly-Pro-Flp-Gly-
Pro-Flp-Gly-Pro-Flp-Gly-Pro-Flp-Gly;

(SEQ ID NO: 72)
Pro-Flp-Gly-Pro-Flp-Gly-Pro-Cys-Gly-Pro-Flp-Gly-
Pro-Flp-Gly-Pro-Flp-Gly-Pro-Flp-Gly;

(SEQ ID NO: 73)
Pro-Flp-Gly-Pro-Flp-Gly-Pro-Flp-Gly-Cys-Flp-Gly-
Pro-Flp-Gly-Pro-Flp-Gly-Pro-Flp-Gly;

(SEQ ID NO: 74)
Pro-Flp-Gly-Pro-Flp-Gly-Pro-Flp-Gly-Pro-Cys-Gly-
Pro-Flp-Gly-Pro-Flp-Gly-Pro-Flp-Gly;

(SEQ ID NO: 75)
Pro-Flp-Gly-Pro-Flp-Gly-Pro-Flp-Gly-Pro-Flp-Gly-
Cys-Flp-Gly-Pro-Flp-Gly-Pro-Flp-Gly;

(SEQ ID NO: 76)
Pro-Flp-Gly-Pro-Flp-Gly-Pro-Flp-Gly-Pro-Flp-Gly-
Pro-Cys-Gly-Pro-Flp-Gly-Pro-Flp-Gly;

(SEQ ID NO: 77)
Pro-Flp-Gly-Pro-Flp-Gly-Pro-Flp-Gly-Pro-Flp-Gly-
Pro-Flp-Gly-Cys-Flp-Gly-Pro-Flp-Gly;

(SEQ ID NO: 78)
Pro-Flp-Gly-Pro-Flp-Gly-Pro-Flp-Gly-Pro-Flp-Gly-
Pro-Flp-Gly-Pro-Cys-Gly-Pro-Flp-Gly;

(SEQ ID NO: 79)
Pro-Flp-Gly-Pro-Flp-Gly-Pro-Flp-Gly-Pro-Flp-Gly-
Pro-Flp-Gly-Pro-Flp-Gly-Cys-Flp-Gly;

(SEQ ID NO: 80)
Pro-Flp-Gly-Pro-Flp-Gly-Pro-Flp-Gly-Pro-Flp-Gly-
Pro-Flp-Gly-Pro-Flp-Gly-Pro-Cys-Gly;

(SEQ ID NO: 81)
Cys-Hyp-Gly-Flp-Hyp-Gly-Flp-Hyp-Gly-Flp-Hyp-Gly-
Flp-Hyp-Gly-Flp-Hyp-Gly-Flp-Hyp-Gly;

(SEQ ID NO: 82)
Flp-Cys-Gly-Flp-Hyp-Gly-Flp-Hyp-Gly-Flp-Hyp-Gly-
Flp-Hyp-Gly-Flp-Hyp-Gly-Flp-Hyp-Gly;

(SEQ ID NO: 83)
Flp-Hyp-Gly-Cys-Hyp-Gly-Flp-Hyp-Gly-Flp-Hyp-Gly-
Flp-Hyp-Gly-Flp-Hyp-Gly-Flp-Hyp-Gly;

(SEQ ID NO: 84)
Flp-Hyp-Gly-Flp-Cys-Gly-Flp-Hyp-Gly-Flp-Hyp-Gly-
Flp-Hyp-Gly-Flp-Hyp-Gly-Flp-Hyp-Gly;

(SEQ ID NO: 85)
Flp-Hyp-Gly-Flp-Hyp-Gly-Cys-Hyp-Gly-Flp-Hyp-Gly-
Flp-Hyp-Gly-Flp-Hyp-Gly-Flp-Hyp-Gly;

(SEQ ID NO: 86)
Flp-Hyp-Gly-Flp-Hyp-Gly-Flp-Cys-Gly-Flp-Hyp-Gly-
Flp-Hyp-Gly-Flp-Hyp-Gly-Flp-Hyp-Gly;

(SEQ ID NO: 87)
Flp-Hyp-Gly-Flp-Hyp-Gly-Flp-Hyp-Gly-Cys-Hyp-Gly-
Flp-Hyp-Gly-Flp-Hyp-Gly-Flp-Hyp-Gly;

(SEQ ID NO: 88)
Flp-Hyp-Gly-Flp-Hyp-Gly-Flp-Hyp-Gly-Flp-Cys-Gly-
Flp-Hyp-Gly-Flp-Hyp-Gly-Flp-Hyp-Gly;

(SEQ ID NO: 89)
Flp-Hyp-Gly-Flp-Hyp-Gly-Flp-Hyp-Gly-Flp-Hyp-Gly-
Cys-Hyp-Gly-Flp-Hyp-Gly-Flp-Hyp-Gly;

(SEQ ID NO: 90)
Flp-Hyp-Gly-Flp-Hyp-Gly-Flp-Hyp-Gly-Flp-Hyp-Gly-
Flp-Cys-Gly-Flp-Hyp-Gly-Flp-Hyp-Gly;

(SEQ ID NO: 91)
Flp-Hyp-Gly-Flp-Hyp-Gly-Flp-Hyp-Gly-Flp-Hyp-Gly-
Flp-Hyp-Gly-Cys-Hyp-Gly-Flp-Hyp-Gly;

(SEQ ID NO: 92)
Flp-Hyp-Gly-Flp-Hyp-Gly-Flp-Hyp-Gly-Flp-Hyp-Gly-
Flp-Hyp-Gly-Flp-Cys-Gly-Flp-Hyp-Gly;

(SEQ ID NO: 93)
Flp-Hyp-Gly-Flp-Hyp-Gly-Flp-Hyp-Gly-Flp-Hyp-Gly-
Flp-Hyp-Gly-Flp-Hyp-Gly-Cys-Hyp-Gly;

(SEQ ID NO: 94)
Flp-Hyp-Gly-Flp-Hyp-Gly-Flp-Hyp-Gly-Flp-Hyp-Gly-
Flp-Hyp-Gly-Flp-Hyp-Gly-Flp-Cys-Gly;

(SEQ ID NO: 95)
Cys-Clp-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 96)
Pro-Cys-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 97)
Pro-Clp-Gly-Cys-Clp-Gly-Pro-Clp-Gly-Pro-Clp-Gly-
Pro-Clp-Gly-Pro-Clp-Gly-Pro-Clp-Gly;

(SEQ ID NO: 98)
Pro-Clp-Gly-Pro-Cys-Gly-Pro-Clp-Gly-Pro-Clp-Gly-
Pro-Clp-Gly-Pro-Clp-Gly-Pro-Clp-Gly;

(SEQ ID NO: 99)
Pro-Clp-Gly-Pro-Clp-Gly-Cys-Clp-Gly-Pro-Clp-Gly-
Pro-Clp-Gly-Pro-Clp-Gly-Pro-Clp-Gly;

(SEQ ID NO: 100)
Pro-Clp-Gly-Pro-Clp-Gly-Pro-Clp-Gly-Cys-Clp-Gly-
Pro-Clp-Gly-Pro-Clp-Gly-Pro-Clp-Gly;

(SEQ ID NO: 101)
Pro-Clp-Gly-Pro-Clp-Gly-Pro-Clp-Gly-Pro-Cys-Gly-
Pro-Clp-Gly-Pro-Clp-Gly-Pro-Clp-Gly;

(SEQ ID NO: 102)
Pro-Clp-Gly-Pro-Clp-Gly-Pro-Clp-Gly-Pro-Clp-Gly-
Cys-Clp-Gly-Pro-Clp-Gly-Pro-Clp-Gly;

(SEQ ID NO: 103)
Pro-Clp-Gly-Pro-Clp-Gly-Pro-Clp-Gly-Pro-Clp-Gly-
Pro-Cys-Gly-Pro-Clp-Gly-Pro-Clp-Gly;

(SEQ ID NO: 104)
Pro-Clp-Gly-Pro-Clp-Gly-Pro-Clp-Gly-Pro-Clp-Gly-
Pro-Clp-Gly-Cys-Clp-Gly-Pro-Clp-Gly;

(SEQ ID NO: 105)
Pro-Clp-Gly-Pro-Clp-Gly-Pro-Clp-Gly-Pro-Clp-Gly-
Pro-Clp-Gly-Pro-Cys-Gly-Pro-Clp-Gly;

(SEQ ID NO: 106)
Pro-Clp-Gly-Pro-Clp-Gly-Pro-Clp-Gly-Pro-Clp-Gly-
Pro-Clp-Gly-Pro-Clp-Gly-Cys-Clp-Gly;

(SEQ ID NO: 107)
Pro-Clp-Gly-Pro-Clp-Gly-Pro-Clp-Gly-Pro-Clp-Gly-
Pro-Clp-Gly-Pro-Clp-Gly-Pro-Cys-Gly;

(SEQ ID NO: 108)
Cys-Clp-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 109)
Pro-Cys-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 110)
Pro-Clp-Gly-Cys-Clp-Gly-Pro-Clp-Gly-Pro-Clp-Gly-
Pro-Clp-Gly-Pro-Clp-Gly-Pro-Clp-Gly;

(SEQ ID NO: 111)
Pro-Clp-Gly-Pro-Cys-Gly-Pro-Clp-Gly-Pro-Clp-Gly-
Pro-Clp-Gly-Pro-Clp-Gly-Pro-Clp-Gly;

(SEQ ID NO: 112)
Pro-Clp-Gly-Pro-Clp-Gly-Cys-Clp-Gly-Pro-Clp-Gly-
Pro-Clp-Gly-Pro-Clp-Gly-Pro-Clp-Gly;

(SEQ ID NO: 113)
Pro-Clp-Gly-Pro-Clp-Gly-Pro-Cys-Gly-Pro-Clp-Gly-
Pro-Clp-Gly-Pro-Clp-Gly-Pro-Clp-Gly;

(SEQ ID NO: 114)
Pro-Clp-Gly-Pro-Clp-Gly-Pro-Clp-Gly-Cys-Clp-Gly-
Pro-Clp-Gly-Pro-Clp-Gly-Pro-Clp-Gly;

(SEQ ID NO: 115)
Pro-Clp-Gly-Pro-Clp-Gly-Pro-Clp-Gly-Pro-Cys-Gly-
Pro-Clp-Gly-Pro-Clp-Gly-Pro-Clp-Gly;

(SEQ ID NO: 116)
Pro-Clp-Gly-Pro-Clp-Gly-Pro-Clp-Gly-Pro-Clp-Gly-
Cys-Clp-Gly-Pro-Clp-Gly-Pro-Clp-Gly;

(SEQ ID NO: 117)
Pro-Clp-Gly-Pro-Clp-Gly-Pro-Clp-Gly-Pro-Clp-Gly-
Pro-Cys-Gly-Pro-Clp-Gly-Pro-Clp-Gly;

(SEQ ID NO: 118)
Pro-Clp-Gly-Pro-Clp-Gly-Pro-Clp-Gly-Pro-Clp-Gly-
Pro-Clp-Gly-Cys-Clp-Gly-Pro-Clp-Gly;

(SEQ ID NO: 119)
Pro-Clp-Gly-Pro-Clp-Gly-Pro-Clp-Gly-Pro-Clp-Gly-
Pro-Clp-Gly-Pro-Cys-Gly-Pro-Clp-Gly;

(SEQ ID NO: 120)
Pro-Clp-Gly-Pro-Clp-Gly-Pro-Clp-Gly-Pro-Clp-Gly-
Pro-Clp-Gly-Pro-Clp-Gly-Cys-Clp-Gly;

(SEQ ID NO: 121)
Pro-Clp-Gly-Pro-Clp-Gly-Pro-Clp-Gly-Pro-Clp-Gly-
Pro-Clp-Gly-Pro-Clp-Gly-Pro-Cys-Gly;

(SEQ ID NO: 122)
Cys-Hyp-Gly-Clp-Hyp-Gly-Clp-Hyp-Gly-Clp-Hyp-Gly-
Clp-Hyp-Gly-Clp-Hyp-Gly-Clp-Hyp-Gly;

(SEQ ID NO: 123)
Clp-Cys-Gly-Clp-Hyp-Gly-Clp-Hyp-Gly-Clp-Hyp-Gly-
Clp-Hyp-Gly-Clp-Hyp-Gly-Clp-Hyp-Gly;

(SEQ ID NO: 124)
Clp-Hyp-Gly-Cys-Hyp-Gly-Clp-Hyp-Gly-Clp-Hyp-Gly-
Clp-Hyp-Gly-Clp-Hyp-Gly-Clp-Hyp-Gly;

(SEQ ID NO: 125)
Clp-Hyp-Gly-Clp-Cys-Gly-Clp-Hyp-Gly-Clp-Hyp-Gly-
Clp-Hyp-Gly-Clp-Hyp-Gly-Clp-Hyp-Gly;

(SEQ ID NO: 126)
Clp-Hyp-Gly-Clp-Hyp-Gly-Cys-Hyp-Gly-Clp-Hyp-Gly-
Clp-Hyp-Gly-Clp-Hyp-Gly-Clp-Hyp-Gly;

(SEQ ID NO: 127)
Clp-Hyp-Gly-Clp-Hyp-Gly-Clp-Cys-Gly-Clp-Hyp-Gly-
Clp-Hyp-Gly-Clp-Hyp-Gly-Clp-Hyp-Gly;

(SEQ ID NO: 128)
Clp-Hyp-Gly-Clp-Hyp-Gly-Clp-Hyp-Gly-Cys-Hyp-Gly-
Clp-Hyp-Gly-Clp-Hyp-Gly-Clp-Hyp-Gly;

(SEQ ID NO: 129)
Clp-Hyp-Gly-Clp-Hyp-Gly-Clp-Hyp-Gly-Clp-Cys-Gly-
Clp-Hyp-Gly-Clp-Hyp-Gly-Clp-Hyp-Gly;

(SEQ ID NO: 130)
Clp-Hyp-Gly-Clp-Hyp-Gly-Clp-Hyp-Gly-Clp-Hyp-Gly-
Cys-Hyp-Gly-Clp-Hyp-Gly-Clp-Hyp-Gly;

(SEQ ID NO: 131)
Clp-Hyp-Gly-Clp-Hyp-Gly-Clp-Hyp-Gly-Clp-Hyp-Gly-
Clp-Cys-Gly-Clp-Hyp-Gly-Clp-Hyp-Gly;

(SEQ ID NO: 132)
Clp-Hyp-Gly-Clp-Hyp-Gly-Clp-Hyp-Gly-Clp-Hyp-Gly-
Clp-Hyp-Gly-Cys-Hyp-Gly-Clp-Hyp-Gly;

(SEQ ID NO: 133)
Clp-Hyp-Gly-Clp-Hyp-Gly-Clp-Hyp-Gly-Clp-Hyp-Gly-
Clp-Hyp-Gly-Clp-Cys-Gly-Clp-Hyp-Gly;

(SEQ ID NO: 134)
Clp-Hyp-Gly-Clp-Hyp-Gly-Clp-Hyp-Gly-Clp-Hyp-Gly-
Clp-Hyp-Gly-Clp-Hyp-Gly-Cys-Hyp-Gly;
and (SEQ ID NO: 135)
Clp-Hyp-Gly-Clp-Hyp-Gly-Clp-Hyp-Gly-Clp-Hyp-Gly-
Clp-Hyp-Gly-Clp-Hyp-Gly-Clp-Cys-Gly.

In certain other embodiments of the invention, the collagen mimetic peptide may comprise, consist of or have an amino acid sequence that is or corresponds to a 21-mer of any one of SEQ ID NOs: 1-9, in which at least one methionine (Met) residue has been substituted for at least one of the proline residues in SEQ ID NO: 1, at least one of the hydroxyproline residues in SEQ ID NOs:2-3 and 6, at least one of the fluoroproline residues in SEQ ID NOs:4-6, or at least one of the chloroproline residues in SEQ ID NOs:7-9, yielding, for example, the following sequences:

(SEQ ID NO: 136)
Pro-Pro-Gly-Pro-Pro-Gly-Met-Pro-Gly-Pro-Pro-Gly-
Pro-Pro-Gly-Pro-Pro-Gly-Pro-Pro-Gly;

(SEQ ID NO: 137)
Hyp-Pro-Gly-Hyp-Pro-Gly-Met-Pro-Gly-Hyp-Pro-Gly-
Hyp-Pro-Gly-Hyp-Pro-Gly-Hyp-Pro-Gly;

(SEQ ID NO: 138)
Pro-Hyp-Gly-Pro-Hyp-Gly-Pro-Met-Gly-Pro-Hyp-Gly-
Pro-Hyp-Gly-Pro-Hyp-Gly-Pro-Hyp-Gly;

(SEQ ID NO: 139)
Pro-Flp-Gly-Pro-Flp-Gly-Pro-Met-Gly-Pro-Flp-Gly-
Pro-Flp-Gly-Pro-Flp-Gly-Pro-Flp-Gly;

(SEQ ID NO: 140)
Pro-Clp-Gly-Pro-Clp-Gly-Pro-Met-Gly-Pro-Clp-Gly-
Pro-Clp-Gly-Pro-Clp-Gly-Pro-Clp-Gly;

(SEQ ID NO: 141)
Met-Pro-Gly-Pro-Pro-Gly-Pro-Pro-Gly-Pro-Pro-Gly-
Pro-Pro-Gly-Pro-Pro-Gly-Pro-Pro-Gly;

(SEQ ID NO: 142)
Pro-Met-Gly-Pro-Pro-Gly-Pro-Pro-Gly-Pro-Pro-Gly-
Pro-Pro-Gly-Pro-Pro-Gly-Pro-Pro-Gly;

(SEQ ID NO: 143)
Pro-Pro-Gly-Met-Pro-Gly-Pro-Pro-Gly-Pro-Pro-Gly-
Pro-Pro-Gly-Pro-Pro-Gly-Pro-Pro-Gly;

(SEQ ID NO: 144)
Pro-Pro-Gly-Pro-Met-Gly-Pro-Pro-Gly-Pro-Pro-Gly-
Pro-Pro-Gly-Pro-Pro-Gly-Pro-Pro-Gly;

(SEQ ID NO: 145)
Pro-Pro-Gly-Pro-Pro-Gly-Pro-Met-Gly-Pro-Pro-Gly-
Pro-Pro-Gly-Pro-Pro-Gly-Pro-Pro-Gly;

(SEQ ID NO: 146)
Pro-Pro-Gly-Pro-Pro-Gly-Pro-Pro-Gly-Met-Pro-Gly-
Pro-Pro-Gly-Pro-Pro-Gly-Pro-Pro-Gly;

(SEQ ID NO: 147)
Pro-Pro-Gly-Pro-Pro-Gly-Pro-Pro-Gly-Pro-Met-Gly-
Pro-Pro-Gly-Pro-Pro-Gly-Pro-Pro-Gly;

(SEQ ID NO: 148)
Pro-Pro-Gly-Pro-Pro-Gly-Pro-Pro-Gly-Pro-Pro-Gly-
Met-Pro-Gly-Pro-Pro-Gly-Pro-Pro-Gly;

(SEQ ID NO: 149)
Pro-Pro-Gly-Pro-Pro-Gly-Pro-Pro-Gly-Pro-Pro-Gly-
Pro-Met-Gly-Pro-Pro-Gly-Pro-Pro-Gly;

(SEQ ID NO: 150)
Pro-Pro-Gly-Pro-Pro-Gly-Pro-Pro-Gly-Pro-Pro-Gly-
Pro-Pro-Gly-Met-Pro-Gly-Pro-Pro-Gly;

(SEQ ID NO: 151)
Pro-Pro-Gly-Pro-Pro-Gly-Pro-Pro-Gly-Pro-Pro-Gly-
Pro-Pro-Gly-Pro-Met-Gly-Pro-Pro-Gly;

(SEQ ID NO: 152)
Pro-Pro-Gly-Pro-Pro-Gly-Pro-Pro-Gly-Pro-Pro-Gly-
Pro-Pro-Gly-Pro-Pro-Gly-Met-Pro-Gly;

(SEQ ID NO: 153)
Pro-Pro-Gly-Pro-Pro-Gly-Pro-Pro-Gly-Pro-Pro-Gly-
Pro-Pro-Gly-Pro-Pro-Gly-Pro-Met-Gly;

(SEQ ID NO: 154)
Met-Pro-Gly-Hyp-Pro-Gly-Hyp-Pro-Gly-Hyp-Pro-Gly-
Hyp-Pro-Gly-Hyp-Pro-Gly-Hyp-Pro-Gly;

(SEQ ID NO: 155)
Hyp-Met-Gly-Hyp-Pro-Gly-Hyp-Pro-Gly-Hyp-Pro-Gly-
Hyp-Pro-Gly-Hyp-Pro-Gly-Hyp-Pro-Gly;

(SEQ ID NO: 156)
Hyp-Pro-Gly-Met-Pro-Gly-Hyp-Pro-Gly-Hyp-Pro-Gly-
Hyp-Pro-Gly-Hyp-Pro-Gly-Hyp-Pro-Gly;

(SEQ ID NO: 157)
Hyp-Pro-Gly-Hyp-Met-Gly-Hyp-Pro-Gly-Hyp-Pro-Gly-
Hyp-Pro-Gly-Hyp-Pro-Gly-Hyp-Pro-Gly;

(SEQ ID NO: 158)
Hyp-Pro-Gly-Hyp-Pro-Gly-Hyp-Met-Gly-Hyp-Pro-Gly-
Hyp-Pro-Gly-Hyp-Pro-Gly-Hyp-Pro-Gly;

(SEQ ID NO: 159)
Hyp-Pro-Gly-Hyp-Pro-Gly-Hyp-Pro-Gly-Met-Pro-Gly-
Hyp-Pro-Gly-Hyp-Pro-Gly-Hyp-Pro-Gly;

(SEQ ID NO: 160)
Hyp-Pro-Gly-Hyp-Pro-Gly-Hyp-Pro-Gly-Hyp-Met-Gly-
Hyp-Pro-Gly-Hyp-Pro-Gly-Hyp-Pro-Gly;

(SEQ ID NO: 161)
Hyp-Pro-Gly-Hyp-Pro-Gly-Hyp-Pro-Gly-Hyp-Pro-Gly-
Met-Pro-Gly-Hyp-Pro-Gly-Hyp-Pro-Gly;

(SEQ ID NO: 162)
Hyp-Pro-Gly-Hyp-Pro-Gly-Hyp-Pro-Gly-Hyp-Pro-Gly-
Hyp-Met-Gly-Hyp-Pro-Gly-Hyp-Pro-Gly;

(SEQ ID NO: 163)
Hyp-Pro-Gly-Hyp-Pro-Gly-Hyp-Pro-Gly-Hyp-Pro-Gly-
Hyp-Pro-Gly-Met-Pro-Gly-Hyp-Pro-Gly;

(SEQ ID NO: 164)
Hyp-Pro-Gly-Hyp-Pro-Gly-Hyp-Pro-Gly-Hyp-Pro-Gly-
Hyp-Pro-Gly-Hyp-Met-Gly-Hyp-Pro-Gly;

(SEQ ID NO: 165)
Hyp-Pro-Gly-Hyp-Pro-Gly-Hyp-Pro-Gly-Hyp-Pro-Gly-
Hyp-Pro-Gly-Hyp-Pro-Gly-Met-Pro-Gly;

(SEQ ID NO: 166)
Hyp-Pro-Gly-Hyp-Pro-Gly-Hyp-Pro-Gly-Hyp-Pro-Gly-
Hyp-Pro-Gly-Hyp-Pro-Gly-Hyp-Met-Gly;

(SEQ ID NO: 167)
Met-Hyp-Gly-Pro-Hyp-Gly-Pro-Hyp-Gly-Pro-Hyp-Gly-
Pro-Hyp-Gly-Pro-Hyp-Gly-Pro-Hyp-Gly;

(SEQ ID NO: 168)
Pro-Met-Gly-Pro-Hyp-Gly-Pro-Hyp-Gly-Pro-Hyp-Gly-
Pro-Hyp-Gly-Pro-Hyp-Gly-Pro-Hyp-Gly;

(SEQ ID NO: 169)
Pro-Hyp-Gly-Met-Hyp-Gly-Pro-Hyp-Gly-Pro-Hyp-Gly-
Pro-Hyp-Gly-Pro-Hyp-Gly-Pro-Hyp-Gly;

-continued (SEQ ID NO: 170)
Pro-Hyp-Gly-Pro-Met-Gly-Pro-Hyp-Gly-Pro-Hyp-Gly-
Pro-Hyp-Gly-Pro-Hyp-Gly-Pro-Hyp-Gly;

(SEQ ID NO: 171)
Pro-Hyp-Gly-Pro-Hyp-Gly-Met-Hyp-Gly-Pro-Hyp-Gly-
Pro-Hyp-Gly-Pro-Hyp-Gly-Pro-Hyp-Gly;

(SEQ ID NO: 172)
Pro-Hyp-Gly-Pro-Hyp-Gly-Pro-Hyp-Gly-Met-Hyp-Gly-
Pro-Hyp-Gly-Pro-Hyp-Gly-Pro-Hyp-Gly;

(SEQ ID NO: 173)
Pro-Hyp-Gly-Pro-Hyp-Gly-Pro-Hyp-Gly-Pro-Met-Gly-
Pro-Hyp-Gly-Pro-Hyp-Gly-Pro-Hyp-Gly;

(SEQ ID NO: 174)
Pro-Hyp-Gly-Pro-Hyp-Gly-Pro-Hyp-Gly-Pro-Hyp-Gly-
Met-Hyp-Gly-Pro-Hyp-Gly-Pro-Hyp-Gly;

(SEQ ID NO: 175)
Pro-Hyp-Gly-Pro-Hyp-Gly-Pro-Hyp-Gly-Pro-Hyp-Gly-
Pro-Met-Gly-Pro-Hyp-Gly-Pro-Hyp-Gly;

(SEQ ID NO: 176)
Pro-Hyp-Gly-Pro-Hyp-Gly-Pro-Hyp-Gly-Pro-Hyp-Gly-
Pro-Hyp-Gly-Met-Hyp-Gly-Pro-Hyp-Gly;

(SEQ ID NO: 177)
Pro-Hyp-Gly-Pro-Hyp-Gly-Pro-Hyp-Gly-Pro-Hyp-Gly-
Pro-Hyp-Gly-Pro-Met-Gly-Pro-Hyp-Gly;

(SEQ ID NO: 178)
Pro-Hyp-Gly-Pro-Hyp-Gly-Pro-Hyp-Gly-Pro-Hyp-Gly-
Pro-Hyp-Gly-Pro-Hyp-Gly-Met-Hyp-Gly;

(SEQ ID NO: 179)
Pro-Hyp-Gly-Pro-Hyp-Gly-Pro-Hyp-Gly-Pro-Hyp-Gly-
Pro-Hyp-Gly-Pro-Hyp-Gly-Pro-Met-Gly;

(SEQ ID NO: 180)
Met-Flp-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 181)
Pro-Met-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 182)
Pro-Flp-Gly-Met-Flp-Gly-Pro-Flp-Gly-Pro-Flp-Gly-
Pro-Flp-Gly-Pro-Flp-Gly-Pro-Flp-Gly;

(SEQ ID NO: 183)
Pro-Flp-Gly-Pro-Met-Gly-Pro-Flp-Gly-Pro-Flp-Gly-
Pro-Flp-Gly-Pro-Flp-Gly-Pro-Flp-Gly;

(SEQ ID NO: 184)
Pro-Flp-Gly-Pro-Flp-Gly-Met-Flp-Gly-Pro-Flp-Gly-
Pro-Flp-Gly-Pro-Flp-Gly-Pro-Flp-Gly;

(SEQ ID NO: 185)
Pro-Flp-Gly-Pro-Flp-Gly-Pro-Flp-Gly-Met-Flp-Gly-
Pro-Flp-Gly-Pro-Flp-Gly-Pro-Flp-Gly;

(SEQ ID NO: 186)
Pro-Flp-Gly-Pro-Flp-Gly-Pro-Flp-Gly-Pro-Met-Gly-
Pro-Flp-Gly-Pro-Flp-Gly-Pro-Flp-Gly;

(SEQ ID NO: 187)
Pro-Flp-Gly-Pro-Flp-Gly-Pro-Flp-Gly-Pro-Flp-Gly-
Met-Flp-Gly-Pro-Flp-Gly-Pro-Flp-Gly;

(SEQ ID NO: 188)
Pro-Flp-Gly-Pro-Flp-Gly-Pro-Flp-Gly-Pro-Flp-Gly-
Pro-Met-Gly-Pro-Flp-Gly-Pro-Flp-Gly;

(SEQ ID NO: 189)
Pro-Flp-Gly-Pro-Flp-Gly-Pro-Flp-Gly-Pro-Flp-Gly-
Pro-Flp-Gly-Met-Flp-Gly-Pro-Flp-Gly;

(SEQ ID NO: 190)
Pro-Flp-Gly-Pro-Flp-Gly-Pro-Flp-Gly-Pro-Flp-Gly-
Pro-Flp-Gly-Pro-Met-Gly-Pro-Flp-Gly;

(SEQ ID NO: 191)
Pro-Flp-Gly-Pro-Flp-Gly-Pro-Flp-Gly-Pro-Flp-Gly-
Pro-Flp-Gly-Pro-Flp-Gly-Met-Flp-Gly;

(SEQ ID NO: 192)
Pro-Flp-Gly-Pro-Flp-Gly-Pro-Flp-Gly-Pro-Flp-Gly-
Pro-Flp-Gly-Pro-Flp-Gly-Pro-Met-Gly;

(SEQ ID NO: 193)
Met-Flp-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 194)
Pro-Met-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 195)
Pro-Flp-Gly-Met-Flp-Gly-Pro-Flp-Gly-Pro-Flp-Gly-
Pro-Flp-Gly-Pro-Flp-Gly-Pro-Flp-Gly;

(SEQ ID NO: 196)
Pro-Flp-Gly-Pro-Met-Gly-Pro-Flp-Gly-Pro-Flp-Gly-
Pro-Flp-Gly-Pro-Flp-Gly-Pro-Flp-Gly;

(SEQ ID NO: 197)
Pro-Flp-Gly-Pro-Flp-Gly-Met-Flp-Gly-Pro-Flp-Gly-
Pro-Flp-Gly-Pro-Flp-Gly-Pro-Flp-Gly;

(SEQ ID NO: 198)
Pro-Flp-Gly-Pro-Flp-Gly-Pro-Met-Gly-Pro-Flp-Gly-
Pro-Flp-Gly-Pro-Flp-Gly-Pro-Flp-Gly;

(SEQ ID NO: 199)
Pro-Flp-Gly-Pro-Flp-Gly-Pro-Flp-Gly-Met-Flp-Gly-
Pro-Flp-Gly-Pro-Flp-Gly-Pro-Flp-Gly;

(SEQ ID NO: 200)
Pro-Flp-Gly-Pro-Flp-Gly-Pro-Flp-Gly-Pro-Met-Gly-
Pro-Flp-Gly-Pro-Flp-Gly-Pro-Flp-Gly;

(SEQ ID NO: 201)
Pro-Flp-Gly-Pro-Flp-Gly-Pro-Flp-Gly-Pro-Flp-Gly-
Met-Flp-Gly-Pro-Flp-Gly-Pro-Flp-Gly;

(SEQ ID NO: 202)
Pro-Flp-Gly-Pro-Flp-Gly-Pro-Flp-Gly-Pro-Flp-Gly-
Pro-Met-Gly-Pro-Flp-Gly-Pro-Flp-Gly;

(SEQ ID NO: 203)
Pro-Flp-Gly-Pro-Flp-Gly-Pro-Flp-Gly-Pro-Flp-Gly-
Pro-Flp-Gly-Met-Flp-Gly-Pro-Flp-Gly;

(SEQ ID NO: 204)
Pro-Flp-Gly-Pro-Flp-Gly-Pro-Flp-Gly-Pro-Flp-Gly-
Pro-Flp-Gly-Pro-Met-Gly-Pro-Flp-Gly;

(SEQ ID NO: 205)
Pro-Flp-Gly-Pro-Flp-Gly-Pro-Flp-Gly-Pro-Flp-Gly-
Pro-Flp-Gly-Pro-Flp-Gly-Met-Flp-Gly;

(SEQ ID NO: 206)
Pro-Flp-Gly-Pro-Flp-Gly-Pro-Flp-Gly-Pro-Flp-Gly-
Pro-Flp-Gly-Pro-Flp-Gly-Pro-Met-Gly;

(SEQ ID NO: 207)
Met-Hyp-Gly-Flp-Hyp-Gly-Flp-Hyp-Gly-Flp-Hyp-Gly-
Flp-Hyp-Gly-Flp-Hyp-Gly-Flp-Hyp-Gly;

(SEQ ID NO: 208)
Flp-Met-Gly-Flp-Hyp-Gly-Flp-Hyp-Gly-Flp-Hyp-Gly-
Flp-Hyp-Gly-Flp-Hyp-Gly-Flp-Hyp-Gly;

(SEQ ID NO: 209)
Flp-Hyp-Gly-Met-Hyp-Gly-Flp-Hyp-Gly-Flp-Hyp-Gly-
Flp-Hyp-Gly-Flp-Hyp-Gly-Flp-Hyp-Gly;

(SEQ ID NO: 210)
Flp-Hyp-Gly-Flp-Met-Gly-Flp-Hyp-Gly-Flp-Hyp-Gly-
Flp-Hyp-Gly-Flp-Hyp-Gly-Flp-Hyp-Gly;

(SEQ ID NO: 211)
Flp-Hyp-Gly-Flp-Hyp-Gly-Met-Hyp-Gly-Flp-Hyp-Gly-
Flp-Hyp-Gly-Flp-Hyp-Gly-Flp-Hyp-Gly;

(SEQ ID NO: 212)
Flp-Hyp-Gly-Flp-Hyp-Gly-Flp-Met-Gly-Flp-Hyp-Gly-
Flp-Hyp-Gly-Flp-Hyp-Gly-Flp-Hyp-Gly;

(SEQ ID NO: 213)
Flp-Hyp-Gly-Flp-Hyp-Gly-Flp-Hyp-Gly-Met-Hyp-Gly-
Flp-Hyp-Gly-Flp-Hyp-Gly-Flp-Hyp-Gly;

(SEQ ID NO: 214)
Flp-Hyp-Gly-Flp-Hyp-Gly-Flp-Hyp-Gly-Flp-Met-Gly-
Flp-Hyp-Gly-Flp-Hyp-Gly-Flp-Hyp-Gly;

(SEQ ID NO: 215)
Flp-Hyp-Gly-Flp-Hyp-Gly-Flp-Hyp-Gly-Flp-Hyp-Gly-
Met-Hyp-Gly-Flp-Hyp-Gly-Flp-Hyp-Gly;

(SEQ ID NO: 216)
Flp-Hyp-Gly-Flp-Hyp-Gly-Flp-Hyp-Gly-Flp-Hyp-Gly-
Flp-Met-Gly-Flp-Hyp-Gly-Flp-Hyp-Gly;

(SEQ ID NO: 217)
Flp-Hyp-Gly-Flp-Hyp-Gly-Flp-Hyp-Gly-Flp-Hyp-Gly-
Flp-Hyp-Gly-Met-Hyp-Gly-Flp-Hyp-Gly;

(SEQ ID NO: 218)
Flp-Hyp-Gly-Flp-Hyp-Gly-Flp-Hyp-Gly-Flp-Hyp-Gly-
Flp-Hyp-Gly-Flp-Met-Gly-Flp-Hyp-Gly;

(SEQ ID NO: 219)
Flp-Hyp-Gly-Flp-Hyp-Gly-Flp-Hyp-Gly-Flp-Hyp-Gly-
Flp-Hyp-Gly-Flp-Hyp-Gly-Met-Hyp-Gly;

(SEQ ID NO: 220)
Flp-Hyp-Gly-Flp-Hyp-Gly-Flp-Hyp-Gly-Flp-Hyp-Gly-
Flp-Hyp-Gly-Flp-Hyp-Gly-Flp-Met-Gly;

(SEQ ID NO: 221)
Met-Clp-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 222)
Pro-Met-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 223)
Pro-Clp-Gly-Met-Clp-Gly-Pro-Clp-Gly-Pro-Clp-Gly-
Pro-Clp-Gly-Pro-Clp-Gly-Pro-Clp-Gly;

(SEQ ID NO: 224)
Pro-Clp-Gly-Pro-Met-Gly-Pro-Clp-Gly-Pro-Clp-Gly-
Pro-Clp-Gly-Pro-Clp-Gly-Pro-Clp-Gly;

(SEQ ID NO: 225)
Pro-Clp-Gly-Pro-Clp-Gly-Met-Clp-Gly-Pro-Clp-Gly-
Pro-Clp-Gly-Pro-Clp-Gly-Pro-Clp-Gly;

(SEQ ID NO: 226)
Pro-Clp-Gly-Pro-Clp-Gly-Pro-Clp-Gly-Met-Clp-Gly-
Pro-Clp-Gly-Pro-Clp-Gly-Pro-Clp-Gly;

(SEQ ID NO: 227)
Pro-Clp-Gly-Pro-Clp-Gly-Pro-Clp-Gly-Pro-Met-Gly-
Pro-Clp-Gly-Pro-Clp-Gly-Pro-Clp-Gly;

(SEQ ID NO: 228)
Pro-Clp-Gly-Pro-Clp-Gly-Pro-Clp-Gly-Pro-Clp-Gly-
Met-Clp-Gly-Pro-Clp-Gly-Pro-Clp-Gly;

(SEQ ID NO: 229)
Pro-Clp-Gly-Pro-Clp-Gly-Pro-Clp-Gly-Pro-Clp-Gly-
Pro-Met-Gly-Pro-Clp-Gly-Pro-Clp-Gly;

(SEQ ID NO: 230)
Pro-Clp-Gly-Pro-Clp-Gly-Pro-Clp-Gly-Pro-Clp-Gly-
Pro-Clp-Gly-Met-Clp-Gly-Pro-Clp-Gly;

(SEQ ID NO: 231)
Pro-Clp-Gly-Pro-Clp-Gly-Pro-Clp-Gly-Pro-Clp-Gly-
Pro-Clp-Gly-Pro-Met-Gly-Pro-Clp-Gly;

(SEQ ID NO: 232)
Pro-Clp-Gly-Pro-Clp-Gly-Pro-Clp-Gly-Pro-Clp-Gly-
Pro-Clp-Gly-Pro-Clp-Gly-Met-Clp-Gly;

(SEQ ID NO: 233)
Pro-Clp-Gly-Pro-Clp-Gly-Pro-Clp-Gly-Pro-Clp-Gly-
Pro-Clp-Gly-Pro-Clp-Gly-Pro-Met-Gly;

(SEQ ID NO: 234)
Met-Clp-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 235)
Pro-Met-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 236)
Pro-Clp-Gly-Met-Clp-Gly-Pro-Clp-Gly-Pro-Clp-Gly-
Pro-Clp-Gly-Pro-Clp-Gly-Pro-Clp-Gly;

(SEQ ID NO: 237)
Pro-Clp-Gly-Pro-Met-Gly-Pro-Clp-Gly-Pro-Clp-Gly-
Pro-Clp-Gly-Pro-Clp-Gly-Pro-Clp-Gly;

(SEQ ID NO: 238)
Pro-Clp-Gly-Pro-Clp-Gly-Met-Clp-Gly-Pro-Clp-Gly-
Pro-Clp-Gly-Pro-Clp-Gly-Pro-Clp-Gly;

(SEQ ID NO: 239)
Pro-Clp-Gly-Pro-Clp-Gly-Pro-Met-Gly-Pro-Clp-Gly-
Pro-Clp-Gly-Pro-Clp-Gly-Pro-Clp-Gly;

(SEQ ID NO: 240)
Pro-Clp-Gly-Pro-Clp-Gly-Pro-Clp-Gly-Met-Clp-Gly-
Pro-Clp-Gly-Pro-Clp-Gly-Pro-Clp-Gly;

(SEQ ID NO: 241)
Pro-Clp-Gly-Pro-Clp-Gly-Pro-Clp-Gly-Pro-Met-Gly-
Pro-Clp-Gly-Pro-Clp-Gly-Pro-Clp-Gly;

(SEQ ID NO: 242)
Pro-Clp-Gly-Pro-Clp-Gly-Pro-Clp-Gly-Pro-Clp-Gly-
Met-Clp-Gly-Pro-Clp-Gly-Pro-Clp-Gly;

(SEQ ID NO: 243)
Pro-Clp-Gly-Pro-Clp-Gly-Pro-Clp-Gly-Pro-Clp-Gly-
Pro-Met-Gly-Pro-Clp-Gly-Pro-Clp-Gly;

(SEQ ID NO: 244)
Pro-Clp-Gly-Pro-Clp-Gly-Pro-Clp-Gly-Pro-Clp-Gly-
Pro-Clp-Gly-Met-Clp-Gly-Pro-Clp-Gly;

(SEQ ID NO: 245)
Pro-Clp-Gly-Pro-Clp-Gly-Pro-Clp-Gly-Pro-Clp-Gly-
Pro-Clp-Gly-Pro-Met-Gly-Pro-Clp-Gly;

(SEQ ID NO: 246)
Pro-Clp-Gly-Pro-Clp-Gly-Pro-Clp-Gly-Pro-Clp-Gly-
Pro-Clp-Gly-Pro-Clp-Gly-Met-Clp-Gly;

(SEQ ID NO: 247)
Pro-Clp-Gly-Pro-Clp-Gly-Pro-Clp-Gly-Pro-Clp-Gly-
Pro-Clp-Gly-Pro-Clp-Gly-Pro-Met-Gly;

(SEQ ID NO: 248)
Met-Hyp-Gly-Clp-Hyp-Gly-Clp-Hyp-Gly-Clp-Hyp-Gly-
Clp-Hyp-Gly-Clp-Hyp-Gly-Clp-Hyp-Gly;

(SEQ ID NO: 249)
Clp-Met-Gly-Clp-Hyp-Gly-Clp-Hyp-Gly-Clp-Hyp-Gly-
Clp-Hyp-Gly-Clp-Hyp-Gly-Clp-Hyp-Gly;

```
                                               (SEQ ID NO: 250)
Clp-Hyp-Gly-Met-Hyp-Gly-Clp-Hyp-Gly-Clp-Hyp-Gly-
Clp-Hyp-Gly-Clp-Hyp-Gly-Clp-Hyp-Gly;

(SEQ ID NO: 251)
Clp-Hyp-Gly-Clp-Met-Gly-Clp-Hyp-Gly-Clp-Hyp-Gly-
Clp-Hyp-Gly-Clp-Hyp-Gly-Clp-Hyp-Gly;

(SEQ ID NO: 252)
Clp-Hyp-Gly-Clp-Hyp-Gly-Met-Hyp-Gly-Clp-Hyp-Gly-
Clp-Hyp-Gly-Clp-Hyp-Gly-Clp-Hyp-Gly;

(SEQ ID NO: 253)
Clp-Hyp-Gly-Clp-Hyp-Gly-Clp-Met-Gly-Clp-Hyp-Gly-
Clp-Hyp-Gly-Clp-Hyp-Gly-Clp-Hyp-Gly;

(SEQ ID NO: 254)
Clp-Hyp-Gly-Clp-Hyp-Gly-Clp-Hyp-Gly-Met-Hyp-Gly-
Clp-Hyp-Gly-Clp-Hyp-Gly-Clp-Hyp-Gly;

(SEQ ID NO: 255)
Clp-Hyp-Gly-Clp-Hyp-Gly-Clp-Hyp-Gly-Clp-Met-Gly-
Clp-Hyp-Gly-Clp-Hyp-Gly-Clp-Hyp-Gly;

(SEQ ID NO: 256)
Clp-Hyp-Gly-Clp-Hyp-Gly-Clp-Hyp-Gly-Clp-Hyp-Gly-
Met-Hyp-Gly-Clp-Hyp-Gly-Clp-Hyp-Gly;

(SEQ ID NO: 257)
Clp-Hyp-Gly-Clp-Hyp-Gly-Clp-Hyp-Gly-Clp-Hyp-Gly-
Clp-Met-Gly-Clp-Hyp-Gly-Clp-Hyp-Gly;

(SEQ ID NO: 258)
Clp-Hyp-Gly-Clp-Hyp-Gly-Clp-Hyp-Gly-Clp-Hyp-Gly-
Clp-Hyp-Gly-Met-Hyp-Gly-Clp-Hyp-Gly;

(SEQ ID NO: 259)
Clp-Hyp-Gly-Clp-Hyp-Gly-Clp-Hyp-Gly-Clp-Hyp-Gly-
Clp-Hyp-Gly-Clp-Met-Gly-Clp-Hyp-Gly;

(SEQ ID NO: 260)
Clp-Hyp-Gly-Clp-Hyp-Gly-Clp-Hyp-Gly-Clp-Hyp-Gly-
Clp-Hyp-Gly-Clp-Hyp-Gly-Met-Hyp-Gly;
and (SEQ ID NO: 261)
Clp-Hyp-Gly-Clp-Hyp-Gly-Clp-Hyp-Gly-Clp-Hyp-Gly-
Clp-Hyp-Gly-Clp-Hyp-Gly-Clp-Met-Gly.
```

In certain other embodiments of the invention, the collagen mimetic peptide may comprise, consist of or have an amino acid sequence that is or corresponds to a 21-mer of any one of SEQ ID NOs:1-9, in which at least one lysine (Lys) residue has been substituted for at least one of the proline residues in SEQ ID NO: 1, at least one of the hydroxyproline residues in SEQ ID NOs:2-3 and 6, at least one of the fluoroproline residues in SEQ ID NOs:4-6, or at least one of the chloroproline residues in SEQ ID NOs:7-9, yielding, for example, the following sequences:

```
                                               (SEQ ID NO: 262)
Pro-Pro-Gly-Pro-Pro-Gly-Lys-Pro-Gly-Pro-Pro-Gly-
Pro-Pro-Gly-Pro-Pro-Gly-Pro-Pro-Gly;

(SEQ ID NO: 263)
Hyp-Pro-Gly-Hyp-Pro-Gly-Lys-Pro-Gly-Hyp-Pro-Gly-
Hyp-Pro-Gly-Hyp-Pro-Gly-Hyp-Pro-Gly;

(SEQ ID NO: 264)
Pro-Hyp-Gly-Pro-Hyp-Gly-Pro-Lys-Gly-Pro-Hyp-Gly-
Pro-Hyp-Gly-Pro-Hyp-Gly-Pro-Hyp-Gly;

(SEQ ID NO: 265)
Pro-Flp-Gly-Pro-Flp-Gly-Pro-Lys-Gly-Pro-Flp-Gly-
Pro-Flp-Gly-Pro-Flp-Gly-Pro-Flp-Gly;

(SEQ ID NO: 266)
Pro-Clp-Gly-Pro-Clp-Gly-Pro-Lys-Gly-Pro-Clp-Gly-
Pro-Clp-Gly-Pro-Clp-Gly-Pro-Clp-Gly;

(SEQ ID NO: 267)
Lys-Pro-Gly-Pro-Pro-Gly-Pro-Pro-Gly-Pro-Pro-Gly-
Pro-Pro-Gly-Pro-Pro-Gly-Pro-Pro-Gly;

(SEQ ID NO: 268)
Pro-Lys-Gly-Pro-Pro-Gly-Pro-Pro-Gly-Pro-Pro-Gly-
Pro-Pro-Gly-Pro-Pro-Gly-Pro-Pro-Gly;

(SEQ ID NO: 269)
Pro-Pro-Gly-Lys-Pro-Gly-Pro-Pro-Gly-Pro-Pro-Gly-
Pro-Pro-Gly-Pro-Pro-Gly-Pro-Pro-Gly;

(SEQ ID NO: 270)
Pro-Pro-Gly-Pro-Lys-Gly-Pro-Pro-Gly-Pro-Pro-Gly-
Pro-Pro-Gly-Pro-Pro-Gly-Pro-Pro-Gly;

(SEQ ID NO: 271)
Pro-Pro-Gly-Pro-Pro-Gly-Pro-Lys-Gly-Pro-Pro-Gly-
Pro-Pro-Gly-Pro-Pro-Gly-Pro-Pro-Gly;

(SEQ ID NO: 272)
Pro-Pro-Gly-Pro-Pro-Gly-Pro-Pro-Gly-Lys-Pro-Gly-
Pro-Pro-Gly-Pro-Pro-Gly-Pro-Pro-Gly;

(SEQ ID NO: 273)
Pro-Pro-Gly-Pro-Pro-Gly-Pro-Pro-Gly-Pro-Lys-Gly-
Pro-Pro-Gly-Pro-Pro-Gly-Pro-Pro-Gly;

(SEQ ID NO: 274)
Pro-Pro-Gly-Pro-Pro-Gly-Pro-Pro-Gly-Pro-Pro-Gly-
Lys-Pro-Gly-Pro-Pro-Gly-Pro-Pro-Gly;

(SEQ ID NO: 275)
Pro-Pro-Gly-Pro-Pro-Gly-Pro-Pro-Gly-Pro-Pro-Gly-
Pro-Lys-Gly-Pro-Pro-Gly-Pro-Pro-Gly;

(SEQ ID NO: 276)
Pro-Pro-Gly-Pro-Pro-Gly-Pro-Pro-Gly-Pro-Pro-Gly-
Pro-Pro-Gly-Lys-Pro-Gly-Pro-Pro-Gly;

(SEQ ID NO: 277)
Pro-Pro-Gly-Pro-Pro-Gly-Pro-Pro-Gly-Pro-Pro-Gly-
Pro-Pro-Gly-Pro-Lys-Gly-Pro-Pro-Gly;

(SEQ ID NO: 278)
Pro-Pro-Gly-Pro-Pro-Gly-Pro-Pro-Gly-Pro-Pro-Gly-
Pro-Pro-Gly-Pro-Pro-Gly-Lys-Pro-Gly;

(SEQ ID NO: 279)
Pro-Pro-Gly-Pro-Pro-Gly-Pro-Pro-Gly-Pro-Pro-Gly-
Pro-Pro-Gly-Pro-Pro-Gly-Pro-Lys-Gly;

(SEQ ID NO: 280)
Lys-Pro-Gly-Hyp-Pro-Gly-Hyp-Pro-Gly-Hyp-Pro-Gly-
Hyp-Pro-Gly-Hyp-Pro-Gly-Hyp-Pro-Gly;

(SEQ ID NO: 281)
Hyp-Lys-Gly-Hyp-Pro-Gly-Hyp-Pro-Gly-Hyp-Pro-Gly-
Hyp-Pro-Gly-Hyp-Pro-Gly-Hyp-Pro-Gly;

(SEQ ID NO: 282)
Hyp-Pro-Gly-Lys-Pro-Gly-Hyp-Pro-Gly-Hyp-Pro-Gly-
Hyp-Pro-Gly-Hyp-Pro-Gly-Hyp-Pro-Gly;

(SEQ ID NO: 283)
Hyp-Pro-Gly-Hyp-Lys-Gly-Hyp-Pro-Gly-Hyp-Pro-Gly-
Hyp-Pro-Gly-Hyp-Pro-Gly-Hyp-Pro-Gly;

(SEQ ID NO: 284)
Hyp-Pro-Gly-Hyp-Pro-Gly-Lys-Pro-Gly-Hyp-Pro-Gly-
Hyp-Pro-Gly-Hyp-Pro-Gly-Hyp-Pro-Gly;

(SEQ ID NO: 285)
Hyp-Pro-Gly-Hyp-Pro-Gly-Hyp-Pro-Gly-Lys-Pro-Gly-
Hyp-Pro-Gly-Hyp-Pro-Gly-Hyp-Pro-Gly;
```

(SEQ ID NO: 286)
Hyp-Pro-Gly-Hyp-Pro-Gly-Hyp-Pro-Gly-Hyp-Lys-Gly-
Hyp-Pro-Gly-Hyp-Pro-Gly-Hyp-Pro-Gly;

(SEQ ID NO: 287)
Hyp-Pro-Gly-Hyp-Pro-Gly-Hyp-Pro-Gly-Hyp-Pro-Gly-
Lys-Pro-Gly-Hyp-Pro-Gly-Hyp-Pro-Gly;

(SEQ ID NO: 288)
Hyp-Pro-Gly-Hyp-Pro-Gly-Hyp-Pro-Gly-Hyp-Pro-Gly-
Hyp-Lys-Gly-Hyp-Pro-Gly-Hyp-Pro-Gly;

(SEQ ID NO: 289)
Hyp-Pro-Gly-Hyp-Pro-Gly-Hyp-Pro-Gly-Hyp-Pro-Gly-
Hyp-Pro-Gly-Lys-Pro-Gly-Hyp-Pro-Gly;

(SEQ ID NO: 290)
Hyp-Pro-Gly-Hyp-Pro-Gly-Hyp-Pro-Gly-Hyp-Pro-Gly-
Hyp-Pro-Gly-Hyp-Lys-Gly-Hyp-Pro-Gly;

(SEQ ID NO: 291)
Hyp-Pro-Gly-Hyp-Pro-Gly-Hyp-Pro-Gly-Hyp-Pro-Gly-
Hyp-Pro-Gly-Hyp-Pro-Gly-Lys-Pro-Gly;

(SEQ ID NO: 292)
Hyp-Pro-Gly-Hyp-Pro-Gly-Hyp-Pro-Gly-Hyp-Pro-Gly-
Hyp-Pro-Gly-Hyp-Pro-Gly-Hyp-Lys-Gly;

(SEQ ID NO: 293)
Lys-Hyp-Gly-Pro-Hyp-Gly-Pro-Hyp-Gly-Pro-Hyp-Gly-
Pro-Hyp-Gly-Pro-Hyp-Gly-Pro-Hyp-Gly;

(SEQ ID NO: 294)
Pro-Lys-Gly-Pro-Hyp-Gly-Pro-Hyp-Gly-Pro-Hyp-Gly-
Pro-Hyp-Gly-Pro-Hyp-Gly-Pro-Hyp-Gly;

(SEQ ID NO: 295)
Pro-Hyp-Gly-Lys-Hyp-Gly-Pro-Hyp-Gly-Pro-Hyp-Gly-
Pro-Hyp-Gly-Pro-Hyp-Gly-Pro-Hyp-Gly;

(SEQ ID NO: 296)
Pro-Hyp-Gly-Pro-Lys-Gly-Pro-Hyp-Gly-Pro-Hyp-Gly-
Pro-Hyp-Gly-Pro-Hyp-Gly-Pro-Hyp-Gly;

(SEQ ID NO: 297)
Pro-Hyp-Gly-Pro-Hyp-Gly-Lys-Hyp-Gly-Pro-Hyp-Gly-
Pro-Hyp-Gly-Pro-Hyp-Gly-Pro-Hyp-Gly;

(SEQ ID NO: 298)
Pro-Hyp-Gly-Pro-Hyp-Gly-Pro-Hyp-Gly-Lys-Hyp-Gly-
Pro-Hyp-Gly-Pro-Hyp-Gly-Pro-Hyp-Gly;

(SEQ ID NO: 299)
Pro-Hyp-Gly-Pro-Hyp-Gly-Pro-Hyp-Gly-Pro-Lys-Gly-
Pro-Hyp-Gly-Pro-Hyp-Gly-Pro-Hyp-Gly;

(SEQ ID NO: 300)
Pro-Hyp-Gly-Pro-Hyp-Gly-Pro-Hyp-Gly-Pro-Hyp-Gly-
Lys-Hyp-Gly-Pro-Hyp-Gly-Pro-Hyp-Gly;

(SEQ ID NO: 301)
Pro-Hyp-Gly-Pro-Hyp-Gly-Pro-Hyp-Gly-Pro-Hyp-Gly-
Pro-Lys-Gly-Pro-Hyp-Gly-Pro-Hyp-Gly;

(SEQ ID NO: 302)
Pro-Hyp-Gly-Pro-Hyp-Gly-Pro-Hyp-Gly-Pro-Hyp-Gly-
Pro-Hyp-Gly-Lys-Hyp-Gly-Pro-Hyp-Gly;

(SEQ ID NO: 303)
Pro-Hyp-Gly-Pro-Hyp-Gly-Pro-Hyp-Gly-Pro-Hyp-Gly-
Pro-Hyp-Gly-Pro-Lys-Gly-Pro-Hyp-Gly;

(SEQ ID NO: 304)
Pro-Hyp-Gly-Pro-Hyp-Gly-Pro-Hyp-Gly-Pro-Hyp-Gly-
Pro-Hyp-Gly-Pro-Hyp-Gly-Lys-Hyp-Gly;

(SEQ ID NO: 305)
Pro-Hyp-Gly-Pro-Hyp-Gly-Pro-Hyp-Gly-Pro-Hyp-Gly-
Pro-Hyp-Gly-Pro-Hyp-Gly-Pro-Lys-Gly;

(SEQ ID NO: 306)
Lys-Flp-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 307)
Pro-Lys-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 308)
Pro-Flp-Gly-Lys-Flp-Gly-Pro-Flp-Gly-Pro-Flp-Gly-
Pro-Flp-Gly-Pro-Flp-Gly-Pro-Flp-Gly;

(SEQ ID NO: 309)
Pro-Flp-Gly-Pro-Lys-Gly-Pro-Flp-Gly-Pro-Flp-Gly-
Pro-Flp-Gly-Pro-Flp-Gly-Pro-Flp-Gly;

(SEQ ID NO: 310)
Pro-Flp-Gly-Pro-Flp-Gly-Lys-Flp-Gly-Pro-Flp-Gly-
Pro-Flp-Gly-Pro-Flp-Gly-Pro-Flp-Gly;

(SEQ ID NO: 311)
Pro-Flp-Gly-Pro-Flp-Gly-Pro-Flp-Gly-Lys-Flp-Gly-
Pro-Flp-Gly-Pro-Flp-Gly-Pro-Flp-Gly;

(SEQ ID NO: 312)
Pro-Flp-Gly-Pro-Flp-Gly-Pro-Flp-Gly-Pro-Lys-Gly-
Pro-Flp-Gly-Pro-Flp-Gly-Pro-Flp-Gly;

(SEQ ID NO: 313)
Pro-Flp-Gly-Pro-Flp-Gly-Pro-Flp-Gly-Pro-Flp-Gly-
Lys-Flp-Gly-Pro-Flp-Gly-Pro-Flp-Gly;

(SEQ ID NO: 314)
Pro-Flp-Gly-Pro-Flp-Gly-Pro-Flp-Gly-Pro-Flp-Gly-
Pro-Lys-Gly-Pro-Flp-Gly-Pro-Flp-Gly;

(SEQ ID NO: 315)
Pro-Flp-Gly-Pro-Flp-Gly-Pro-Flp-Gly-Pro-Flp-Gly-
Pro-Flp-Gly-Lys-Flp-Gly-Pro-Flp-Gly;

(SEQ ID NO: 316)
Pro-Flp-Gly-Pro-Flp-Gly-Pro-Flp-Gly-Pro-Flp-Gly-
Pro-Flp-Gly-Pro-Lys-Gly-Pro-Flp-Gly;

(SEQ ID NO: 317)
Pro-Flp-Gly-Pro-Flp-Gly-Pro-Flp-Gly-Pro-Flp-Gly-
Pro-Flp-Gly-Pro-Flp-Gly-Lys-Flp-Gly;

(SEQ ID NO: 318)
Pro-Flp-Gly-Pro-Flp-Gly-Pro-Flp-Gly-Pro-Flp-Gly-
Pro-Flp-Gly-Pro-Flp-Gly-Pro-Lys-Gly;

(SEQ ID NO: 319)
Lys-Flp-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 320)
Pro-Lys-Gly-Pro-Flp-Gly-Pro-Flp-Gly-Pro-Flp-Gly-
Pro-Flp-Gly-Pro-Flp-Gly-Pro-Flp-Gly;

(SEQ ID NO: 321)
Pro-Flp-Gly-Lys-Flp-Gly-Pro-Flp-Gly-Pro-Flp-Gly-
Pro-Flp-Gly-Pro-Flp-Gly-Pro-Flp-Gly;

(SEQ ID NO: 322)
Pro-Flp-Gly-Pro-Lys-Gly-Pro-Flp-Gly-Pro-Flp-Gly-
Pro-Flp-Gly-Pro-Flp-Gly-Pro-Flp-Gly;

(SEQ ID NO: 323)
Pro-Flp-Gly-Pro-Flp-Gly-Lys-Flp-Gly-Pro-Flp-Gly-
Pro-Flp-Gly-Pro-Flp-Gly-Pro-Flp-Gly;

(SEQ ID NO: 324)
Pro-Flp-Gly-Pro-Flp-Gly-Pro-Lys-Gly-Pro-Flp-Gly-
Pro-Flp-Gly-Pro-Flp-Gly-Pro-Flp-Gly;

(SEQ ID NO: 325)
Pro-Flp-Gly-Pro-Flp-Gly-Pro-Flp-Gly-Lys-Flp-Gly-
Pro-Flp-Gly-Pro-Flp-Gly-Pro-Flp-Gly;

(SEQ ID NO: 326)
Pro-Flp-Gly-Pro-Flp-Gly-Pro-Flp-Gly-Pro-Lys-
Pro-Flp-Gly-Pro-Flp-Gly-Pro-Flp-Gly;

(SEQ ID NO: 327)
Pro-Flp-Gly-Pro-Flp-Gly-Pro-Flp-Gly-Pro-Flp-Gly-
Lys-Flp-Gly-Pro-Flp-Gly-Pro-Flp-Gly;

(SEQ ID NO: 328)
Pro-Flp-Gly-Pro-Flp-Gly-Pro-Flp-Gly-Pro-Flp-Gly-
Pro-Lys-Gly-Pro-Flp-Gly-Pro-Flp-Gly;

(SEQ ID NO: 329)
Pro-Flp-Gly-Pro-Flp-Gly-Pro-Flp-Gly-Pro-Flp-Gly-
Pro-Flp-Gly-Lys-Flp-Gly-Pro-Flp-Gly;

(SEQ ID NO: 330)
Pro-Flp-Gly-Pro-Flp-Gly-Pro-Flp-Gly-Pro-Flp-Gly-
Pro-Flp-Gly-Pro-Lys-Gly-Pro-Flp-Gly;

(SEQ ID NO: 331)
Pro-Flp-Gly-Pro-Flp-Gly-Pro-Flp-Gly-Pro-Flp-Gly-
Pro-Flp-Gly-Pro-Flp-Gly-Lys-Flp-Gly;

(SEQ ID NO: 332)
Pro-Flp-Gly-Pro-Flp-Gly-Pro-Flp-Gly-Pro-Flp-Gly-
Pro-Flp-Gly-Pro-Flp-Gly-Pro-Lys-Gly;

(SEQ ID NO: 333)
Lys-Hyp-Gly-Flp-Hyp-Gly-Flp-Hyp-Gly-Flp-Hyp-Gly-
Flp-Hyp-Gly-Flp-Hyp-Gly-Flp-Hyp-Gly;

(SEQ ID NO: 334)
Flp-Lys-Gly-Flp-Hyp-Gly-Flp-Hyp-Gly-Flp-Hyp-Gly-
Flp-Hyp-Gly-Flp-Hyp-Gly-Flp-Hyp-Gly;

(SEQ ID NO: 335)
Flp-Hyp-Gly-Lys-Hyp-Gly-Flp-Hyp-Gly-Flp-Hyp-Gly-
Flp-Hyp-Gly-Flp-Hyp-Gly-Flp-Hyp-Gly;

(SEQ ID NO: 336)
Flp-Hyp-Gly-Flp-Lys-Gly-Flp-Hyp-Gly-Flp-Hyp-Gly-
Flp-Hyp-Gly-Flp-Hyp-Gly-Flp-Hyp-Gly;

(SEQ ID NO: 337)
Flp-Hyp-Gly-Flp-Hyp-Gly-Lys-Hyp-Gly-Flp-Hyp-Gly-
Flp-Hyp-Gly-Flp-Hyp-Gly-Flp-Hyp-Gly;

(SEQ ID NO: 338)
Flp-Hyp-Gly-Flp-Hyp-Gly-Flp-Lys-Gly-Flp-Hyp-Gly-
Flp-Hyp-Gly-Flp-Hyp-Gly-Flp-Hyp-Gly;

(SEQ ID NO: 339)
Flp-Hyp-Gly-Flp-Hyp-Gly-Flp-Hyp-Gly-Lys-Hyp-Gly-
Flp-Hyp-Gly-Flp-Hyp-Gly-Flp-Hyp-Gly;

(SEQ ID NO: 340)
Flp-Hyp-Gly-Flp-Hyp-Gly-Flp-Hyp-Gly-Flp-Lys-Gly-
Flp-Hyp-Gly-Flp-Hyp-Gly-Flp-Hyp-Gly;

(SEQ ID NO: 341)
Flp-Hyp-Gly-Flp-Hyp-Gly-Flp-Hyp-Gly-Flp-Hyp-Gly-
Lys-Hyp-Gly-Flp-Hyp-Gly-Flp-Hyp-Gly;

(SEQ ID NO: 342)
Flp-Hyp-Gly-Flp-Hyp-Gly-Flp-Hyp-Gly-Flp-Hyp-Gly-
Flp-Lys-Gly-Flp-Hyp-Gly-Flp-Hyp-Gly;

(SEQ ID NO: 343)
Flp-Hyp-Gly-Flp-Hyp-Gly-Flp-Hyp-Gly-Flp-Hyp-Gly-
Flp-Hyp-Gly-Lys-Hyp-Gly-Flp-Hyp-Gly;

(SEQ ID NO: 344)
Flp-Hyp-Gly-Flp-Hyp-Gly-Flp-Hyp-Gly-Flp-Hyp-Gly-
Flp-Hyp-Gly-Flp-Lys-Gly-Flp-Hyp-Gly;

(SEQ ID NO: 345)
Flp-Hyp-Gly-Flp-Hyp-Gly-Flp-Hyp-Gly-Flp-Hyp-Gly-
Flp-Hyp-Gly-Flp-Hyp-Gly-Lys-Hyp-Gly;

(SEQ ID NO: 346)
Flp-Hyp-Gly-Flp-Hyp-Gly-Flp-Hyp-Gly-Flp-Hyp-Gly-
Flp-Hyp-Gly-Flp-Hyp-Gly-Flp-Lys-Gly;

(SEQ ID NO: 347)
Lys-Clp-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 348)
Pro-Lys-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 349)
Pro-Clp-Gly-Lys-Clp-Gly-Pro-Clp-Gly-Pro-Clp-Gly-
Pro-Clp-Gly-Pro-Clp-Gly-Pro-Clp-Gly;

(SEQ ID NO: 350)
Pro-Clp-Gly-Pro-Lys-Gly-Pro-Clp-Gly-Pro-Clp-Gly-
Pro-Clp-Gly-Pro-Clp-Gly-Pro-Clp-Gly;

(SEQ ID NO: 351)
Pro-Clp-Gly-Pro-Clp-Gly-Lys-Clp-Gly-Pro-Clp-Gly-
Pro-Clp-Gly-Pro-Clp-Gly-Pro-Clp-Gly;

(SEQ ID NO: 352)
Pro-Clp-Gly-Pro-Clp-Gly-Pro-Clp-Gly-Lys-Clp-Gly-
Pro-Clp-Gly-Pro-Clp-Gly-Pro-Clp-Gly;

(SEQ ID NO: 353)
Pro-Clp-Gly-Pro-Clp-Gly-Pro-Clp-Gly-Pro-Lys-Gly-
Pro-Clp-Gly-Pro-Clp-Gly-Pro-Clp-Gly;

(SEQ ID NO: 354)
Pro-Clp-Gly-Pro-Clp-Gly-Pro-Clp-Gly-Pro-Clp-Gly-
Lys-Clp-Gly-Pro-Clp-Gly-Pro-Clp-Gly;

(SEQ ID NO: 355)
Pro-Clp-Gly-Pro-Clp-Gly-Pro-Clp-Gly-Pro-Clp-Gly-
Pro-Lys-Gly-Pro-Clp-Gly-Pro-Clp-Gly;

(SEQ ID NO: 356)
Pro-Clp-Gly-Pro-Clp-Gly-Pro-Clp-Gly-Pro-Clp-Gly-
Pro-Clp-Gly-Lys-Clp-Gly-Pro-Clp-Gly;

(SEQ ID NO: 357)
Pro-Clp-Gly-Pro-Clp-Gly-Pro-Clp-Gly-Pro-Clp-Gly-
Pro-Clp-Gly-Pro-Lys-Gly-Pro-Clp-Gly;

(SEQ ID NO: 358)
Pro-Clp-Gly-Pro-Clp-Gly-Pro-Clp-Gly-Pro-Clp-Gly-
Pro-Clp-Gly-Pro-Clp-Gly-Lys-Clp-Gly;

(SEQ ID NO: 359)
Pro-Clp-Gly-Pro-Clp-Gly-Pro-Clp-Gly-Pro-Clp-Gly-
Pro-Clp-Gly-Pro-Clp-Gly-Pro-Lys-Gly;

(SEQ ID NO: 360)
Lys-Clp-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 361)
Pro-Lys-Gly-Pro-Clp-Gly-Pro-Clp-Gly-Pro-Clp-Gly-
Pro-Clp-Gly-Pro-Clp-Gly-Pro-Clp-Gly;

(SEQ ID NO: 362)
Pro-Clp-Gly-Lys-Clp-Gly-Pro-Clp-Gly-Pro-Clp-Gly-
Pro-Clp-Gly-Pro-Clp-Gly-Pro-Clp-Gly;

(SEQ ID NO: 363)
Pro-Clp-Gly-Pro-Lys-Gly-Pro-Clp-Gly-Pro-Clp-Gly-
Pro-Clp-Gly-Pro-Clp-Gly-Pro-Clp-Gly;

(SEQ ID NO: 364)
Pro-Clp-Gly-Pro-Clp-Gly-Lys-Clp-Gly-Pro-Clp-Gly-
Pro-Clp-Gly-Pro-Clp-Gly-Pro-Clp-Gly;

(SEQ ID NO: 365)
Pro-Clp-Gly-Pro-Clp-Gly-Pro-Lys-Gly-Pro-Clp-Gly-
Pro-Clp-Gly-Pro-Clp-Gly-Pro-Clp-Gly;

(SEQ ID NO: 366)
Pro-Clp-Gly-Pro-Clp-Gly-Pro-Clp-Gly-Lys-Clp-Gly-
Pro-Clp-Gly-Pro-Clp-Gly-Pro-Clp-Gly;

(SEQ ID NO: 367)
Pro-Clp-Gly-Pro-Clp-Gly-Pro-Clp-Gly-Pro-Lys-Gly-
Pro-Clp-Gly-Pro-Clp-Gly-Pro-Clp-Gly;

(SEQ ID NO: 368)
Pro-Clp-Gly-Pro-Clp-Gly-Pro-Clp-Gly-Pro-Clp-Gly-
Lys-Clp-Gly-Pro-Clp-Gly-Pro-Clp-Gly;

(SEQ ID NO: 369)
Pro-Clp-Gly-Pro-Clp-Gly-Pro-Clp-Gly-Pro-Clp-Gly-
Pro-Lys-Gly-Pro-Clp-Gly-Pro-Clp-Gly;

(SEQ ID NO: 370)
Pro-Clp-Gly-Pro-Clp-Gly-Pro-Clp-Gly-Pro-Clp-Gly-
Pro-Clp-Gly-Lys-Clp-Gly-Pro-Clp-Gly;

(SEQ ID NO: 371)
Pro-Clp-Gly-Pro-Clp-Gly-Pro-Clp-Gly-Pro-Clp-Gly-
Pro-Clp-Gly-Pro-Lys-Gly-Pro-Clp-Gly;

(SEQ ID NO: 372)
Pro-Clp-Gly-Pro-Clp-Gly-Pro-Clp-Gly-Pro-Clp-Gly-
Pro-Clp-Gly-Pro-Clp-Gly-Lys-Clp-Gly;

(SEQ ID NO: 373)
Pro-Clp-Gly-Pro-Clp-Gly-Pro-Clp-Gly-Pro-Clp-Gly-
Pro-Clp-Gly-Pro-Clp-Gly-Pro-Lys-Gly;

(SEQ ID NO: 374)
Lys-Hyp-Gly-Clp-Hyp-Gly-Clp-Hyp-Gly-Clp-Hyp-Gly-
Clp-Hyp-Gly-Clp-Hyp-Gly-Clp-Hyp-Gly;

(SEQ ID NO: 375)
Clp-Lys-Gly-Clp-Hyp-Gly-Clp-Hyp-Gly-Clp-Hyp-Gly-
Clp-Hyp-Gly-Clp-Hyp-Gly-Clp-Hyp-Gly;

(SEQ ID NO: 376)
Clp-Hyp-Gly-Lys-Hyp-Gly-Clp-Hyp-Gly-Clp-Hyp-Gly-
Clp-Hyp-Gly-Clp-Hyp-Gly-Clp-Hyp-Gly;

(SEQ ID NO: 377)
Clp-Hyp-Gly-Clp-Lys-Gly-Clp-Hyp-Gly-Clp-Hyp-Gly-
Clp-Hyp-Gly-Clp-Hyp-Gly-Clp-Hyp-Gly;

(SEQ ID NO: 378)
Clp-Hyp-Gly-Clp-Hyp-Gly-Lys-Hyp-Gly-Clp-Hyp-Gly-
Clp-Hyp-Gly-Clp-Hyp-Gly-Clp-Hyp-Gly;

(SEQ ID NO: 379)
Clp-Hyp-Gly-Clp-Hyp-Gly-Clp-Lys-Gly-Clp-Hyp-Gly-
Clp-Hyp-Gly-Clp-Hyp-Gly-Clp-Hyp-Gly;

(SEQ ID NO: 380)
Clp-Hyp-Gly-Clp-Hyp-Gly-Clp-Hyp-Gly-Lys-Hyp-Gly-
Clp-Hyp-Gly-Clp-Hyp-Gly-Clp-Hyp-Gly;

(SEQ ID NO: 381)
Clp-Hyp-Gly-Clp-Hyp-Gly-Clp-Hyp-Gly-Clp-Lys-Gly-
Clp-Hyp-Gly-Clp-Hyp-Gly-Clp-Hyp-Gly;

(SEQ ID NO: 382)
Clp-Hyp-Gly-Clp-Hyp-Gly-Clp-Hyp-Gly-Clp-Hyp-Gly-
Lys-Hyp-Gly-Clp-Hyp-Gly-Clp-Hyp-Gly;

(SEQ ID NO: 383)
Clp-Hyp-Gly-Clp-Hyp-Gly-Clp-Hyp-Gly-Clp-Hyp-Gly-
Clp-Lys-Gly-Clp-Hyp-Gly-Clp-Hyp-Gly;

(SEQ ID NO: 384)
Clp-Hyp-Gly-Clp-Hyp-Gly-Clp-Hyp-Gly-Clp-Hyp-Gly-
Clp-Hyp-Gly-Lys-Hyp-Gly-Clp-Hyp-Gly;

(SEQ ID NO: 385)
Clp-Hyp-Gly-Clp-Hyp-Gly-Clp-Hyp-Gly-Clp-Hyp-Gly-
Clp-Hyp-Gly-Clp-Lys-Gly-Clp-Hyp-Gly;

(SEQ ID NO: 386)
Clp-Hyp-Gly-Clp-Hyp-Gly-Clp-Hyp-Gly-Clp-Hyp-Gly-
Clp-Hyp-Gly-Clp-Hyp-Gly-Lys-Hyp-Gly;
and (SEQ ID NO: 387)
Clp-Hyp-Gly-Clp-Hyp-Gly-Clp-Hyp-Gly-Clp-Hyp-Gly-
Clp-Hyp-Gly-Clp-Hyp-Gly-Clp-Lys-Gly.

Preferred CMPs according to this aspect of the invention include CMPs having amino acid sequences corresponding to SEQ ID NOs:1-14, 66-94, 107-135, 136-140, 192-220, 233-261, 260-264, 280, 281, 293, 294, 306, 307, 318-346, 347, 348, and 359-387. Particularly preferred are CMPs having amino acid sequences corresponding to SEQ ID NOs: 1, 6, 9, 10-27, 81-94, 122-135, 207-220, 248-261, 333-346 and 374-387. Even more particularly preferred are CMPs having amino acid sequences corresponding to SEQ ID NOs: 1, 6 and 9 (for CMPs that are not to be directly conjugated to one or more pharmaceutically active ingredients or biologics), and CMPs having amino acid sequences corresponding to SEQ ID NOs: 10-27, 81-94, 122-135, 207-220, 248-261, 333-346 and 374-387 (for CMPs that are to be directly conjugated to one or more pharmaceutically active ingredients or biologics). It will be understood by those of ordinary skill, of course, based on knowledge in the art and the teachings herein, that such CMPs may comprise two or more cysteine, methionine and/or lysine residues, in which at least one additional cysteine, methionine and/or lysine residue, or any combination thereof, may be substituted for at least one proline residue, at least one hydroxyproline residue, at least one fluoroproline residue and/or at least one chloroproline residue in any of the foregoing CMP sequences that comprise at least one proline, at least one hydroxyproline, at least one fluoroproline and/or at least one chloroproline residue. It also will be appreciated by those of ordinary skill in the art based on the teachings herein and information readily available in the art that other combinations of amino acid substitutions are also possible and within the scope of the present invention.

The CMPs described herein are suitable for a variety of purposes. For example, as described in further detail elsewhere herein, the CMPs may be used in a variety of therapeutic applications or preventative applications by being directly applied to or introduced into the body of a human or veterinary animal, particularly at sites of collagen disruption or potential collagen disruption, where the CMPs described herein will localize directly to the site of collagen disruption, anneal to disrupted collagen strands and stabilize the collagen structure such that it resists further disruption, and in some cases reform a native collagen triple helix in the site of collagen disruption. Such applications are useful in promoting the repair and strengthening of disrupted collagen in sites of injury or potential injury or disruption, for example in wounds or disorders (e.g., scarring, wrinkle formation, etc.) involving skin, tendon, ligament, cartilage, bone and other collagen-containing structures and organs. The CMPs described herein also are useful in providing biocompatible coatings for certain medical devices, to promote the healing of injuries and disorders in areas of the body where such devices are used in treating or preventing certain diseases, disorders and structural abnormalities or injuries in humans and veterinary animals, particularly those in which such diseases, disorders and structural abnormalities or injuries involve disruption of collagen and/or collagen-containing structures. The CMPs described herein also are useful in providing a unique delivery vehicle suitable for delivering a variety of therapeutic compounds, compositions and medicaments to sites of disease, disorder and structural abnormality or injury in humans and veterinary animals, particularly for use in treating, preventing or ameliorating diseases, disorders, medical conditions and structural abnormalities or injuries in which collagen disruption is either the cause of, is associated with, or is colocalized with the site of the disease, disorder and structural abnormality or injury. Other suitable uses of the CMPs described herein and used in certain aspects of the present invention will be readily apparent to the ordinarily skilled artisan based on the disclosure herein and information that is readily available in the art.

In certain embodiments, the CMPs described herein are suitable for formation into a film, wafer, membrane or gel comprising one or more of the CMPs in a form suitable for introduction or implantation into a human or animal for therapeutic, preventative or diagnostic applications such as those described herein and others that will be familiar to those of ordinary skill in the relevant arts. For example, films, wafers, membranes, spheres, nanoparticles or gels can be formed from a solution of one or more of the CMPs described herein using methods such as those described in U.S. Pat. Nos. 6,197,934; 6,448,378; and 9,289,396; the disclosures of all of which are incorporated herein by reference in their entireties. Alternatively, films, wafers, membranes spheres, nanoparticles, or gels can be formed from other materials, such as atelocollagen (see U.S. Pat. Nos. 6,197,934; 6,448,378; and 9,289,396), copolymers of poly(lactic acid) and poly(glycoloic acid) (PLGA) (see Bala, I., et al., Crit. Rev. Ther. Drug Carrier Syst. 21(5):387-422 (2004)), and other materials that are known to those of ordinary skill in the art (see, e.g., Kumar, V., et al., eds., "Polymer Gels: Perspectives and Applications", ISBN 978-981-10-6079-3, Singapore: Springer (2018)), and one or more of the CMPs can be suitably incorporated into such films, wafers, membranes, spheres, nanoparticles, gels, etc., during the formation thereof by including the CMPs in the solution, at concentrations of about 1%-99%, about 2%-95%, about 3%-90%, about 4%-90%, about 5%-90%, about 10%-90%, about 15%-90%, about 20%-90%, about 25%-90%, about 25%-85%, about 25%-75%, about 25%-50%, about 35%-50%, and the like. Suitable other amounts or concentrations of the CMPs described herein that can be suitably included in the solutions during formation of the films, wafers, membranes, spheres, nanoparticles, gels, etc., will be readily apparent from the teachings herein and from information readily available in the art to the ordinarily skilled artisan. In certain such embodiments, one or more therapeutic compounds described herein, and/or one or more CMP-TC conjugates described herein, can be suitably incorporated into the solution from which the films, wafers, membranes, spheres, nanoparticles, gels, etc., are formed. Alternatively, in related aspects, one or more films, wafers, membranes, spheres, nanoparticles, gels, etc., once formed as described above, can be treated or coated with one or more CMPs and/or CMP-TC conjugates described herein, by immersing the films, wafers, membranes, spheres, nanoparticles, gels, etc., in a solution, particularly a buffered aqueous solution, containing a suitable amount or concentration (such as those described herein) of one or more CMPs or CMP-TC conjugates described herein, and then drying the films, wafers, membranes, etc., prior to use in therapeutic, preventative or diagnostic methods such as those described herein.

Attachment/Conjugation of CMPs

In certain embodiments of the invention, the CMPs described herein are suitably attached or conjugated to one or more therapeutic or diagnostic compounds, to produce CMP conjugate compounds. In such embodiments of the invention, the CMP-therapeutic compound or CMP-diagnostic compound conjugate compounds can then be introduced into the body of a human or veterinary animal, in methods of treating and/or preventing and/or diagnosing certain diseases, disorders and structural abnormalities in humans or veterinary animals suffering therefrom. Accordingly, in certain embodiments the present invention also provides the use of the CMPs described herein attached or conjugated to one or more therapeutic compounds to produce conjugated CMPs, compositions comprising such conjugated CMPs (which may optionally comprise one or more additional therapeutic or pharmaceutically active ingredients), methods of producing such conjugates and methods of using such conjugates and compositions in the treatment, prevention and diagnosis of a variety of diseases, disorders and medical conditions in humans and veterinary animals.

Conjugates of CMPs and at least one therapeutic compound (which may be described herein as "CMP-TC conjugates") according to this aspect of the invention will comprise at least one CMP described herein attached to at least one therapeutic compound to form a CMP-TC conjugate. CMPs suitably used in such aspects of the invention include any of those described herein, including CMPs having an amino acid sequence corresponding to any one of SEQ ID NOs:1-387 and particularly wherein the CMPs have an amino acid sequence corresponding to any one of SEQ ID NOs: 1-14, 66-94, 107-135, 136-140, 192-220, 233-261, 260-264, 280, 281, 293, 294, 306, 307, 318-346, 347, 348, and 359-387, and more particularly CMPs having amino acid sequences corresponding to SEQ ID NOs:10-27, 81-94, 122-135, 207-220, 248-261, 333-346 and 374-387. Other suitable CMP sequences will be immediately apparent to one of ordinary skill in the art based on the teachings contained herein. For example, a CMP having at least one, and in some cases more than one, cysteine, methionine or lysine residue substituted in place of at least one, and in some cases more than one, proline, hydroxyproline, fluoroproline or chloroproline residue in SEQ ID NOs: 1-9, will be particularly suitable for use in producing the CMP-TC conjugates provided by and used in the present invention. Examples of such suitable CMPs include those having amino acid sequences corresponding to SEQ ID NOs: 10-27, 81-94, 122-135, 207-220, 248-261, 333-346 and 374-387.

Methods of preparing the CMPs and CMP-TCs described herein and provided and used in the present invention will be familiar to those of ordinary skill in the art based on the teachings herein and information that is readily available in the art. For example, CMPs can be synthesized using standard protein/peptide synthesis techniques such as those described in U.S. Pat. Nos. 5,973,112; 7,122,521; and 7,858,741; as well as in U.S. Patent Publ. No. US 2007/0275897 A1, the disclosures of all of which are incorporated herein by reference in their entireties. Synthesis of CMPs can also be accomplished by purchasing custom-synthesized CMPs produced commercially, for example by Bachem (Torrance, Calif., USA) and RS Synthesis (Louisville, Ky., USA). In other embodiments, synthesis of CMPs can be accomplished using genetic engineering and recombinant expression of the CMPs from prokaryotic or eukaryotic expression systems (see, e.g., Buechter, D. D., et al., J. Biol. Chem. 278(1):645-650 (2003)).

In synthesizing the peptides described herein, in certain embodiments it is preferred that certain stereochemistries be used for the amino acid substitutions, particularly if hydroxyproline, fluoroproline or chloroproline are used:

(1) if hydroxyproline is substituted in place of proline in the Xaa position of the Xaa-Yaa-Gly trimer noted hereinabove, in certain embodiments the hydroxyproline has a (2R, 4S) stereochemistry, or a cis or trans, and preferably a cis, stereochemistry;

(2) if hydroxyproline is substituted in place of proline in the Yaa position of the Xaa-Yaa-Gly trimer noted hereinabove, in certain embodiments the hydroxyproline has a (2R, 4S) stereochemistry, or a cis or trans, and preferably a cis, stereochemistry;

(3) if fluoroproline is substituted in place of proline in the Yaa position of the Xaa-Yaa-Gly trimer noted hereinabove, in certain embodiments the hydroxyproline has a (2R, 4S) stereochemistry, or a cis or trans, and preferably a cis, stereochemistry; and (4) if chloroproline is substituted in place of proline in the Yaa position of the Xaa-Yaa-Gly trimer noted hereinabove, in certain embodiments the hydroxyproline has a (2R, 4S) stereochemistry, or a cis or trans, and preferably a cis, stereochemistry.

Other suitable stereochemistries can be determined empirically without having to resort to undue experimentation, and will be immediately apparent to those of ordinary skill in the art. As noted above, certain CMPs provided by and used in the present invention may contain one or more additional substitutions, for example one or more cysteine residues and/or one or more methionine residues, in place of one or more prolines in a given CMP multimer. Such substitutions are suitably accomplished by adding those residues to the growing CMP peptide chain during the synthetic process using standard peptide synthetic methods such as those described elsewhere herein and those that are known in the art.

Once the CMPs have been prepared, they are suitably used in producing the CMP-TCs of the invention, i.e., the therapeutic or diagnostic compositions of the invention, by attaching one or more therapeutic compounds to the CMPs. In certain embodiments, the CMP-TCs of the invention can be prepared a method comprising (a) providing a collagen mimetic peptide having an amino acid sequence corresponding to any one of SEQ ID NOs: 1-387, particularly CMPs have an amino acid sequence corresponding to any one of SEQ ID NOs:1-14, 66-94, 107-135, 136-140, 192-220, 233-261, 260-264, 280, 281, 293, 294, 306, 307, 318-346, 347, 348, and 359-387, and more particularly CMPs having amino acid sequences corresponding to SEQ ID NOs:10-27, 81-94, 122-135, 207-220, 248-261, 333-346 and 374-387; (b) providing at least one therapeutic or diagnostic compound suitable to be conjugated to the CMP; and (c) attaching the therapeutic or diagnostic compound directly or indirectly to the CMP. In certain cases, particularly wherein the therapeutic compound is a small peptide biologic compound, the therapeutic compound can be directly attached to the CMP via a peptide bond, for example by simply extending the synthesis of the peptide beyond the carboxy terminus of the CMP and attaching the amino terminal amino acid of the therapeutic compound to the carboxy terminal amino acid of the CMP via a peptide bond. One example of such a CMP-TC is a peptide conjugate in which the wound healing peptide known as Substance P and having an amino acid sequence of Arg-Pro-Lys-Pro-Gln-Gln-Phe-Phe-Gly-Leu-Met (SEQ ID NO:388), is attached to a CMP described herein. Examples of such conjugates include, for example:

```
                                              (SEQ ID NO: 389)
Pro-Pro-Gly-Pro-Pro-Gly-Pro-Pro-Gly-Pro-Pro-Gly-
Pro-Pro-Gly-Pro-Pro-Gly-Pro-Pro-Gly-Arg-Pro-Lys-
Pro-Gln-Gln-Phe-Phe-Gly-Leu-Met;

(SEQ ID NO: 390)
Hyp-Pro-Gly-Hyp-Pro-Gly-Hyp-Pro-Gly-Hyp-Pro-Gly-
Hyp-Pro-Gly-Hyp-Pro-Gly-Hyp-Pro-Gly-Arg-Pro-Lys-
Pro-Gln-Gln-Phe-Phe-Gly-Leu-Met;

(SEQ ID NO: 391)
Pro-Hyp-Gly-Pro-Hyp-Gly-Pro-Hyp-Gly-Pro-Hyp-Gly-
Pro-Hyp-Gly-Pro-Hyp-Gly-Pro-Hyp-Gly-Arg-Pro-Lys-
Pro-Gln-Gln-Phe-Phe-Gly-Leu-Met;

(SEQ ID NO: 392)
Flp-Hyp-Gly-Flp-Hyp-Gly-Flp-Hyp-Gly-Flp-Hyp-Gly-
Flp-Hyp-Gly-Flp-Hyp-Gly-Flp-Hyp-Gly-Arg-Pro-Lys-
Pro-Gln-Gln-Phe-Phe-Gly-Leu-Met;

(SEQ ID NO: 393)
Clp-Hyp-Gly-Clp-Hyp-Gly-Clp-Hyp-Gly-Clp-Hyp-Gly-
Clp-Hyp-Gly-Clp-Hyp-Gly-Clp-Hyp-Gly-Arg-Pro-Lys-
Pro-Gln-Gln-Phe-Phe-Gly-Leu-Met;

(SEQ ID NO: 394)
Pro-Flp-Gly-Pro-Flp-Gly-Pro-Flp-Gly-Pro-Flp-Gly-
Pro-Flp-Gly-Pro-Flp-Gly-Pro-Flp-Gly-Arg-Pro-Lys-
Pro-Gln-Gln-Phe-Phe-Gly-Leu-Met;
and
                                              (SEQ ID NO: 395)
Pro-Clp-Gly-Pro-Clp-Gly-Pro-Clp-Gly-Pro-Clp-Gly-
Pro-Clp-Gly-Pro-Clp-Gly-Pro-Clp-Gly-Arg-Pro-Lys-
Pro-Gln-Gln-Phe-Phe-Gly-Leu-Met.
```

In other methods of the invention, the one or more therapeutic or diagnostic compounds are suitably conjugated or attached to the CMPs via a covalent bond other than a peptide bond. For example, therapeutic compounds can be attached directly to a cysteine or methionine residue on a CMP described herein by covalently bonding a hydroxyl or amino group on an amino acid residue (e.g., a lysine residue) on the therapeutic or diagnostic compound (if it is a biologic molecule) to a sulfhydryl group on the cysteine or methionine residue of the CMP. Alternatively, if the CMP does not contain a cysteine or methionine residue, the one or more therapeutic or diagnostic compounds can be attached or conjugated to the CMP by a reaction between a hydroxyl group or amino group on the CMP and a sulfhydryl group on an amino acid residue (e.g., at a cysteine or methionine residue) on the therapeutic or diagnostic compound (if it is a biologic molecule). In yet another alternative method of conjugation, therapeutic compounds can be attached directly to a lysine residue on a CMP described herein by covalently bonding the therapeutic compound to an amino group on the lysine, for example using NHS ester conjugation (see, e.g., Mattson, G., et al., Molec. Biol. Rep. 17:167-183 (1993); Grabarek, Z. and Gergely, J., Anal. Biochem. 185:131-135 (1990); Staros, J. V. et al., Anal. Biochem. 156:220-2 (1986); Timkovich, R., Anal. Biochem. 79:135-43 (1977)). Such direct covalent attachments or conjugations between the CMP and the therapeutic/diagnostic compound can be accomplished using standard reaction techniques that will be familiar to those of ordinary skill in organic chemistry.

In other embodiments, particularly those wherein the therapeutic or diagnostic compound is not a biologic (and therefore does not have a peptide structure or amino acid residues having groups suitably attachable to cysteine, methionine, lysine or other residues on the CMP), such as small molecule organic or inorganic therapeutic or diagnostic compounds, the at least one therapeutic or diagnostic compound is indirectly attached to the collagen mimetic peptide via use of an attachment means. In such embodiments, the attachment means has two attachable ends, one of which attaches to an amino acid residue, and suitably a sulfhydryl group on a cysteine or methionine residue or an amino group on a lysine residue, of a CMP, and the other of which attaches to a hydroxyl or amino group on the therapeutic or diagnostic compound. For example, in certain such embodiments the attachment means comprises at least one polymeric chain having a first end and a second end, and the first end of the polymeric chain binds to the sulfhydryl group on a cysteine or methionine residue or an amino group on a lysine residue on the collagen mimetic peptide and the opposite or second end of the polymeric chain binds to an amino group or hydroxyl group on the therapeutic compound. In embodiments where the therapeutic or diagnostic compound is a biologic that is not suitable for direct attachment via peptide synthesis as described elsewhere herein, the second end of the attachment means can be attached to an amino group on an amino acid residue, such as a lysine residue, on the biologic therapeutic or diagnostic compound. Suitable such attachment means are well-known to those of ordinary skill in the art. For example, one attachment means suitable for use in accordance with this aspect of the invention includes a moiety which is a polymeric chain that on one end (the CMP-binding end in particular) comprises a sulfhydryl-binding group such as a maleimide, and on the other end (the therapeutic or diagnostic compounding-binding end in particular) comprises an amino-binding group such as N-hydroxysuccinimide. In certain such embodiments, the polymeric chain is a linear polyethyleneglycol chain comprising at least four ethyleneglycol monomers, e.g., from four to fifty ethyleneglycol monomers, from ten to forty ethyleneglycol monomers, from fifteen to thirty ethyleneglycol monomers, from fifteen to twenty-five ethyleneglycol monomers, from twenty to twenty-five ethyleneglycol monomers, and particularly four, six, eight, twelve, twenty, twenty-two, twenty-three, twenty-four or twenty-five ethyleneglycol monomers. Such attachment means suitable for attaching one or more therapeutic or diagnostic compounds to a CMP by the methods described herein are available commercially, e.g., from Thermo Fisher Scientific (Waltham, Mass.) (e.g., SM(PEG)6, SM(PEG)8, SM(PEG)12 and SM(PEG)24). By adjusting the length of the polymer chain, the bioavailability and sustainability of the therapeutic or diagnostic compound in vivo can be modulated—the use of longer polymer chains, e.g., a polymer comprising 24 ethyleneglycol monomers, will increase the rate of bioavailability of the compound once the CMP-TC has been introduced into the body of the human or veterinary animal, while the use of shorter polymer chains, e.g., a polymer comprising six ethyleneglycol monomers, will decrease the rate of bioavailability and thus increase the sustainability (or, in other words, will result in delayed release or sustained release) of the therapeutic or diagnostic compound. Hence, according to certain such aspects of the invention, the at least one therapeutic compound comprises at least one reactive hydroxyl group capable of being cross-linked to the collagen mimetic peptide using a polymeric linker.

Other indirect attachment methods for conjugating the one or more therapeutic or diagnostic compounds into or onto the CMPs also are suitably used according to the invention. For example, the at least one therapeutic or diagnostic compound can be enclosed within at least one nanoparticle that is attached via an attachment means, such as those described herein, to the collagen mimetic peptide. Alternatively, the collagen mimetic peptide can suitably comprise at least one biotin moiety and the therapeutic molecule can suitably comprise at least one avidin or streptavidin moiety, and the biotin moiety on the collagen mimetic peptide will bind to the avidin or streptavidin moiety on the therapeutic or diagnostic compound, thereby attaching the collagen mimetic peptide to the therapeutic or diagnostic compound. Of course, the alternative is also suitable for use, in which the collagen mimetic peptide can suitably comprise at least one avidin or streptavidin moiety and the therapeutic or diagnostic compound can suitably comprise at least one biotin moiety, and the biotin moiety on the at least one therapeutic or diagnostic compound will bind to the avidin or streptavidin moiety on the collagen mimetic peptide, thereby attaching the collagen mimetic peptide to the therapeutic compound.

Thus, according to certain embodiments of the invention, the therapeutic or diagnostic compounds can be suitably attached directly to the CMPs described herein. In other embodiments of the invention, the one or more therapeutic or diagnostic compounds can be attached indirectly to the CMPs described herein, for example via the use of a spacer, linker or bridge moiety. It is to be understood that whether the one or more therapeutic compounds are attached directly or indirectly to the CMPs, such attachment results in the production of conjugates of the CMPs and the one or more therapeutic compounds, which may be defined herein as CMP-TC conjugates.

Suitable therapeutic or diagnostic compounds for attachment or conjugation to the CMPs to produce the CMP-TCs of the present invention include any compound that has been shown to have particular therapeutic or preventative properties against one or more diseases, disorders, physical conditions or afflictions when introduced into a human or veterinary animal suffering from or predisposed to such diseases, disorders, physical conditions or afflictions. Provided that the therapeutic or diagnostic compound is capable of being conjugated or attached to at least one CMP according to the teachings herein, any therapeutic or diagnostic compound can be used in the conjugates, compositions and methods of the present invention. Suitable such therapeutic compounds may be biologic or non-biologic (e.g., so-called "small molecule") therapeutic compounds. Compounds suitable for use include, but are not limited to, a steroidal anti-inflammatory drug, (e.g., prednisolone or a pharmaceutically acceptable salt thereof, such as prednisolone acetate), a nonsteroidal anti-inflammatory drug (e.g., acetylsalicylic acid, acetaminophen, ibuprofen, naproxen, nepafenac, bromfenac, diclofenac, flurbiprofen, ketoprofen, and ketorolac, and pharmaceutically acceptable salts, esters and derivatives thereof), a topical anesthetic (e.g., tetracaine, lidocaine, oxybuprocaine, proparacaine, and the like), a vitamin or a vitamin derivative or vitamin precursor (e.g., retinol, tretinoin, retinal, carotene and other retinoids and retinoid derivatives or precursors; folate; α-tocopherol; calciferol; phylloquinone, menadione and other vitamin K forms, precursors or derivatives, ascorbate; and the like), a therapeutic enzyme or a therapeutic fragment thereof (e.g., a collagenase and a serine protease, or a therapeutically effective fragment thereof), an antibiotic (e.g., an aminoglycoside antibiotic (such as gentamycin, tobramycin, paromomycin, kanamycin, neomycin and amikacin, and a pharmaceutically acceptable salt or ester thereof, e.g., tobramycin sulfate), a fluoroquinolone antibiotic (such as moxifloxacin, gatifloxacin, levofloxacin, gemifloxacin, ciprofloxacin, norfloxacin and ofloxacin, and a pharmaceutically acceptable salt, ester or derivative thereof, e.g., moxifloxacin hydrochloride, ciprofloxacin hydrochloride and gatifloxacin hydrochloride), a sulfonamide antibiotic (such as sulfacetamide, sulfadiazine, sulfadimidine, sulfafurazole (sulfisoxazole), sulfisomidine (sulfaisodimidine), sulfadoxine, sulfamethoxazole, sulfamoxole, sulfanitran, sulfadimethoxine, sulfamethoxypyridazine, sulfametoxydiazine, sulfametopyrazine and terephtyl, and a pharmaceutically acceptable salt, ester or derivative thereof), a β-lactam antibiotic (such as a penicillin or a derivative thereof (for example penicillin G, penicillin V, a benzylpenicillin and phenoxymethylpenicillin), dicloxacillin, flucloxacillin, oxacillin, nafcillin, amoxicillin, an ampicillin, ticarcillin, piperacillin, ritipenem, a carbapenem (e.g., ertapenem, doripenem, imipenem and meropenem, and a pharmaceutically acceptable salt, ester or derivative thereof), a cephem (such as cefazolin, cefalexin, cefadroxil, cefapirin, cefaclor, cefotetan, cephamycin (cefoxitin), cefprozil, cefuroxime axetil, ceftriaxone, ceftazidime, cefoperazone, cefdinir, cefcapene, cefdaloxime, ceftizoxime, cefmenoxime, cefotaxime, cefpiramide, cefpodoxime, ceftibuten, cefditoren, cefepime, ceftaroline fosamil, ceftolozane, ceftobiprole, ceftiofur, cefquinome and cefovecin, and a pharmaceutically acceptable salt, ester or derivative thereof), a monobactam (such as aztreonam or a pharmaceutically acceptable salt, ester or derivative thereof) and a β-lactamase inhibitor (such as sulbactam, tazobactam, clavulanic acid and avibactam, and a pharmaceutically acceptable sat, ester or derivative thereof)) or a cyclic peptide antibiotic (such as cyclosporine), a therapeutic monoclonal antibody or a therapeutic fragment thereof (such as adalimumab, altumomab, atezolizumab, atlizumab, bevacizumab, canakinumab, catumaxomab, certolizumab, cetuximab, clivatuzumab, edrecolomab, efalizumab, fontolizumab, girentuximab, golimumab, infliximab, labetuzumab, MABp1 (Xilonix™), natalizumab, nimotuzumab, nivolumab, oregovomab, panitumumab, pembrolizumab, pemtumomab, pertuzumab, ramucirumab, ranibizumab, rituximab, ruplizumab, tracatuzumab, tocilizumab, trastuzumab, ustekinumab, vedolizumab, visilizumab, votumumab, zalutumumab and zanolimumab, and active fragments, combinations or conjugates thereof), a therapeutic fusion protein (in certain embodiments, a recombinant fusion protein such as aflibercept (Regeneron), etanercept (Amgen), alefacept (Astellas Pharma), abatacept (Bristol-Myers Squibb), rilonacept (Regeneron), romiplostim (Amgen) and belatacept (Bristol-Myers Squibb)), a prostaglandin analogue (such as latanoprost, travoprost, tafluprost, unoprostone, netarsudil, tatanoprostene bunod, netarsudil and bimatoprost, and pharmaceutically acceptable salts, esters and derivatives thereof), a growth factor (such as EGF, PDGF, TGF β, IGF-1, VEGF, FGF-β, IGF-1) or a therapeutic or growth-promoting (particularly skin growth-promoting) fragment thereof, a neuropeptide (such as Substance P (SEQ ID NO:388), an α-adrenergic antagonist (such as brimonidine, clonidine and apraclonidine, and pharmaceutically acceptable salts, esters or derivatives thereof), a 3-adrenergic antagonist (such as timolol, propranolol, atenolol, levobunolol, carteolol, betaxolol, and pharmaceutically acceptable salts, esters and derivatives thereof, e.g., timolol maleate), a cell surface receptor antagonist (such as lifitegrast or etanercept), a carbonic anhydrase inhibitor (such as dorzolamide, brinzolamide, methazolamide and acetazolamide, and pharmaceutically acceptable salts, esters and derivatives thereof, e.g., dorzolamide hydrochloride), and pharmaceutically acceptable salts, esters and derivatives thereof. With certain such therapeutic compounds, administration simultaneously with the CMPs described herein, whether as a CMP-TC conjugate or simply with one or more CMPs and one or more TCs in an admixture or applied separately, may prevent, attenuate or lessen one or more adverse side effects of the therapeutic compound. For example, it is known that the therapeutic administration of certain fluoroquinolone antibiotics may cause damage to collagen and collagen-containing structures (e.g., tendons) in humans or veterinary animals who have been treated with fluoroquinolones (see, e.g., "FDA Drug Safety Communication: FDA updates warnings for oral and injectable fluoroquinolone antibiotics due to disabling side effects," accessed Nov. 6, 2017, at fda.gov/Drugs/DrugSafety/ucm511530.htm). As a result, simultaneous or co-administration of one or more of the CMPs described herein with one or more fluoroquinolone antibiotics to a human or veterinary animal in need of treatment with fluoroquinolones may allow the patient to receive the therapeutic benefits of the fluoroquinolone while mitigating, ameliorating or avoiding the collagen disruption resulting from such therapy, as the CMP can localize to and repair areas of damaged collagen in vivo.

Other suitable therapeutic compounds for use in the CMP-TC compounds, compositions and conjugates of the present invention include other non-biologic small molecule therapeutic compounds, including but not limited to alkylating agents, anti-tumor antibiotics, antimetabolites, hormonal agents, plant alkaloids, angiogenesis inhibitor, GnRH agonists, tyrosine kinase inhibitors, and the like. Examples of such non-biologic small molecule therapeutic compounds suitably used in accordance with the invention include but are not limited to a nitrosourea, a lenalidomide, imatinib, penatrexed, bortexomib, abiraterone acetate, everolimus, taxol, docetaxel, paclitaxel, carbazitaxel, mitoxantrone, carboplatin, cisplatin, gemcitabine, doxorubicin, casodex, flutamide, enzalutamide, abiraterone, sipuleucel-T and ketoconazole. Other suitable non-biologic small molecule therapeutic compounds that are advantageously used in forming the CMP-TC conjugates of the present invention, particularly for producing CMP-TC conjugates that are useful in treating certain cancers and preventing tumor metastasis, include inhibitors of lysyl oxidase (LOX), lysyl oxidase-like 1 (LOXL1) and lysyl oxidase-like 2 (LOXL2) enzymes. Such inhibitors have been suggested to have potential therapeutic application in treating and/or preventing certain cancers and the metastasis of solid tumors (see, e.g., U.S. Pat. Nos. 5,201,456; 5,120,764; 5,252,608; 8,461, 303; 8,658,167; 8,680,246; 9,176,139; 9,255,086; and 9,289,447; see also Erler, J. T., et al., Nature 440:1222-1226 (2006); Erler, J. T., et al., Cancer Cell 15(1):35-44 (2009); Bondareva, A., et al., PLoS ONE 4(5):e5620 (2009); Granchi, C., et al., ChemMedChem 4(10:1590-1594 (2009); and Fang, M., et al., Tumor Biol. 35:2871-2882 (2014); the disclosures of all of which are incorporated herein by reference in their entireties). In related aspects of the invention, CMP-TC conjugates comprising one or more inhibitors of LOX or LOX-like enzymes are suitably used in treating and/or preventing certain fibrotic diseases and disorders that are mediated by oxidoreductase enzymes such as LOX and the LOX-like enzymes (e.g., LOXL1 and LOXL2) in humans and veterinary animals. Fibrotic diseases and disorders suitably treated and/or prevented according to this aspect of the invention include but are not limited to pulmonary fibrosis, liver cirrhosis, myocardial fibrosis, surgical scarring, systemic sclerosis, scleroderma, keloid formation, proliferative vitreo retinopathy, and other fibrotic diseases and disorders that will be familiar to those of ordinary skill in the relevant arts. Particularly useful inhibitors of LOX and the Lox-like proteins include β-aminopropionitrile and certain derivatives and prodrugs thereof (see, e.g., U.S. Pat. Nos. 5,201,456; 5,120,764; 5,252,608; 8,461,303; 8,680,246; 9,176,139; and 9,255,086; the disclosures of all of which are incorporated herein in their entireties), as well as antibodies (which may be polyclonal or, preferably monoclonal) and fragments or portions thereof which bind to and inhibit the activity or function of LOX and LOX-like enzymes (see, e.g., U.S. Pat. No. 8,461,303; the disclosure of which is incorporated herein in its entirety).

Suitable diagnostic compounds for attachment or conjugation to CMPs to produce the conjugates and compositions of the invention include, but are not limited to, labeled probes, such as fluorescent dyes (e.g., quantum dots, indocyanine green, fluorescein, rhodamine, a merocyanine dye, a near-infrared fluorescent dye, and the like); a radioisotope, a nuclide used for PET, a nuclide used for SPECT, particularly wherein each of the radioisotope, the nuclide used for PET or SPECT is selected from the group consisting of $^{11}C$, $^{13}N$, $^{15}O$, $^{18}F$, $^{66}Ga$, $^{67}Ga$, 68Ga, $^{60}Cu$, $^{61}Cu$, $^{62}Cu$, $^{67}Cu$, $^{64}Cu$, $^{48}V$, Tc-99m, $^{241}Am$, $^{55}Co$, $^{57}Co$, $^{153}Gd$, $^{111}In$, $^{133}Ba$, $^{82}Rb$, $^{139}Ce$, Te-123m, $^{137}Cs$, $^{86}Y$, $^{90}Y$, $^{185/187}Re$, $^{86/88}Re$, $^{125}I$, a complex thereof, and a combination thereof; and an MRI contrast medium, a CT contrast medium, and a magnetic material, particularly wherein each of the MRI contrast medium, the CT contrast medium, and the magnetic material is selected from the group consisting of gadolinium, Gd-DTPA, Gd-DTPA-BMA, Gd-HP-D03A, iodine, iron, iron oxide, chromium, manganese, a complex or chelate complex thereof, and a combination thereof. According to such aspects of the invention, the CMP and the labeled probe are suitably physically or chemically bound directly to each other, for example via a direct conjugation through a coordinate bond, a covalent bond, a hydrogen bond, a hydrophobic interaction or a physical adsorption, or indirectly via use of at least one attachment means such as those described herein and others that are known in the art. Methods of conjugating or attaching diagnostic compounds to proteins, such as CMPs, are known in the art (see, e.g., U.S. Publ. Patent Appl. No. US 2012/0195828 A1, the disclosure of which is incorporated herein in its entirety).

Use of CMPs and CMP-TC Conjugates

Thus, the invention provides methods of preparing compositions that are useful in treating, preventing, diagnosing or ameliorating a disease, disorder or medical condition in humans or veterinary animals. In yet another aspect, the invention provides methods of treating, preventing, diagnosing or ameliorating a disease, disorder or medical or physical condition in humans or veterinary animals using the compositions of the invention. Particularly preferred CMPs for use in such aspects of the invention include CMPs comprising, consisting essentially of, or consisting of, CMPs having an amino acid sequence of (Pro-Pro-Gly)$_7$ (SEQ ID NO:1), (Flp-Hyp-Gly)$_7$ (SEQ ID NO:6) or (Clp-Hyp-Gly)$_7$ (SEQ ID NO:9), and derivatives thereof comprising one or more cysteine, methionine or lysine residues such as those described elsewhere herein.

The CMPs and CMP-TC conjugates of the present invention, including solutions, gels, films, wafers, membranes, spheres, nanoparticles and suspensions comprising, consisting essentially of or consisting of the CMPs and/or CMP-TC conjugates of the present invention, are suitably used as or included in compositions for use in, or as, a medicament for treating, preventing or ameliorating a variety of diseases or disorders in humans or veterinary animals in need of treatment or prevention thereof. Other compositions provided by this aspect of the invention provide the use of CMPs conjugated to one or more diagnostic compounds or molecules, such as one or more labeled probes, which then are used as diagnostic reagents in a variety of tests and assays, particularly in vivo or in situ, to diagnose a disease, disorder, or physical condition in a human or veterinary animal. Such medicament compositions or diagnostic compositions may comprise, in addition to the CMPs, CMP-TC conjugates or CMPs conjugated to one or more diagnostic compounds or molecules, one or more additional therapeutic compounds or pharmaceutically active ingredients (e.g., one or more antibiotics, one or more growth factors, autologous plasma rich in growth factors (PRGF), one or more cytokines, one or more antibodies fragments thereof, one or more non-biologic small molecule therapeutic compounds, and pharmaceutically active salts, esters and derivatives thereof, and the like, including those described herein and others that are known in the art. The compositions of the invention may additionally or alternatively comprise one or more pharmaceutically acceptable carriers or excipients. Pharmaceutically acceptable carriers or excipients suitable for use in the compositions and methods of the invention include, for example, one or more solvents (which may include water, an organic solvent or an inorganic solvent), one or more buffers, one or more polymers, one or more salts, one or more sugars, one or more sugar alcohols, one or more disintegrating agents, one or more aerosolizing agents or carriers, one or more dessicants, and the like. Other pharmaceutically acceptable carriers or excipients suitable for use in the compositions of the present invention will be readily familiar to those of ordinary skill in the relevant arts.

Diseases, disorders, physical conditions and medical conditions suitably treated, prevented, ameliorated or diagnosed using the compositions and methods of the invention include, but are not limited to ocular diseases or disorders, skin diseases or disorders, cancers, gastrointestinal diseases or disorders, genitourinary tract diseases or disorders, fibrotic diseases or disorders, cardiovascular diseases or disorders, bone diseases or disorders and rheumatic diseases or disorders.

Ocular diseases or disorders that can be treated, prevented, ameliorated or diagnosed using the compositions and methods of the invention include but are not limited to glaucoma, cataracts, vitreous adhesions or floaters, macular degeneration, dry eye syndrome, corneal keratitis, non-infectious corneal ulceration, non-infectious corneal melting, infectious corneal ulceration, infectious corneal melting, conjunctivitis, Stevens-Johnson Syndrome, scleritis, episcleritis, ectasia, keratoconus, corneal lacerations, corneal erosion, corneal abrasions, and post-operative afflictions of the eye resulting from eye surgery. Such post-operative afflictions of the eye resulting from eye surgery can be, for example, afflictions arising post-operatively from cataract surgery or glaucoma surgery, particularly wherein those afflictions result in or are a post-operative state of the eye requiring medication.

According to this aspect of the invention, methods of treating or preventing an ocular disease, disorder or wound in a human or veterinary animal suffering from or predisposed to an ocular disease, disorder or wound, comprise administering the compositions described herein, particularly the CMPs or CMP-TC conjugates and/or compositions comprising such conjugates, to an eye of a human or veterinary animal. Without wishing to be bound by theory, the inventors surmise that in areas of eye disease or disorder there is sufficient disruption of type I collagen such that the CMP will target the site of the eye disease or disorder specifically and intercalate into the collagen structure, thereby delivering the therapeutic compound to the site where it must act to treat, prevent or ameliorate the eye disease or disorder. The conjugates or compositions are suitably applied to the eye in a dosage sufficient to treat or prevent the ocular disease, disorder or wound, and the condition of the eye in said human or veterinary animal is then monitored over time for improvement in the disease state or physical condition. If necessary, the conjugate or composition of the invention is then periodically readministered to the eye, according to dosing and treatment schedules and protocols described herein and others that will be familiar to the ordinarily skilled artisan, until the ocular disease, disorder or wound is cured, prevented or ameliorated. In such embodiments, the conjugates or compositions of the invention can be suitably administered to the eye conjunctivally or subconjunctivally, particularly by administering the conjugate or composition into the subconjunctival fornix. Administration of the conjugates or compositions to the eye can be accomplished by any well-known means, including applying the conjugates or compositions to the eye in the form of one or more drops or aliquots of a solution, a gel or a suspension that contains the composition or conjugates; via injection; in the form of a solid material such as a wafer or film (such as those described herein) that is implanted into an eye structure; in the form of a mesh or patch; by attaching the conjugate or composition to, or enclosing it within, one or more gels, spheres or nanoparticles that are then delivered into an eye structure. Other suitable methods of applying the conjugates or compositions to the eye to accomplish the therapeutic and diagnostic methods of the invention will be readily apparent to the ordinarily skilled artisan.

Skin diseases or disorders that can be treated, prevented, ameliorated or diagnosed using the compositions and methods of the invention include but are not limited to skin wounds, scarring, wrinkles, "crepey skin", skin cancer (e.g., melanomas, skin carcinomas, skin sarcomas, histiocytomas) and skin burns, including sunburn. Other skin diseases or disorders suitably treated, prevented, ameliorated or diagnosed according to the invention include psoriasis and eczema, shingles, irritant contact dermatitis and allergic contact dermatitis (such as poison ivy, poison oak or poison sumac).

According to this aspect of the invention, methods of treating or preventing a skin disease, disorder or wound in a human or veterinary animal suffering from or predisposed to a skin disease, disorder or wound, comprise administering the compositions described herein, particularly the CMPs and CMP-TC conjugates, and compositions comprising such CMPs and CMP-TC conjugates, to the skin of a human or veterinary animal at a site proximal to the location of a lesion associated with or causing the skin disease, wound or disorder. Without wishing to be bound by theory, the inventors surmise that in areas of skin disease or disorder there is sufficient disruption of type I collagen such that the CMP will target the site of the skin disease or disorder specifically and intercalate into the collagen structure, thereby delivering the CMP and/or therapeutic compound to the site where it must act to treat, prevent or ameliorate the skin disease or disorder. Alternatively, the disease or disorder afflicting the skin can be excised or resected from the skin (e.g., via surgical removal, for example of a skin cancer), and the skin wound resulting from such excision or resection can be treated with one or more compositions of the invention according to the methods described herein. In certain embodiments, one or more of the CMPs themselves, or one or more CMP-TC conjugates, or any combination thereof, can be introduced into the skin, particularly intraepidermally, intradermally or subcutaneously, in the form of a so-called "cosmeceutical" (see, e.g., Epstein, H., Clin. Dermatol. 27(5):453-460 (2009)). Particularly preferred CMP-TC conjugates or compositions for use in such aspects of the invention include those wherein the therapeutic compound is Substance P (SEQ ID NO:388), particularly those wherein the CMP-TC conjugate has an amino acid sequence corresponding to any one of SEQ ID NOs: 389-395. Additional particularly preferred CMP-TC conjugates or compositions for use in such aspects of the invention include those wherein the therapeutic compound is retinol or a derivative or precursor thereof. Additional preferred compositions comprise such compositions that comprise or further comprise at least one growth factor, at least one antibiotic, at least one antifungal compound or at least one antiviral compound. Suitable growth factors, antibiotics, antifungal compounds and antiviral compounds include those described herein and others that are well-known in the dermatological and other relevant arts. According to this aspect of the invention, the conjugates or compositions are suitably applied to or into the skin in a dosage sufficient to treat or prevent the skin disease, disorder or wound, and the condition of the skin in said human or veterinary animal is then monitored over time for improvement in the disease state or physical condition. If necessary, the conjugate or composition of the invention is then periodically readministered to or into the skin, according to dosing and treatment schedules and protocols described herein and others that will be familiar to the ordinarily skilled artisan, until the skin disease, disorder or wound is cured, prevented or ameliorated. In such embodiments, the conjugates or compositions of the invention are suitably administered to or into the skin topically, intraepidermally, intradermally or subdermally. Administration of the conjugates or compositions to or into the skin can be accomplished by any well-known means, including in the form of a solution, an ointment, a salve, a patch, a cream, a topical solution and a drug eluting wafer. For example, the conjugates or compositions can be applied to or introduced into the skin in the form of one or more drops of solution or a suspension that contains the composition or conjugates; via injection; in the form of a coating on a solid material that is implanted into the skin; in the form of a mesh or patch; by attaching the conjugate or composition to, or enclosing it within, one or more nanoparticles that are then delivered into the skin. Other suitable methods of applying the conjugates or compositions to or into the skin to accomplish the therapeutic and diagnostic methods of the invention will be readily apparent to the ordinarily skilled artisan.

Cancers that can be treated, prevented, ameliorated or diagnosed using the compositions and methods of the invention include but are not limited to skin cancers (e.g., those described elsewhere herein), intraluminal cancers and brain cancers. Intraluminal cancers suitably treated, prevented, diagnosed or ameliorated using the conjugates, compositions and methods of the invention include but are not limited to colorectal cancer, intestinal cancer, duodenal cancer, stomach cancer, pancreatic cancer, esophageal cancer, a bladder cancer (e.g., non-muscle-invasive bladder cancer or carcinoma in situ of the bladder), a cancer of the upper urinary tract, alternatively referred to and also known to those of ordinary skill as the renal pelvis (e.g., upper tract urothelial carcinoma, Wilms tumor and renal cancer), vaginal cancer, cervical cancer, uterine cancer, ovarian cancer, luminal breast cancer and lung cancer. Brain cancers suitably treated, prevented, diagnosed or ameliorated using the conjugates, compositions and methods of the invention include but are not limited to gliomas, glioblastomas, meningiomas, pituitary tumors, craniopharyngioma and hemangioblastomas. Other non-luminal cancers are also suitably treated, prevented, diagnosed or ameliorated using the conjugates, compositions and methods of the invention, including but not limited to prostate cancer, testicular cancer, non-luminal breast cancer, bone cancer, head and neck cancer, thyroid cancer, liver cancer, sarcomas (e.g., Kaposi sarcoma, Ewing sarcoma, osteosarcoma, soft tissue sarcoma and rhabdomyosarcoma), and the like.

According to this aspect of the invention, methods of treating or preventing a cancer in a human or veterinary animal suffering from or predisposed to a cancer, comprise administering the compositions described herein, particularly the CMPs and CMPs and/or conjugates, into the organ lumen, or into the cranium or into or on the brain, of a human or veterinary animal, at a site proximal to the location of the cancer or tumor. Without wishing to be bound by theory, the inventors surmise that in areas of cancer there is sufficient disruption of type I collagen, or upregulation of type I collagen in the case of brain cancer, such that the CMP will target the site of the cancer specifically and intercalate into the collagen structure, thereby delivering the CMP and/or therapeutic compound to the site where it must act to treat, prevent or ameliorate the cancer. Particularly preferred conjugates or compositions for use in this aspect of the invention include those wherein the therapeutic compound is a biologic therapeutic compound, particularly one or more monoclonal antibodies or fragments thereof or one or more therapeutic fusion proteins, particularly recombinant fusion proteins, including those described herein. Additional preferred compositions comprise such compositions that further comprise at least one growth factor, at least one antibiotic, at least one antifungal compound or at least one antiviral compound. Suitable growth factors, antibiotics, antifungal compounds and antiviral compounds include those described herein and others that are well-known in the dermatological and other relevant arts. According to this aspect of the invention, the conjugates or compositions are suitably applied to or into the organ lumen, or the cranium or brain, in a dosage sufficient to treat, prevent or ameliorate the cancer, and the progression, remission or stasis of the cancer in the human or veterinary animal is then monitored over time for improvement in the cancer disease state (e.g., shrinkage of the tumor or at least non-progression or remission of the cancer). If necessary, the conjugate or composition of the invention is then periodically readministered into the organ lumen, or into the cranium or into or on the brain, according to dosing and treatment schedules and protocols described herein and others that will be familiar to the ordinarily skilled artisan, until the cancer is cured, prevented or ameliorated, or goes into permanent remission. In such embodiments, the conjugates or compositions of the invention are suitably administered to or into the organ lumen or the brain parenterally or via direct application to the tumor site or, in the case of excision or resection of the tumor, via direct application to the tumor bed or the wound remaining following excision or resection of the tumor. Parenteral administration of the conjugates or compositions of the invention can be accomplished via a route selected from the group consisting of subcutaneous injection, intravenous infusion, intraarterial infusion, transdermal diffusion, implantation of a drug eluting wafer or film, sublingually, orally, via aerosol inhalation, intravaginally, rectally, or intracranially. In certain such embodiments the conjugate or composition can be administered parenterally to the human or veterinary animal in the form of a mesh, film, wafer, sphere, nanoparticle, gel or patch that is implanted into the human or veterinary animal at or proximal to the site of the cancer. In other such embodiments, particularly those in which the cancer is an intraluminal cancer, the conjugates or compositions of the invention can be administered to the lumen of the cancerous organ in the human or veterinary animal using a medical instrument suitable for such purpose, such as an endoscope, a bronchoscope (for example, via bronchial lavage for treating, preventing or diagnosing a cancer of the pulmonary tract such as bronchial cancer or lung cancer), a proctoscope, a colonoscope, a cystoscope (e.g., into the bladder or upper urinary tract via cystoscopic irrigation), a gastroscope and a laparoscope, or other suitable surgical/medical instruments capable of delivering a dose of a medicament such as the conjugates and compositions of the invention to the human or veterinary animal at the site of the cancer. In certain such embodiments, the conjugate or composition can be administered following surgical excision or resection of a solid tumor, or removal or aspiration of a tumor ascites using, e.g., a trochar introduced into the abdomen for removal of abdominal ascites fluid. In such embodiments, the conjugate or composition of the invention (along with, optionally, one or more additional therapeutic agents) can be introduced directly into the surgical excision or into the ascites area, for example through any of the instruments or devices described above.

In other embodiments, administration of the conjugates or compositions to or into the organ lumen or the brain can be accomplished by any well-known means, including in the form of a solution, an ointment, a salve, a patch, a cream, a topical solution and a drug eluting wafer. For example, the conjugates or compositions can be applied to or introduced into the lumen of the organ or into or on the brain in the form of one or more drops of solution or a suspension that contains the composition or conjugates; via injection; in the form of a coating on a solid material that is implanted into the organ lumen or the brain; in the form of a mesh or patch; by attaching the conjugate or composition to, or enclosing it within, one or more nanoparticles that are then delivered into the organ lumen or the brain. Other suitable methods of applying the conjugates or compositions to or into the organ lumen or the brain to accomplish the therapeutic and diagnostic methods of the invention will be readily apparent to the ordinarily skilled artisan.

Gastrointestinal diseases or disorders that can be treated, prevented, ameliorated or diagnosed using the compositions and methods of the invention include but are not limited to irritable bowel syndrome, Crohn's Disease, an ulcer, ulcerative colitis, esophagitis, Barrett's esophagitis, gastritis and proctitis.

According to this aspect of the invention, methods of treating or preventing a gastrointestinal disease or disorder in a human or veterinary animal suffering from or predisposed to a gastrointestinal disease or disorder comprise administering the compositions described herein, particularly the CMPs and CMP-TC conjugates and compositions comprising such CMPs and/or conjugates, into the gastrointestinal tract of a human or veterinary animal, at a site proximal to the location of a lesion associated with or causing the gastrointestinal disease or disorder. Without wishing to be bound by theory, the inventors surmise that in areas of certain gastrointestinal diseases and disorders there is sufficient disruption of type I collagen such that the CMP will target the site of the gastrointestinal disease or disorder specifically and intercalate into the collagen structure, thereby delivering the CMP and/or therapeutic compound to the site where it must act to treat, prevent or ameliorate the gastrointestinal disease or disorder. Particularly preferred conjugates or compositions for use in this aspect of the invention include those wherein the therapeutic compound is a biologic therapeutic compound, particularly one or more monoclonal antibodies or fragments thereof or one or more therapeutic fusion proteins, particularly recombinant fusion proteins, including those described herein. According to this aspect of the invention, the conjugates or compositions are suitably applied to or into the gastrointestinal tract in a dosage sufficient to treat, prevent or ameliorate the gastrointestinal disease or disorder, and the progression, remission or stasis of the gastrointestinal disease or disorder in the human or veterinary animal is then monitored over time for improvement in the disease or disorder state. If necessary, the conjugate or composition of the invention is then periodically readministered into the gastrointestinal tract according to dosing and treatment schedules and protocols described herein and others that will be familiar to the ordinarily skilled artisan, until the gastrointestinal disease or disorder is cured, prevented or ameliorated. In such embodiments, the conjugates or compositions of the invention are suitably administered to or into the gastrointestinal tract parenterally or topically. Parenteral administration is accomplished by any art-known route of administration of a therapy to the gastrointestinal tract, for example via a route selected from the group consisting of subcutaneous injection, intravenous infusion, intraarterial infusion, transdermal diffusion, implantation of a drug eluting wafer, sublingually, orally or rectally. In such methods, the composition is suitably administered parenterally to the human or veterinary animal in the form of a pill, capsule, solution, suspension or powder that is ingested by the human or veterinary animal, or in the form of a mesh or patch that is implanted within the gastrointestinal tract at or proximal to the site of the disease or disorder. In other such embodiments, particularly those in which the disease or disorder is intraluminal in the gastrointestinal tract, the conjugates or compositions of the invention can be administered to the lumen of the gastrointestinal organ in the human or veterinary animal using a medical instrument suitable for such purpose, such as a proctoscope, a colonoscope, a cystoscope (e.g., into the bladder or upper urinary tract cystoscopically), a gastroscope and a laparoscope, or other suitable surgical/medical instruments capable of delivering a dose of a medicament such as the conjugates and compositions of the invention to the human or veterinary animal at the site of the gastrointestinal disease or disorder.

In other embodiments, administration of the conjugates or compositions to or into the gastrointestinal tract can be accomplished by any well-known means, including in the form of a solution, an ointment, a salve, a patch, a cream, a topical solution and a drug eluting wafer. For example, the conjugates or compositions can be applied to or introduced into the gastrointestinal tract in the form of one or more drops of solution or a suspension that contains the composition or conjugates; via injection; in the form of a coating on a solid material that is implanted into the gastrointestinal tract; in the form of a mesh or patch; by attaching the conjugate or composition to, or enclosing it within, one or more nanoparticles that are then delivered into the gastrointestinal tract. Other suitable methods of applying the conjugates or compositions to or into the gastrointestinal tract to accomplish the therapeutic and diagnostic methods of the invention will be readily apparent to the ordinarily skilled artisan.

Genitourinary diseases or disorders that can be treated, prevented, ameliorated or diagnosed using the compositions and methods of the invention include but are not limited to female urinary incontinence, cystitis, interstitial cystitis, irritable bladder syndrome, ureteritis and vaginitis.

According to this aspect of the invention, methods of treating or preventing a genitourinary disease or disorder in a human or veterinary animal suffering from or predisposed to a genitourinary disease or disorder comprise administering the compositions described herein, particularly the CMPs and CMP-TC conjugates and compositions comprising such CMPs and/or conjugates, into the genitourinary tract of a human or veterinary animal, at a site proximal to the location of a lesion associated with or causing the genitourinary tract disease or disorder. Without wishing to be bound by theory, the inventors surmise that in areas of certain genitourinary diseases and disorders there is sufficient disruption of type I collagen such that the CMP will target the site of the genitourinary disease or disorder specifically and intercalate into the collagen structure, thereby delivering the CMP and/or therapeutic compound to the site where it must act to treat, prevent or ameliorate the genitourinary disease or disorder. According to this aspect of the invention, the conjugates or compositions are suitably applied to or into the genitourinary tract in a dosage sufficient to treat, prevent or ameliorate the genitourinary disease or disorder, and the progression, remission or stasis of the genitourinary disease or disorder in the human or veterinary animal is then monitored over time for improvement in the disease or disorder state. If necessary, the conjugate or composition of the invention is then periodically readministered into the genitourinary tract according to dosing and treatment schedules and protocols described herein and others that will be familiar to the ordinarily skilled artisan, until the genitourinary disease or disorder is cured, prevented or ameliorated. In such embodiments, the conjugates or compositions of the invention are suitably administered to or into the genitourinary tract parenterally or topically. Parenteral administration is accomplished by any art-known route of administration of a therapy to the gastrointestinal tract, for example via a route selected from the group consisting of subcutaneous injection, intravenous infusion, intraarterial infusion, transdermal diffusion, implantation of a drug eluting wafer, sublingually, orally, vaginally or rectally. In such methods, the composition is suitably administered parenterally to the human or veterinary animal in the form of a pill, capsule, solution, suspension or powder that is ingested by the human or veterinary animal, or in the form of a mesh or patch that is implanted within the genitourinary tract at or proximal to the site of the disease or disorder. In other such embodiments, particularly those in which the disease or disorder is intraluminal in the gastrointestinal tract, the conjugates or compositions of the invention can be administered to the lumen of the genitourinary organ in the human or veterinary animal using a medical instrument suitable for such purpose, such as an endoscope, a vaginoscope, and a laparoscope, or other suitable surgical/medical instruments capable of delivering a dose of a medicament such as the conjugates and compositions of the invention to the human or veterinary animal at the site of the genitourinary disease or disorder.

In other embodiments, administration of the conjugates or compositions to or into the genitourinary tract can be accomplished by any well-known means, including in the form of a solution, an ointment, a salve, a patch, a wafer, a film, a gel, spheres, nanoparticles, a cream, a topical solution and a drug eluting wafer. For example, the conjugates or compositions can be applied to or introduced into the genitourinary tract in the form of one or more drops of solution or a suspension that contains the composition or conjugates; via injection; in the form of a coating on a solid material that is implanted into the genitourinary tract; in the form of a mesh or patch; by attaching the conjugate or composition to, or enclosing it within, one or more nanoparticles that are then delivered into the genitourinary tract. Other suitable methods of applying the conjugates or compositions to or into the genitourinary tract to accomplish the therapeutic and diagnostic methods of the invention will be readily apparent to the ordinarily skilled artisan.

Fibrotic diseases or disorders that can be treated, prevented, ameliorated or diagnosed using the compositions and methods of the invention include but are not limited to pulmonary fibrosis, liver cirrhosis, myocardial fibrosis, surgical scarring, systemic sclerosis, scleroderma, keloid formation, proliferative vitreo retinopathy, and the like.

According to this aspect of the invention, methods of treating or preventing a fibrotic disease or disorder in a human or veterinary animal suffering from or predisposed to a bone disease or disorder comprise administering the compositions described herein, particularly the CMPs and CMP-TC conjugates and compositions comprising such CMPs and/or conjugates, into or near one or more tissues, organs or organ systems of a human or veterinary animal, at a site proximal to the location of a fibrotic lesion associated with or causing the fibrotic disease or disorder. Without wishing to be bound by theory, the inventors surmise that in areas of certain fibrotic diseases and disorders there is sufficient disruption of type I collagen such that the CMP will target the site of the fibrotic disease or disorder specifically and intercalate into the collagen structure, thereby delivering the therapeutic compound to the site where it must act to treat, prevent or ameliorate the fibrotic disease or disorder. According to this aspect of the invention, the conjugates or compositions are suitably applied to, near or into the tissue, organ or organ system in a dosage sufficient to treat, prevent or ameliorate the fibrotic disease or disorder, and the progression, remission or stasis of the fibrotic disease or disorder in the human or veterinary animal is then monitored over time for improvement in the disease or disorder state. If necessary, the conjugate or composition of the invention is then periodically readministered into, near or onto one or more tissues, organs or organ systems according to dosing and treatment schedules and protocols described herein and that will be familiar to the ordinarily skilled artisan, until the fibrotic disease or disorder is cured, prevented or ameliorated. In such embodiments, the conjugates or compositions of the invention are suitably administered to, near, on or into the tissues, organs or organ systems parenterally or topically. Parenteral administration is accomplished by any art-known route of administration of a therapy to the tissues, organ or organ systems, for example via a route selected from the group consisting of subcutaneous injection, intravenous infusion, intraarterial infusion, endoscopic application, transdermal diffusion, implantation of a drug eluting wafer, film, gel or putty, sublingually, orally or rectally. In such methods, the composition is suitably administered parenterally to the human or veterinary animal in the form of a pill, capsule, solution, suspension or powder that is ingested by the human or veterinary animal, or in the form of a mesh, film, wafer, gel, sphere, nanoparticle, putty or patch that is implanted near, on or into the fibrotic tissue, organ or organ system at or proximal to the site of the disease or disorder.

In other embodiments, administration of the conjugates or compositions to, near or into the tissues, organs or organ systems can be accomplished by any well-known means, including in the form of a solution, an ointment, a salve, a patch, a film, a gel, spheres, nanoparticles, putty, a cream, a topical solution and a drug eluting wafer. For example, the conjugates or compositions can be applied to or near, or introduced into, the tissues, organs or organ systems in the form of one or more drops of solution or a suspension that contains the composition or conjugates; via injection; in the form of a coating on a solid material that is implanted into, near or onto the tissues, organs or organ systems; in the form of a mesh or patch; by attaching the conjugate or composition to, or enclosing it within, one or more nanoparticles that are then delivered into, near or on the tissues, organs or organ systems. Other suitable methods of applying the conjugates or compositions to, on, near or into the tissues, organs or organ systems to accomplish the therapeutic and diagnostic methods of the invention will be readily apparent to the ordinarily skilled artisan.

Cardiovascular diseases or disorders that can be treated, prevented, ameliorated or diagnosed using the compositions and methods of the invention include but are not limited to myocardial infarction, cardiac insufficiency, cardiac valve disorders, atherosclerosis, cardiomyopathy, arrhythmias, congenital heart disease, coronary artery disease, pericardial disease, vascular occlusive disease (e.g., affecting the carotid artery, the aorta, the renal artery, the femoral artery, the pulmonary artery, and other large vessels and small vessels which may be arteries, arterioles, veins, venules and the like), Marfan syndrome, and the like.

According to this aspect of the invention, methods of treating or preventing a cardiovascular disease or disorder in a human or veterinary animal suffering from or predisposed to a cardiovascular disease or disorder comprise administering the compositions described herein, particularly the CMPs and/or CMP-TC conjugates and compositions comprising such CMPs and/or conjugates, into the vascular system of a human or veterinary animal suffering from or predisposed to such a disease or disorder. Without wishing to be bound by theory, the inventors surmise that in areas of certain cardiovascular diseases and disorders there is sufficient disruption of type I collagen such that the CMP introduced into the vascular system of the subject will target the site of the cardiovascular disease or disorder specifically and intercalate into the collagen structure, thereby delivering the CMP and/or therapeutic compound to the site where it must act to treat, prevent or ameliorate the cardiovascular disease or disorder. According to this aspect of the invention, the conjugates or compositions are suitably applied to or into the vascular system in a dosage sufficient to treat, prevent or ameliorate the cardiovascular disease or disorder, and the progression, remission or stasis of the cardiovascular disease or disorder in the human or veterinary animal is then monitored over time for improvement in the disease or disorder state. If necessary, the conjugate or composition of the invention is then periodically readministered into the vascular system according to dosing and treatment schedules and protocols described herein and others that will be familiar to the ordinarily skilled artisan, until the cardiovascular disease or disorder is cured, prevented or ameliorated. In such embodiments, the conjugates or compositions of the invention are suitably administered to or into the heart, pericardium, vessel or other relevant component of the vascular system parenterally or topically. Parenteral administration is accomplished by any art-known route of administration of a therapy to the vascular system, for example via a route selected from the group consisting of subcutaneous injection, intravenous infusion, intraarterial infusion, transdermal diffusion, via catheterization, embolization, implantation of a drug eluting wafer or film, sublingually, orally, rectally. In such methods, the composition is suitably administered parenterally to the human or veterinary animal in the form of a pill, capsule, solution, suspension or powder that is ingested by the human or veterinary animal, or in the form of a mesh, wafer, film, gel, putty, sphere, nanoparticle or patch that is implanted within the heart, pericardium, vessel or other relevant component of the vascular system at or proximal to the site involved in the cardiovascular disease or disorder.

In other embodiments, administration of the conjugates or compositions to or into the vascular system can be accomplished by any well-known means, including in the form of a solution, an ointment, a salve, a patch, a film, a gel, spheres, nanoparticles, a cream, a topical solution and a drug eluting wafer. For example, the conjugates or compositions can be applied to or introduced into the heart, pericardium, vessel or other relevant component of the vascular system in the form of one or more drops of solution or a suspension that contains the composition or conjugates; via injection; in the form of a coating on a solid material that is implanted into the heart, pericardium, vessel or other relevant component of the vascular system; in the form of a mesh or patch; by attaching the conjugate or composition to, or enclosing it within, one or more nanoparticles that are then delivered into the heart, pericardium, vessel or other relevant component of the vascular system. Other suitable methods of applying the conjugates or compositions to or into the vascular system to accomplish the therapeutic and diagnostic methods of the invention will be readily apparent to the ordinarily skilled artisan.

Bone diseases or disorders that can be treated, prevented, ameliorated or diagnosed using the compositions and methods of the invention include but are not limited to osteoporosis, bone fracture, osteomyelitis, osteogenesis imperfecta, Paget disease of bone, osteonecrosis, rickets, osteomalacia, acromegaly and the like.

According to this aspect of the invention, methods of treating or preventing a bone disease or disorder in a human or veterinary animal suffering from or predisposed to a bone disease or disorder comprise administering the compositions described herein, particularly the CMPs and CMP-TC conjugates and compositions comprising such CMPs and/or conjugates, into or near one or more bones of a human or veterinary animal, at a site proximal to the location of a lesion associated with or causing the bone disease or disorder. Without wishing to be bound by theory, the inventors surmise that in areas of certain bone diseases and disorders there is sufficient disruption of type I collagen such that the CMP will target the site of the bone disease or disorder specifically and intercalate into the collagen structure, thereby delivering the therapeutic compound to the site where it must act to treat, prevent or ameliorate the bone disease or disorder. According to this aspect of the invention, the conjugates or compositions are suitably applied to, near or into the bone in a dosage sufficient to treat, prevent or ameliorate the bone disease or disorder, and the progression, remission or stasis of the bone disease or disorder in the human or veterinary animal is then monitored over time for improvement in the disease or disorder state. If necessary, the conjugate or composition of the invention is then periodically readministered into, near or onto one or more bones according to dosing and treatment schedules and protocols described herein and others that will be familiar to the ordinarily skilled artisan, until the bone disease or disorder is cured, prevented or ameliorated. In such embodiments, the conjugates or compositions of the invention are suitably administered to, near, on or into the bones parenterally or topically. Parenteral administration is accomplished by any art-known route of administration of a therapy to the bones, for example via a route selected from the group consisting of subcutaneous injection, intravenous infusion, intraarterial infusion, endoscopic application, transdermal diffusion, implantation of a drug eluting wafer, film, gel or putty, sublingually, orally or rectally. In such methods, the composition is suitably administered parenterally to the human or veterinary animal in the form of a pill, capsule, solution, suspension or powder that is ingested by the human or veterinary animal, or in the form of a mesh, film, wafer, gel, sphere, nanoparticle, putty or patch that is implanted near, on or into the bone at or proximal to the site of the disease or disorder.

In other embodiments, administration of the conjugates or compositions to, near or into the bones can be accomplished by any well-known means, including in the form of a solution, an ointment, a salve, a patch, a film, a gel, spheres, nanoparticles, putty, a cream, a topical solution and a drug eluting wafer. For example, the conjugates or compositions can be applied to or near, or introduced into, the bones in the form of one or more drops of solution or a suspension that contains the composition or conjugates; via injection; in the form of a coating on a solid material that is implanted into, near or onto the bones; in the form of a mesh or patch; by attaching the conjugate or composition to, or enclosing it within, one or more nanoparticles that are then delivered into, near or on the bones. Other suitable methods of applying the conjugates or compositions to, on, near or into the bones to accomplish the therapeutic and diagnostic methods of the invention will be readily apparent to the ordinarily skilled artisan.

Rheumatic diseases or disorders that can be treated, prevented, ameliorated or diagnosed using the compositions and methods of the invention include but are not limited to arthritis (particularly rheumatoid arthritis, osteoarthritis and psoriatic arthritis), bursitis, crepitus, spondylosis, scleroderma, polymyalgia rheumatica and anarthritic syndrome.

According to this aspect of the invention, methods of treating or preventing a rheumatic disease or disorder in a human or veterinary animal suffering from or predisposed to a rheumatic disease or disorder comprise administering the compositions described herein, particularly the CMPs or CMP-TC conjugates and compositions comprising such CMPs and/or conjugates, to the human or veterinary animal at a site proximal to the location of a lesion associated with or causing the rheumatic disease or disorder. Without wishing to be bound by theory, the inventors surmise that in areas of certain rheumatic diseases and disorders there is sufficient disruption of type I collagen such that the CMP will target the site of the rheumatic disease or disorder specifically and intercalate into the collagen structure, thereby delivering the therapeutic compound to the site where it must act to treat, prevent or ameliorate the rheumatic disease or disorder. According to this aspect of the invention, the conjugates or compositions are suitably applied to or into the human or veterinary animal in a dosage sufficient to treat, prevent or ameliorate the rheumatic disease or disorder, and the progression, remission or stasis of the rheumatic disease or disorder in the human or veterinary animal is then monitored over time for improvement in the disease or disorder state. If necessary, the conjugate or composition of the invention is then periodically readministered to the human or veterinary animal according to dosing and treatment schedules and protocols described herein and others that will be familiar to the ordinarily skilled artisan, until the rheumatic disease or disorder is cured, prevented or ameliorated. In such embodiments, the conjugates or compositions of the invention are suitably administered to or into the human or veterinary animal parenterally or topically. Parenteral administration is accomplished by any art-known route of administration of a therapy designed to treat, prevent or ameliorate a rheumatic disease or disorder, for example via a route selected from the group consisting of subcutaneous injection, intravenous infusion, intraarterial infusion, transdermal diffusion, implantation of a drug eluting wafer, sublingually, orally, vaginally or rectally. In such methods, the composition is suitably administered parenterally to the human or veterinary animal in the form of a pill, capsule, solution, suspension or powder that is ingested by the human or veterinary animal, or in the form of a mesh or patch that is implanted within the human or veterinary animal at or proximal to the site of the disease or disorder. In other such embodiments, particularly those in which the rheumatic disease or disorder is located in or near a bone, tendon, cartilage, ligament, bursa, joint or associated structure, the compositions or conjugates of the invention are suitably administered to the human or veterinary animal using a medical instrument suitable for such purpose, such as an laparoscope, or other suitable surgical/medical instruments capable of delivering a dose of a medicament such as the conjugates and compositions of the invention to the human or veterinary animal at the site of the genitourinary disease or disorder.

In other embodiments, administration of the conjugates or compositions to or into the human or veterinary animal can be accomplished by any well-known means, including in the form of a solution, an ointment, a salve, a patch, a cream, a topical solution and a drug eluting wafer. For example, the conjugates or compositions can be applied to or introduced into the human or veterinary animal in the form of one or more drops of solution or a suspension that contains the composition or conjugates; via injection; in the form of a coating on a solid material that is implanted into the human or veterinary animal; in the form of a mesh or patch; by attaching the conjugate or composition to, or enclosing it within, one or more nanoparticles that are then delivered into the human or veterinary animal. Other suitable methods of applying the conjugates or compositions to or into the human or veterinary animal to accomplish the therapeutic and diagnostic methods of the invention will be readily apparent to the ordinarily skilled artisan.

In related embodiments, the invention provides devices, particularly medical devices, suitable for treating or preventing a disease, disorder or medical condition in a human or veterinary animal suffering from or predisposed to said disease, disorder or medical condition. Such devices suitably will comprise at least one of the compositions of the present invention, in the form of a coating on the device or a composition that is embedded within the device such that it is released from or elutes from the device once implanted within the body of the human or veterinary animal. Suitable such devices include, but are not limited to, artificial joints, stents, catheters, sutures, bone screws, bone plates, prosthetics (e.g., artificial limbs, body structures, organs, etc.), absorbable or non-absorbable meshes, absorbable or non-absorbable patches, drug-releasing wafers, brain neurostimulators (e.g., deep brain neurostimulators), gastric stimulators, cochlear implants, cardiac defibrillators, cardiac pacemakers, insulin pumps, internal infusion pumps, and the like. Suitable other devices useful in accordance with this aspect of the invention will be readily apparent to the ordinarily skilled artisan.

The devices provided by this aspect of the invention are useful for treating, preventing, ameliorating or diagnosing diseases, disorders and medical conditions in humans or veterinary animals suffering from or predisposed to such diseases, disorders or medical conditions. In methods according to this aspect, one or more medical devices of the invention is implanted into the human or veterinary animal, and medical condition of the human or veterinary animal is monitored until the disease, disorder or medical condition is cured, ameliorated or prevented in the human or veterinary animal. Suitable diseases, disorders and medical conditions that may be cured, treated, ameliorated or prevented using the devices and methods of the invention include cancers (such as those described elsewhere herein), and diseases or disorders affecting an organ system of the human or veterinary animal including the integumentary system (particularly diseases or disorders of the skin such as those described in detail herein), the muscular system, the skeletal system (particularly diseases or disorder of the bones, joints, cartilage, tendons or ligaments such as those described in detail herein), the nervous system (particularly those of the brain or the eye (including but not limited to glaucoma, cataracts, vitreous adhesions or floaters, macular degeneration, dry eye syndrome, corneal keratitis, non-infectious corneal ulceration, non-infectious corneal melting, infectious corneal ulceration, infectious corneal melting, conjunctivitis, Stevens-Johnson Syndrome, scleritis, episcleritis, ectasia, keratoconus, corneal laceration, corneal erosion, corneal abrasion, and a post-operative affliction of the eye resulting from eye surgery such as a post-operative cataract surgery state requiring medication or a post-operative glaucoma surgery state requiring medication)), the circulatory system, the lymphatic system, the respiratory system (including those diseases or disorders affecting the epiglottis, the trachea, a bronchus, a bronchiole or a lung in the human or veterinary animal, particularly those diseases and disorders described in detail herein), the endocrine system, the urinary/excretory system (including those diseases or disorders affecting the kidney, the ureter, the urinary bladder, the upper urinary tract (i.e., the renal pelvis), the ureter or the urethra of the human or veterinary animal, particularly those diseases and disorders described in detail herein), the reproductive system (including diseases and disorders affecting the testicle, the prostate, the penis, the vagina, the cervix, the uterus, a fallopian tube or an ovary in said human or veterinary animal, particularly those diseases and disorders described in detail herein) and the digestive system (including those diseases or disorders affecting the esophagus, stomach, small intestine, colon or rectum in said human or veterinary animal, particularly those diseases and disorders described in detail herein). Suitable methods for implanting one or more of the devices provided by this aspect of the invention into a human or veterinary animal, to accomplish the treatment, prevention, amelioration or diagnosis of a disease, disorder or medical or physical condition in the human or veterinary animal will be familiar to the person of ordinary skill in the relevant medical and surgical arts.

Concentrations of the CMPs, or of the CMP-TC conjugates, useful in treating, preventing, ameliorating or diagnosing one or more diseases or disorders according to the methods of the present invention will be readily apparent to the artisan ordinarily skilled in the pharmaceutical and medical arts. For unconjugated CMPs, suitable amounts or concentrations of CMPs to be administered to a subject, particularly a human or veterinary animal, suitable amounts or concentrations of CMPs per kilogram (kg) of body mass are from about 1 mg/kg to about 10 mg/kg, about 1 mg/kg to about 5 mg/kg, and about 1 mg/kg, about 2 mg/kg, about 3 mg/kg, about 4 mg/kg, or about 5 mg/kg. For conjugated CMP-TCs, the same amounts or concentrations of CMPs per kg of body mass are suitably administered to the subject, and the amount of active pharmaceutical ingredient or biologic is calculated during the conjugation process to deliver therapeutically effective amounts of the desired active pharmaceutical ingredient or biologic, depending upon the disease or disorder that is to be treated, prevented, ameliorated or diagnosed in the human or veterinary animal. Suitable amounts or concentrations of active pharmaceutical ingredients or biologics to be used according to this aspect of the invention will be familiar to the ordinarily skilled artisan, and can be readily determined from information contained herein and other information that is available in the relevant arts.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1: Effect of CMPs and CMP-TC Conjugates on In Vivo Healing of Mouse Corneal Epithelium To examine the possible therapeutic effects of CMPs and CMP-TC conjugates of the invention, studies were designed to test certain CMPs and CMP-TC conjugates in an in vivo setting the healing of the corneal epithelium in wounded mouse eyes. Female mice (8-week-old C57BL/6; seven mice per sample tested) were anesthetized, and corneas of the mouse eyes were wounded with a 1.5 mm superficial epithelial wound of sufficient depth to expose the anterior stroma thereby damaging and exposing the collagen matrix. Wounds were created via trephine, followed by an Algerbrush scouring technique (see Carlson, E., et al., "Impact of Hyaluronic Acid-Containing Artificial Tear Products on Reepithelialization in an In Vivo Corneal Wound Model," J. Ocular Pharmacol. Ther., published online Feb. 2, 2018, accessed at doi.org/10.1089/jop.2017.0080). Following wounding, corneas were treated with 25 nM (about 3 mg/kg) CMPs or CMP-TC conjugates, in aqueous PBS. Negative control mice were treated with vehicle only (PBS), and positive control mice were treated with 100 ng/mL epidermal growth factor (EGF). Wound size at various time points over 48 hours was examined by fluorescein staining (see Carlson et al., id.), and documented via fluorescent photomicrography, and quantified using Image J software (see Rush, J. S. et al., Investig. Ophthalmol. Visual Sci. 57(14): 5864-5871 (2016); Rush, J. S. et al., Investig. Ophthalmol. Visual Sci. 55(8):4691-4699 (2014)). Results are depicted in the FIGURE.

The FIGURE shows that the CMPs and CMP-TC conjugates of the invention significantly accelerated the reepithelialization and healing of the subepithelial stroma in the cornea of mouse eyes, vs. both EGF and vehicle. The left-hand column shows the size of the wound (visualized as the circle of fluorescein fluorescence in each photomicrograph) immediately after induction of the wound, while the right-hand column shows the size of the wound 16 hours post-wounding and post-treatment with various test substances. PBS: negative control; EGF: positive control. "Cmpd 3": a (Pro-Pro-Gly)$_7$ CMP of the invention (SEQ ID NO:1); "Cmpd 10": a (Hyp-Pro-Gly)$_7$ CMP—Substance P (SubP) conjugate of the invention (SEQ ID NO:390). The results demonstrate that both Cmpd 3 and Cmpd 10 demonstrated significant acceleration of wound healing in mouse cornea and corneal stroma (indicated by a reduction in the diameter and diminution in intensity of the fluorescence) within 16 hours post-treatment, compared to both PBS and EGF controls which showed a lower level of healing. These results support the use of the CMPs and CMP-TC conjugates of the present invention in promoting corneal wound healing and stromal collagen repair in wounded mouse eye, a model of a variety of human and veterinary animal ocular conditions including dry eye and corneal laceration or ulceration of a variety of etiologies.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Hence, in addition to those specifically described herein, other suitable embodiments of the invention will be readily apparent to one of ordinary skill in the art based upon the foregoing description and examples, and upon knowledge generally available in the relevant arts. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

All references cited herein, including U.S. patents and published patent applications, international patents and patent applications, and journal references or other publicly available documents, are incorporated herein by reference in their entireties to the same extent as if each reference had been specifically cited for the portion or portions of such reference applicable to the section of this application to which it is relevant.

What is claimed is:

1. A method of treating an ocular disease, disorder or wound selected from the group consisting of glaucoma, dry eye syndrome, conjunctivitis, corneal keratitis, corneal laceration, corneal erosion, and corneal abrasion, in a human or veterinary animal suffering from said ocular disease, disorder or wound, comprising administering a composition comprising (a) at least one collagen mimetic peptide (CMP) comprising the amino acid sequence of SEQ ID NO: 1, and (b) one or more pharmaceutically suitable carriers to an eye of said human or veterinary animal in a dosage sufficient to treat said ocular disease, disorder or wound, monitoring the condition of the eye in said human or veterinary animal over time, and readministering said composition to the eye until said ocular disease, disorder or wound is treated or ameliorated.

2. The method of claim 1, wherein said ocular disease, disorder or wound is selected from the group consisting of, dry eye syndrome, corneal keratitis, corneal laceration, corneal erosion, and corneal abrasion.

3. The method of claim 1, wherein said composition is administered to the eye conjunctivally or subconjunctivally.

4. The method of claim 3, wherein said subconjunctival administration is achieved by administering said composition into the subconjunctival fornix.

5. The method of claim 1, wherein said composition is administered to the eye in the form of one or more drops of solution or a suspension that contains the composition.

6. The method of claim 1, wherein said composition is administered to the eye via injection.

7. The method of claim 1, wherein said composition is administered to the eye in the form of a coating on a solid material that is implanted into an eye structure.

8. The method of claim 1, wherein said composition is administered to the eye in the form of a wafer, film, gel, mesh or patch.

9. The method of claim 1, wherein said composition is attached to one or more spheres or nanoparticles that are delivered to or into an eye structure.

10. The method of claim 1, wherein said collagen mimetic peptide is attached to at least one therapeutic compound (TC) to form a CMP-TC conjugate.

11. The method of claim 10, wherein said at least one therapeutic compound comprises at least one reactive hydroxyl group capable of being cross-linked to said collagen mimetic peptide.

12. The method of claim 11, wherein said at least one therapeutic compound is directly attached to said collagen mimetic peptide via an amino group on said collagen mimetic peptide linked to a hydroxyl group on said therapeutic compound.

13. The method of claim 10, wherein said at least one therapeutic compound is selected from the group consisting of a steroidal anti-inflammatory drug, a nonsteroidal anti-inflammatory drug, a topical anesthetic, a vitamin or a derivative or precursor thereof, therapeutic enzyme or a therapeutic fragment thereof, an antibiotic, a therapeutic monoclonal antibody or a therapeutic fragment thereof, a therapeutic fusion protein, a prostaglandin analogue, a growth factor, a neuropeptide, an α-adrenergic antagonist, a β-adrenergic antagonist, a cell surface receptor antagonist, a carbonic anhydrase inhibitor, and pharmaceutically acceptable salts, esters and derivatives thereof.

14. The method of claim 13, wherein said prostaglandin analogue is selected from the group consisting of latanoprost, travoprost, tafluprost, unoprostone, tatanoprostene bunod and bimatoprost, and pharmaceutically acceptable salts, esters and derivatives thereof.

15. The method of claim 14, wherein said prostaglandin analogue is latanoprost.

16. The method of claim 10, wherein said collagen mimetic peptide is covalently attached directly to said at least one therapeutic compound.

17. The method of claim 10, wherein said collagen mimetic peptide is indirectly attached to said at least one therapeutic compound via use of an attachment means.

18. The method of claim 17, wherein said attachment means comprises at least one polymeric chain having a first end and a second end.

19. The method of claim 18, wherein said polymeric chain is a linear polyethyleneglycol chain comprising at least four ethyleneglycol monomers.

20. The method of claim 19, wherein said polymeric chain comprises from twenty to twenty-five ethyleneglycol monomers.

21. The method of claim 10, wherein said collagen mimetic peptide comprises at least one biotin moiety and said therapeutic molecule comprises at least one avidin or streptavidin moiety, and wherein said biotin moiety on said collagen mimetic peptide binds to said avidin or streptavidin moiety on said therapeutic compound, thereby attaching said collagen mimetic peptide to said therapeutic compound.

22. The method of claim 10, wherein said collagen mimetic peptide comprises at least one avidin or streptavidin moiety and said therapeutic molecule comprises at least one biotin moiety, and wherein said avidin or streptavidin moiety on said collagen mimetic peptide binds to said biotin moiety on said therapeutic compound, thereby attaching said collagen mimetic peptide to said therapeutic compound.

23. The method of claim 1, wherein said ocular disease, disorder or wound is dry eye syndrome.

\* \* \* \* \*